US012646215B2

(12) United States Patent
Amthor et al.

(10) Patent No.: US 12,646,215 B2
(45) Date of Patent: Jun. 2, 2026

(54) METHOD AND DEVICE FOR PREPARING DATA FOR IDENTIFYING ANALYTES

(71) Applicant: Carl Zeiss Microscopy GmbH, Jena (DE)

(72) Inventors: Manuel Amthor, Jena (DE); Daniel Haase, Zoellnitz (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 270 days.

(21) Appl. No.: 18/519,266

(22) Filed: Nov. 27, 2023

(65) Prior Publication Data

US 2024/0177350 A1 May 30, 2024

(30) Foreign Application Priority Data

Nov. 28, 2022 (DE) ..................... 10 2022 131 450.2

(51) Int. Cl.
| | |
|---|---|
| *G06T 7/90* | (2017.01) |
| *G16B 30/00* | (2019.01) |
| *G16B 40/20* | (2019.01) |

(52) U.S. Cl.
CPC ................ *G06T 7/90* (2017.01); *G16B 30/00* (2019.02); *G16B 40/20* (2019.02);
(Continued)

(58) Field of Classification Search
CPC ............. G06T 7/90; G06T 2207/10024; G06T 2207/10056; G06T 2207/20081;
(Continued)

(56) References Cited

U.S. PATENT DOCUMENTS

| | | | | |
|---|---|---|---|---|
| 10,790,056 B1* | 9/2020 | Accomazzi | ........... | G06T 11/008 |
| 11,169,368 B2 | 11/2021 | Marsh et al. | | |

(Continued)

FOREIGN PATENT DOCUMENTS

| | | |
|---|---|---|
| CN | 1307263 C | 3/2007 |
| CN | 103559724 A | 2/2014 |

(Continued)

OTHER PUBLICATIONS

Machine translation for CN 114742803 (Year: 2022).*

(Continued)

*Primary Examiner* — Qian Yang
(74) *Attorney, Agent, or Firm* — HoustonHogle LLP

(57) ABSTRACT

A method for preparing data for identifying analytes by coloring one or more analytes with markers in multiple coloring rounds, the markers in each case being specific for a certain set of analytes, detecting multiple markers using a camera, which for each coloring round generates at least one image that includes multiple pixels to which a color value is assigned in each case as color information, and includes colored signals and uncolored signals, wherein a colored signal is a pixel containing color information of a marker, and an uncolored signal is a pixel containing color information that is not based on a marker. A data point in each case includes one or more contiguous pixels in the images of the multiple coloring rounds that are assigned to the same location in a sample.

27 Claims, 11 Drawing Sheets

(52) U.S. Cl.
CPC .............. *G06T 2207/10024* (2013.01); *G06T 2207/10056* (2013.01); *G06T 2207/20081* (2013.01); *G06T 2207/20084* (2013.01); *G06T 2207/30024* (2013.01); *G06T 2207/30204* (2013.01)

(58) Field of Classification Search
CPC . G06T 2207/20084; G06T 2207/30024; G06T 2207/30204; G06T 7/0012; G16B 30/00; G16B 40/20; G16B 20/30; G06N 20/00; G06V 10/26; G06V 10/764
See application file for complete search history.

(56) References Cited

U.S. PATENT DOCUMENTS

| | | | |
|---|---|---|---|
| 11,568,301 B1 * | 1/2023 | Yueh ...................... | G06N 20/00 |
| 2014/0118524 A1 | 5/2014 | Munck et al. | |
| 2014/0286529 A1 * | 9/2014 | Sprenger ............... | G06V 20/69 |
| | | | 382/103 |
| 2020/0033267 A1 | 1/2020 | Klaiman | |
| 2021/0147922 A1 | 5/2021 | Urnov et al. | |
| 2021/0208076 A1 | 7/2021 | Chang et al. | |

FOREIGN PATENT DOCUMENTS

| | | | |
|---|---|---|---|
| CN | 107845085 B | | 3/2018 |
| CN | 112929743 | * | 6/2021 |
| CN | 113470041 | * | 4/2022 |
| CN | 114742803 | * | 7/2022 |
| DE | 10063112 A1 | | 6/2002 |
| DE | 69719966 T2 | | 12/2003 |
| DE | 102005022880 B4 | | 12/2010 |
| EP | 2992115 B1 | | 3/2020 |
| JP | 2012122852 A | | 6/2012 |
| WO | WO 2003098313 A2 | | 11/2003 |
| WO | WO 2011112634 A2 | | 9/2011 |
| WO | WO 2017216270 A1 | | 12/2017 |
| WO | WO 2019115801 A1 | | 6/2019 |
| WO | WO 2020254519 A1 | | 12/2020 |
| WO | WO 2021234698 A1 | | 11/2021 |
| WO | WO 2021255244 A1 | | 12/2021 |

OTHER PUBLICATIONS

Machine translation for CN 112929743 (Year: 2021).*
Machine translation for CN 113470041 (Year: 2022).*
Research Report issued in the DE Patent Application No. 10 2022 131 450.2, mailed on Oct. 25, 2023. 5 pages.

* cited by examiner

| RNA | Codeword |
|-----|----------|
| A | 1010100000000010 |
| B | 1100000000110001 |
| C | 0010010011000010 |
| ... | ... |

METHOD AND DEVICE FOR PREPARING DATA FOR IDENTIFYING ANALYTES

RELATED APPLICATIONS

This application claims priority to German Patent Application No. 102022131450.2, filed on Nov. 28, 2022, which is incorporated herein by reference in its entirety.

The present invention relates to a method and a device for preparing data for identifying analytes.

EP 2 992 115 B1 provides a method for identifying nucleic acid sequences by coloring the nucleic acid sequences to be identified, using markers in multiple coloring rounds. The markers are made up of oligonucleotides and dyes coupled thereto, which are generally fluorescent dyes. The oligonucleotides are specific for certain segments of the nucleic acid sequences that are to be identified. However, the individual oligonucleotides of the markers are not unique for the particular nucleic acid sequences. Due to the multiple coloring rounds, however, it is possible to carry out an unambiguous determination of the nucleic acid sequences, since multiple different markers may be assigned to a certain oligonucleotide after carrying out the multiple coloring rounds, and the assigned multiple markers are then unambiguous for the particular nucleic acid sequences.

By use of this method, many different nucleic acid sequences may be detected in vitro, for example in a cell, by means of a fluorescence microscope. The nucleic acid sequences may be RNA, in particular mRNA or tRNA. The nucleic acid sequences may also be a DNA segment.

A plurality of nucleic acid sequences is often present in a sample, and may be identified in parallel using the coloring rounds explained above, even if different nucleic acid sequences are involved. The more nucleic acid sequences present in the sample, the larger is the number of markers to be detected in the particular coloring rounds. With automatic detection and evaluation of the color information in question, the color information of all markers in the sample must be detected, and must also be distinguished from color information in the sample that is not caused by markers coupled to analytes.

WO 2020/254519 A1 and WO 2021/255244 A1 provide a further method for identifying analytes. The analytes may be proteins or nucleic acid sequences. In this method, probes that are specific for the particular analytes are initially coupled to the analytes. The probes have oligonucleotide residues that do no hybridize with the analytes. Decoding oligonucleotides having a supernatant for the free residues are hybridized at these free residues. Marker molecules are hybridized using a dye at the supernatants. In this method as well, a series of pieces of color information at the analytes in question is generated in multiple coloring rounds, which allows the particular analyte present to be deduced.

In practice, it has been shown that the data volume for describing the color information of the multiple coloring rounds may be several terabytes. Processing such large data volumes requires a correspondingly large memory. The resulting acquisition and maintenance costs are correspondingly high. Preferred as data memory are SSD hard drives, which on the one hand are suitable for storing such large data volumes, and which on the other hand allow rapid access to the data. However, SSD hard drives allow only a limited number of write cycles. With such large data volumes this limit is quickly reached, which may result in failure of the system.

In addition, an evaluation of such large data volumes requires significant computing effort and a correspondingly longer time. This limits the throughput of samples.

The object of the invention is to provide a method and a device for preparing data for identifying nucleic acid sequences by coloring one or more analytes with markers in multiple coloring rounds, which may be carried out efficiently and economically and allows a high sample throughput.

The object is achieved by the subject matter of the independent claims. Advantageous embodiments are set forth in the respective subclaims.

According to a first aspect of the invention (aspect A), a method for preparing data for identifying analytes by coloring one or more analytes with markers in multiple coloring rounds is provided, the markers in each case being specific for a certain set of analytes. The markers are detected using a camera, which for each coloring round generates at least one image that contains multiple pixels and includes colored signals and uncolored signals, a colored signal being a pixel containing color information of a marker, and an uncolored signal being a pixel containing color information that is not based on a marker. The images of the particular coloring rounds are stored for evaluating the color information, a data point in each case including one or more contiguous pixels in the images of the multiple coloring rounds, which are assigned to the same location in a sample.

The method is characterized in that each data point is assessed, based on the color information at least of the present image, for whether the data point may be a candidate data point, i.e., that it may contain colored signals and may thus encode an analyte, and when the color information is stored, the color information of the data points of the images which are reliably not a candidate data point, based on the assessment, are eliminated.

In this way, when the color information is stored, the color information of the pixels of the images that contain no color information of the markers is eliminated, and the images are stored without the eliminated color information. As a result of the images being stored without the eliminated color information, the data volume to be stored is significantly reduced. This reduction in the data volume of color information allows simple and rapid processing of the color information. The capacity of the memory device may be small compared to conventional methods, and the number of write cycles on the memory device is correspondingly reduced. Efficient, simple, and rapid processing of the color information is thus possible.

A data point encompasses the set of all pixels of the different images that represent a certain location in the sample. A data point that encodes an analyte may thus contain colored signals and uncolored signals.

According to the present invention, color information may be combined for multiple neighboring pixels. The combined color information then forms the color information of the data point that is combined from multiple pixels. Neighboring pixels, for example 2×2, 4×4, or 6×6 pixels, are typically combined here. When image stacks, also referred to as Z images, are recorded in each case in the experiment, 2×2, 4×4, or 6×6 pixels may also be combined.

This method may be carried out in vitro, for example based on a cell sample present on a sample glass, using a microscope that has a camera for automatically generating images of the sample. The sample may, for example, be a cell sample containing one or more cells.

Each data point may be assessed, based on the color information of all previous coloring rounds and/or a subset of the previous coloring rounds, and/or based on color information of neighboring data points, for whether the data point is a candidate data point.

When the color information is eliminated, the pixels that contain no relevant color information may be completely removed. However, it is also possible for the pixels that contain no relevant color information to be set to a predetermined color value, for example "0." Since the pixels containing nonrelevant color information generally form contiguous areas in an image, they may be stored very efficiently, wherein as a whole, only the one predetermined color value is assigned once in such an area. If the color information of neighboring data points is entered into the assessment of whether a data point is a candidate data point, a data point is assessed as containing no relevant color information only if it is no longer needed for the assessment of neighboring data points, because all data points are assessed.

An image may encompass a two-dimensional depiction including multiple pixels as image points. The image may also encompass a three-dimensional depiction including multiple voxels as image points, it being possible for the images to include time information as an additional dimension. The time information may be used not only to indicate the point in time when an individual image has been recorded, but also to represent a time series including multiple successive images, the time information including the points in time of the individual images. A three-dimensional depiction is also referred as an image stack or Z image, which includes multiple two-dimensional image planes.

The data points may be assessed using a processing model of a machine learning system.

The processing model may have been trained using an annotated data set, which as input includes series of color information of one or more data points, and which as target output includes a classification of whether the particular series originates from a candidate data point or a background data point. Such a target output may, for example, include images in which areas that depict the color information of one of the markers are annotated, and/or in which areas that contain no color information from markers are annotated. The series of color information of one or more data points may also be input as series of microscopic images. The training of such a processing model is referred to as supervised learning.

In the prior art, primarily color values of very bright data points are analyzed for the analyte decoding, since they are very easy to identify based on a threshold value. The inventors have found that the input series of data points that encode an analyte, i.e., candidate data points, in each case have at least a specified ratio between the color values of colored and/or uncolored signals of the particular input series, which for the input series of candidate data points results in a characteristic signature that includes the at least one specified ratio of the color values of the colored and/or uncolored signals. Based on the specified ratio, colored and uncolored signals may be recognized in an input series, and the number of colored signals in a signal series may thus also be determined. Based on the specified ratio or based on the characteristic signature, a processing model may be trained to identify the colored and uncolored signals, and thus to identify the candidate data points, based on the series of color values that is input.

The specified ratio may be a certain distance between the color values, a quotient of the color values, or a certain number of color values that have a higher color value than the others, it being possible for the ratio to be learned in each case for normalized color values or for unnormalized color values. Analytically, the characteristic signature is difficult to define and may be different for various types of analytes; however, it has been shown that with adequate training, processing models such as neural networks may identify the characteristic signature or the specified ratio very well.

After a new experiment, after identifying the analytes a further annotated data set may preferably be generated based on the compressed images that have been stored without the color information of the data points and that encode no analyte, wherein for a selection of the data points that encode no analyte, the color information is also stored, and the pieces of color information of the data points that encode no analyte are used as background data points in the further annotated data set, and the processing model is trained using the further annotated data set.

The selection of the data points that encode no analyte preferably includes to the greatest possible extent data points which in the new experiment have been identified as background data points only in one of the latest possible coloring rounds of the experiment.

In a new experiment, as a result of always also storing a selection of background data points and subsequently retraining the processing model using these further annotated data, a processing model may be trained even better for identifying candidate data points. As a result of incorporating background data points into the further annotated data set which have been recognized as background data points only in late coloring rounds, it is possible to further improve the recognition of background data points that are difficult to identify.

The identification of the analytes after a new experiment preferably also includes an identification of background data points that have been wrongly identified as candidate data points, wherein background data points wrongly identified as candidate data points may also be incorporated into the further annotated data set.

As a result of also incorporating background data points, wrongly identified as candidate data points, into the further annotated data set, the identification of background data points may be even further improved.

A processing model in which areas of the images containing candidate pixels, as a positive example, and/or areas of the images containing background pixels, as a negative example, are classified as binary, may be a classification model.

The processing model may also be a semantic segmentation model via which the candidate data points and/or background data points are semantically segmented.

The processing model may also be an image-to-image model which in particular is trained to output a heat map, via which likelihoods or densities of candidate data points and/or background data points are output.

A processing model may be trained and designed to assess all coloring rounds. However, multiple models may also be trained and designed for each individual coloring round or for groups of coloring rounds.

The processing model may be a detection model that is trained to detect candidate data points, in particular a list of the coordinates of the candidate data points being output.

The detection model for detecting the extent of the candidate data points is preferably trained in such a way that the output list, in addition to the coordinates of the candidate data points, includes the extent of the particular candidate data points.

A processing model that includes several such submodels that are trained for groups of coloring rounds may be advantageous when a sample is simultaneously colored with multiple different dyes. The color information of all markers is then simultaneously present in a color image. Such a color image thus simultaneously contains the information of multiple coloring rounds. Such a color image may then be spectrally decomposed into images, each of these images then depicting only a spectral range that includes the color of the particular dye. This is referred to as a color channel. However, if a color image that includes several such color channels is supplied to the processing model as input data, the processing model is to be trained in such a way that it can process multiple coloring rounds that are represented by the particular color channel.

However, such color images are generally decomposed into multiple separate images for the particular color channels. These images are monochrome images that contain the color information via intensity values for the color of the particular color channel.

The term "intensity values" or the synonym "intensity" is therefore understood below to mean that either the intensity of a pixel of an image is depicted for a certain color of a predetermined color channel, or intensities of different basic colors of a color space of a color image are depicted.

The areas that depict the color information of a data point may include an individual pixel and/or multiple contiguous pixels. An area with multiple contiguous pixels extends in one dimension, preferably not over more than ten pixels. Such an area with multiple pixels preferably extends in one dimension over not more than seven pixels or not more than five pixels. In other words, such areas, which are represented either by an individual pixel or by multiple contiguous pixels, are in each case assigned to a type of analyte to which the markers are able to bind.

When the color information is stored after one of the coloring rounds, data points that have already been eliminated after a preceding coloring round are not taken into account. The processing model may be trained to carry out this elimination of data points that have already been eliminated in preceding coloring rounds. For this purpose, during the training of the processing model an annotated data set is used which also includes the data points that were eliminated in the preceding coloring rounds, these data points being correspondingly annotated. The elimination of data points that have already been eliminated after a preceding coloring round may also be appropriately hard-coded, so that the processing model may be supplied with the particular detected image that is adjusted for these areas.

The color information of certain pixels may also be eliminated; although their color values may be assessed as color values of a marker based on their intensity and/or their characteristic signature, the color values of any of these pixels are not assignable to an analyte after several coloring rounds, since the series of color values of the particular data point cannot correspond to any possible pattern of color values for an analyte. Use may be made of the fact that, with such a method for identifying analytes using multiple different markers, only a relatively small subset of patterns of all potentially possible patterns that can be generated with these markers can actually occur. Patterns that are theoretically possible, but which in practice cannot occur because there is no analyte that generates such a pattern of color values, may thus be assessed as nonrelevant, and the corresponding color values may be eliminated.

The checking of such a series of color values of a pixel may be carried out using a scoring model, the pixels with a characteristic signature being assessed as potential markers, and the series of color values of the potential markers being checked for whether they may correspond to a possible pattern of an analyte.

The processing model may be additionally supplied with context information as input data.

The context information may describe further properties of the sample and/or of the experiment and/or of the expected analytes, and in particular parameters for coloring the sample and/or the expected number of analytes or also the expected ratio of the analytes contained in the sample.

Based on the context information, the sensitivity of the assessment of the data points may be adjusted, and/or a processing model may be automatically selected from a set of processing models.

The context information may be obtained in advance via a segmentation. The context information differentiates, for example, the cell areas from areas that are not assigned to a cell.

The sensitivity of the processing model, which is used to assess whether a data point may be a candidate data point, may be varied for the different coloring rounds.

A higher sensitivity is preferably applied in the first coloring rounds than in the later coloring rounds. A high sensitivity, in comparison to a low sensitivity, means that many data points are assessed as candidate data points.

The order of the coloring rounds may be selected in such a way that the number of measured markers or candidate data points is maximized in early rounds. Since each marker is specific for a subset of all detectable analytes, in the first coloring rounds it is advantageous to use markers whose subset of detectable analytes for which the markers are specific overlap as little as possible. The coloring rounds are preferably selected in such a way that all or almost all detectable analytes in the first five coloring rounds, and preferably in the first four or first three coloring rounds, are marked.

It is also possible to use specialized markers for the first coloring rounds which are very nonspecific; i.e., their subset is as large as possible, and optionally even includes all potentially detectable analytes.

The analytes may be nucleic acid sequences.

The markers may in each case have an oligonucleotide sequence that is specific for a segment of the nucleic acid sequence, and a dye molecule coupled thereto. The dye molecule is preferably a fluorescent dye molecule.

According to one preferred embodiment, the marker of the first coloring rounds or the markers of the first coloring round and/or of the first and the second coloring round may have shorter oligonucleotide sequences than in the subsequent coloring rounds. Markers with shorter oligonucleotide sequences are nonspecific. The oligonucleotide sequences of the markers of the first coloring round or of the first and second coloring rounds preferably include no more than ten nucleotides, in particular no more than eight nucleotides, and in particular no more than five nucleotides.

The shorter the oligonucleotide sequence of the markers, the more nonspecific the markers are. As a result, the markers couple to many different nucleic acid sequences. During a coloring round, in particular the first coloring round or the first and second coloring rounds, multiple different markers, in particular multiple markers with short oligonucleotide sequences (for example, no more than ten or no more than eight or no more than five oligonucleotide sequences) that differ in their oligonucleotide sequences may also be used.

Due to the use of one or more such nonspecific markers, all or almost all nucleic acid sequences are already marked with a marker in the first coloring round or at least in the first and second coloring rounds, so that, even after the first coloring round or at the latest, after the second coloring round, all or almost all nucleic acid sequences are known, and in the subsequent coloring rounds only the color information of the pixels that are assigned in each case to a nucleic acid sequence is considered or evaluated. In this way, all relevant areas of the images may be identified with a single coloring round or with just two coloring rounds, so that only these relevant areas are examined in the subsequent coloring rounds. The further coloring rounds may also use different types of markers or marker systems, for example those known from WO 2020/254519 A1 and WO 2021/255244 A1.

The images may be stored in one of the following formats:
background data points that encode no analyte are set to a certain value, in particular "0," wherein areas of the images whose pixels are assigned the same value are compressed during storage (referred to below as "PNG format"),
a binary array, in which storage is carried out in an array, using only one bit, regardless of whether a candidate data point or background data point is involved, wherein an additional list may be stored in which all color values of the candidate data points are continuously stored, and an assignment of the candidate data points of the array to the color values of the list takes place by use of an index,
a sparse matrix that includes a list containing coordinates and color values of all candidate data points and optionally their extent.

The images of the different coloring rounds may be stored using different formats, in particular the images of the first coloring rounds being stored in the PNG format, and the images of the subsequent coloring rounds being stored as a sparse matrix or as a binary array.

The analytes may be identified based on the determined and compressed stored color information.

A machine learning system including a processing model for carrying out a method explained above may be trained using the following method steps:
providing an annotated data set, and
optimizing an objective function by adapting the model parameters of the processing model, the objective function detecting a difference between a result output that is output by the processing model and a target output.

This training method may be characterized in that the annotated data set includes at least one target signal series of a candidate data point as well as a target signal series of a background data point, and the processing model processes a partial signal series of the target signal series of the annotated data set as input, and based on an output of the processing model, a data point corresponding to the particular target signal series is assessed as a background data point or a candidate data point.

According to a second aspect of the invention (aspect B), a method for preparing data for identifying analytes in a sample is provided, in which in an experiment one or more analytes are colored with markers in multiple coloring rounds, the markers in each case being specific for a certain set of analytes. The multiple markers are detected using a camera, which for each coloring round generates at least one image containing multiple pixels and color values assigned thereto, the image including colored signals and uncolored signals. A colored signal is a pixel having a color value that originates from a marker, and an uncolored signal is a pixel having a color value that is not based on a marker. The color information of the particular coloring rounds is stored for evaluating the color information, a data point in each case including one or more contiguous pixels in the images of the multiple coloring rounds that are assigned to the same location in a sample.

This method is characterized in that for each data point of the multiple images of the sample, the particular color values are assessed for whether they represent a colored signal in each case and accordingly encode an analyte, and the n color values of the different coloring rounds that most likely represent a colored signal are selected for each data point, where n is an integer that is less than the total number of coloring rounds of an experiment. When the color information is stored, the color values that are not selected are eliminated.

The data volume of the color information is significantly reduced due to omitting the nonselected color values. This reduction in the data volume of color information allows simple and rapid processing of the color information. The capacity of the memory device may be smaller compared to conventional methods, and the number of write cycles on the memory device is correspondingly reduced. Efficient, simple, and rapid processing of the color information is thus possible.

In this method, the images are primarily stored only with the selected color values. In addition to the selected color values, further information may be stored, as explained in greater detail below, but unneeded color information is omitted; as a result, the quality of the evaluation of the images for identifying analytes is not adversely affected, but the data volume is significantly reduced. The selection of the n color values may be carried out using a scoring model of a machine learning system. The scoring model is trained on the criteria that are the basis of assessing whether the color values represent a colored signal.

In this method, after each coloring round the data points may be assessed, and the color information recorded in the present coloring round may be stored; the maximum n color values that have been output by the scoring model after an immediately preceding coloring round, as well as the color value of the data point recorded in the coloring round, are entered into the scoring model as input for a data point, and based on this input the scoring model outputs n color values, and the color value that least likely represents a colored signal is sorted out. In this embodiment of the method, all relevant color values detected in the preceding coloring rounds are supplied to the scoring model as input data. In particular after the first rounds, the set of color values previously selected by the scoring model may also contain color values that depict no marker. Even if multiple color values that are not based on a marker are present here, only one color value is sorted out, in particular the color value that is the least likely to be assignable to a marker. After the first coloring rounds, also fewer than n color values per data point are present. The color values that are not present may be filled with a placeholder ("0," for example), and are then also the first to be sorted out in the next rounds. After each round, the color value that is the least likely to be assigned to a marker is sorted out, so that only the n color values with which the analyte is encoded remain at the end.

In one alternative embodiment of the method, after each coloring round the data points are assessed and the image recorded in the present coloring round is stored, and only the color information of the presently recorded image is input into the scoring model.

If the scoring model is designed as a convolutional neural network (CNN) or a multilayer perceptron (MLP), in addition to the color information of the present coloring round, also the outputs of the previous round (selected color values and assessments) are to be input into the scoring model. In contrast, for a sequential model (recurrent neural network (RNN), for example) it is sufficient to input only the color information of the present coloring round.

The scoring model may have been trained using an annotated data set, which as input data contains microscopic images or color values of the pixels and corresponding target outputs, each of which defines whether the color values represent a colored signal and/or an uncolored signal.

The annotated data set may be created using a method in which the images of the multiple coloring rounds together with their color values are stored in uncompressed form and then evaluated; in the training, for each coloring round the maximum n color values, which may represent a colored signal according to predetermined criteria, and the color value of the data point obtained in the particular coloring round are entered into the processing model as input for a data point. An objective function is computed, and the objective function detects a difference between the n color values that are output by the processing model, which most likely represent a colored signal, and the n color values to be selected according to the annotated data set, which according to the assessment in the annotated data set most likely represent a colored signal. The objective function is optimized by adapting the model parameters.

The annotated data may in principle have been generated via one or more of the following steps:

- simulating signals of the various markers using a representative background image and a known point spread function of a microscope,
- generating the annotated data set by use of a generative model that has been trained on comparable data,
- recording reference images that include at least one background image, and for each of the background images for each of the types of analytes, and recording at least one image in which analytes of the particular type of analyte are marked,
- carrying out a conventional method for spatial identification of analytes,
- recording a representative background image and subtracting, pixel by pixel, the color values of the representative background image from the color values of the images on which the annotated data set is based, before providing the annotated data set, so that the annotated data set includes only background-corrected color values,
- obtaining the annotated data set based on a portion of an experiment, so that the trained scoring model may be applied to the remaining portion of the experiment.

The fact that an annotated data set may be generated according to one of the above-mentioned steps applies for all aspects of the present invention.

The data points for selecting the n color values may be assessed, according to predetermined criteria, for whether they represent a colored signal, taking into account the following criteria: the intensity, the color, and/or the extent of the data point. Such a selection may also take place analytically (hard-coded) or may be a combination with a machine learning system.

The criteria for selecting the n color values may include threshold values for a minimum and/or maximum intensity, it being possible for the threshold values to be statically specified or dynamically determined, and/or for only the threshold values to vary for a minimum and/or maximum intensity as a function of the color of the color values, and/or for the selection to be carried out via a minimum distance from predetermined target values of the intensity, color, and/or extent. These criteria may be applied for an analytical assessment of the color values as well as for generating an annotated data set; the target outputs of the annotated data may be determined using these criteria.

Additional information besides the selected color values may be stored. This additional information may be, for example, statistical information concerning all color values of a particular data point and/or statistical information concerning the nonselected color values of one of the data points and/or statistical information concerning the selected color values of one of the data points. The additional information may be information concerning the coloring round (number of the coloring round, point in time of the coloring round, etc.), and/or a sliding statistical value, in particular the average value, a standard deviation, and/or a median of a property of the color information of the particular data point or of the color information of multiple data points. The properties of the color information encompass in particular the intensity, color, and/or extent of the data points. Additional statistical information may be represented with little data, and therefore contributes only minimally to the total data volume. The additional information may be relevant in particular for nonselected data, since certain information about the nonselected data is still present, even if the nonselected data as a whole are no longer present.

If one of the analytes is colored with i markers in m coloring rounds, the number n of the selected color values for each data point may be equal to i or equal to i+a, where i+a is less than the total number of m coloring rounds. a is preferably an integer between 0 and 3. a is preferably determined automatically via semantics. Based on known structures in the image (cell nucleus, cell organoids, cell, cell border, cell interstice, background), the parameter a may be specifically adapted in the appropriate areas.

In conventional experiments it is common for the different analytes to each be encoded using the same number n of color values. However, an experiment may also be modified in such a way that the number of color values with which the different analytes are encoded varies. In this case, n is the maximum number of color values that are provided for encoding one of the analytes.

The image may encompass a two-dimensional image including multiple pixels as image points, or a three-dimensional image having multiple pixels as image. The images may contain time information as an additional dimension. The time information may be used not only to indicate the point in time when an individual image has been recorded, but also to represent a time series using multiple successive images, where the time information depicts the points in time of the individual images.

The number n of the selected color values is preferably not greater than one-half, and in particular not greater than one-third, of the total number of coloring rounds of an experiment. For example, n may be no greater than 10, and in particular no greater than 8, or no greater than 5.

The identification of the analytes may take place based on the selected and stored color values.

The scoring model may be a convolutional neural network (CNN), a multilayer perceptron (MLP), a transformer, a diffusion model, or a sequential model.

The color information may be stored in one of the following formats:

> For the data points, only the selected color values with and without additional information are stored.
>
> For the data points, only the selected color values, in each case together with an index that indicates from which coloring round the particular color value originates, with and without additional information are stored.
>
> The detected images are stored, the nonselected color values being set to a predetermined fill value, for example "0."

The analytes may be identified based on the selected, stored color values.

After the analytes are identified, and optionally after a manual correction, an appropriately expanded annotated data set may be created, and the processing model may be trained using the expanded annotated data set. Primarily positive examples (pixels that are based on markers) are taken into account. However, it may also be advantageous to take into account negative examples (pixels that are not based on markers) when creating the annotated data set.

Prior to the preparation of data for identifying analytes, a step of carrying out a background correction of the color values may also take place. The carrying out of the background correction includes one or more of the following:

> a rolling ball method,
>
> filtering, for example a top hat method, homomorphous filtering, low pass filtering, wherein the result of the low pass filtering is subtracted from the signal, or temporal filtering,
>
> background correction by use of an image-to-image model,
>
> background correction by use of mixed models,
>
> background correction by use of a mean shift method,
>
> background correction by use of principal component analysis,
>
> background correction by use of non-negative matrix factorization,
>
> background correction by the excitation of autofluorescence by use of at least one specific laser for all image areas of the image series, wherein the specific laser corresponds specifically to one excitation spectral range of one of the markers used, and the analytes are not yet marked with markers, or
>
> background correction by the excitation of autofluorescence by use of a nonspecific laser for all data points of the images.

As a result of the method comprising a background correction, the color values may be considered independently of the background, and thus better separated from the background. Computing effort is thus reduced, in the inference and also in the training of the model, since background contributions no longer have to be taken into account or learned.

As a result of carrying out a background correction based on a recording using a specific laser, and not yet marking the analytes with markers, the recorded background image should match particularly well the image background recorded in the coloring rounds, so that a background correction may be made in a particularly precise manner.

Additional context information that describes further properties of the sample and/or of the experiment and/or of the expected analytes may be supplied to the scoring model as input data. This context information may include in particular parameters for coloring the sample and/or the expected number of analytes or also the expected ratio of the analytes contained in the sample.

This type of context information may also be used to select a suitable scoring model from a plurality of different pretrained scoring models.

The context information may be obtained by segmentation, and in particular cell areas may be differentiated from areas that are not assigned to a cell.

According to a third aspect of the invention (aspect C), a method for preparing data for identifying analytes by coloring one or more analytes with markers in multiple coloring rounds is provided, the markers in each case being specific for a certain set of analytes. Multiple markers are detected using a camera, which for each coloring round generates at least one image containing multiple pixels and color values assigned thereto, which may contain color information of one or more markers. The color information of the particular coloring rounds is stored for evaluating same. A data point in each case includes one or more contiguous pixels in the images of the multiple coloring rounds that are assigned to the same location in a sample.

The method is characterized in that for each data point of a sample, the color value for one of m coloring rounds of an experiment is recorded in each case, and these color values in each case form a component of an output vector having the dimension m, after recording the corresponding color value the individual vector components being projected onto a projection vector having a dimension k that is smaller than m, and the projection vector for each coloring round being sequentially aggregated onto an aggregation vector having the same dimension k as the projection vector. The aggregation vector is then stored.

As a result of the output vector, having the dimension m, being projected via the projection onto an aggregation vector having the dimension k, the number of vector components is reduced from m to k. Accordingly, the data volume of the color information to be stored is also reduced. This reduction in the data volume of color information allows simple and rapid processing of the color information. The capacity of the memory device may be small compared to conventional methods, and the number of write cycles on the memory device is correspondingly reduced. Efficient, simple, and rapid processing of the color information is thus possible.

In this method, the color values are projected onto the projection vector and aggregated there not as a scalar, but, rather, as a vector component of the output vector. This method may be carried out sequentially; i.e., after each color value is detected, it is projected as a vector component onto a projection vector without having to keep all color values of an image together in a data memory. In other words, immediately after the color values are detected, they may be transferred into the dimensionally reduced space of the aggregation vector.

The projection is preferably a linear projection, and the aggregation to form the aggregation vector preferably takes place by adding the generated projection vectors to the particular aggregation vector. The projection may be a principal axis transformation or a singular value decomposition (SVD).

The projection may be estimated, for example, based on an uncompressed data set by use of singular value decomposition or principal axis transformation.

For a principal axis transformation or principal component analysis, although in principle a coordinate system is only rotated and displaced, the dimension is not reduced. However, for a principal component analysis in multidimensional space, the components are selected in such a way that their variance and thus their information content progressively decrease. The last components explain the lowest variance of the data, and may be regarded strictly as noisy data. Therefore, the last components may be omitted, as a result of which the dimension of the aggregation vector may be reduced significantly compared to the original dimension.

The method according to the invention may be carried out with all linear and nonlinear mappings that generate vector components, which explain a low variance and which thus have a low information content. Such components may be omitted without appreciably impairing the quality of the data. For these mappings, the individual components may preferably be sequentially aggregated onto an aggregation vector having a reduced dimension.

If the projection is a principal axis transformation, the bases and the transformation matrix may be generated or estimated from the following data, utilizing simulated data and also taking into account the point spread function of the microscope used:

background image, previous experiment or previous experiments, expected ideal codes, combination of background image and expected ideal codes.

Combinations of these information sources may also be used; in particular a combination of background image and expected codes is also meaningful.

The use of a principal axis transformation or a principal component analysis (PCA) also has the property that the first principal component represents the absolute brightness, which is a background signal. This is essentially of no importance for identifying the analytes. Therefore, it is possible to also omit the first principal component, thus further reducing the data volume.

In each case preferably d color values are initially recorded, which in each case form a vector component of the output vector, and the projection and the aggregation for both vector components take place together.

As a result of the projection and the aggregation taking place only after a recording of d color values, in a method in which, for example, d various color channels are examined, after an image is recorded the image is separated according to color channels, and the individual color values of the various color channels are then projected and aggregated together, as a result of which fewer projection and aggregation steps have to be carried out, which saves computing resources.

The projection may be carried out using a processing model. The processing model is in particular formed from a neural network, such as a CNN.

The processing model may have c input strings, each having d input channels, and the c input strings share k output channels, the outputs of the individual input strings in the k output channels being aggregated channel by channel, where d preferably corresponds to the number of various color channels used, and c*d=m, where m is the number of coloring rounds and c is the proportionality factor between the number of coloring rounds m and the number of color channels d used.

As a result of the projection and the aggregation taking place only after a recording of d color values, in a method in which, for example, d various color channels are examined, after an image is recorded the image is separated according to color channels, and the individual color values of the various color channels are then processed and aggregated together by the processing model, as a result of which fewer processing steps have to be carried out, which saves computing resources.

The processing model may have been trained using an annotated data set, which is supplied with one of the data points as input vectors for computing the aggregation vector, in which the ith vector element of the color values of the data point is the ith coloring round, and the remaining vector elements are 0, an objective function detecting the difference between a target output and the aggregation vectors, and the target output being computed from the input vectors using a dimensionally reducing transformation, in particular a linear or nonlinear projection, the transformed input vectors being sequentially aggregated with one another to form the aggregation vector.

The processing model may be trained separately for each input vector. The processing model may be pretrained independently of the experiment to be carried out. However, it is also possible for multiple processing models to be pretrained for different types of experiments, and for context information concerning the type of particular experiment to be used to automatically select the most suitable processing model.

The analytes may be identified based on the determined and dimensionally reduced stored color information, prior to the identification the stored aggregation vectors being back-transformed, so that the color values of the particular coloring rounds are restored in the original version.

The analytes may also be identified based on the transformed and dimensionally reduced stored color information, the series of color values that have the same projection as the recorded and stored color values, which in each case are typical for the analytes to be detected, being projected beforehand onto a particular result vector having the dimension k, and the identification of the analyte taking place based on a comparison of the aggregation vectors to the result vector for the particular data point.

In principle, it may be meaningful to subject the output vectors to a background correction prior to the projection. This applies in particular for the identification of the analytes in the transformed and dimensionally reduced space of the aggregation vectors. However, such a background correction is not necessary if the first principal component of a principal axis transformation has been omitted.

The comparison of the aggregation vector to the result vector may also be carried out using an identification processing model that has been trained using an annotated data set, which as an input data set includes aggregation vectors and result vectors of experiments in which the analytes have been identified in a conventional manner.

The aggregation vector is preferably input into an identification processing model, which as a classification network has been trained to assign the aggregation vector to a class comprising the types of analytes to be detected, or has been trained to output a result bit sequence, the result bit sequence being compared to the bit sequences that are typical in each case for the analytes to be detected in order to identify a type of analyte. The training of the identification processing model takes place using either compressed data or uncompressed data; for the latter case the compressed data would have to be back-transformed into uncompressed data by means of a back-transformation.

An identification processing model may be implemented as a classification network, for example, and trained to assign to an aggregation vector a class corresponding to its type of analyte. For this purpose, an annotated data set must be created in such a way that it includes aggregation vectors of the various types of analytes as network inputs, and as network outputs in each case includes the corresponding class of the network input being input. The assignment of the type of analyte may also take place "hard" or "soft"; i.e., the classification network either outputs exactly the assigned class, or the classification network outputs, for example, a probability distribution in which a probability is assigned to each of the possible classes that the data being input, in the present case the aggregation vectors, correspond to the particular class.

Alternatively, the identification processing model may be trained to map the input aggregation vectors onto typical bit sequences of the various types of analytes. The typical bit sequences indicate in which of the coloring rounds the particular analyte was marked with a marker. As also described above with regard to the classification network, which directly assigns a class corresponding to a type of analyte, a mapping onto typical bit sequences of the various types of analytes may also take place "hard" or "soft." For each coloring round, a likelihood is then output concerning whether or not the particular analyte was marked with a marker in the particular coloring round.

As a result of the identification processing model being trained as a classification network, a potential analyte may be assigned to a type of analyte with little computing effort.

According to a further alternative, the identification processing model may also be implemented as an embedding model. The color information, compressed or uncompressed, as well as the typical bit sequences may be input into the embedding model. The embedding model embeds the input data into an embedding space. During the training, the model parameters of the embedding models are now adapted specifically so that the embedding of the data is optimized by means of an objective function in such a way that input data that correspond to the same type of analyte or result class have the smallest possible spacing in the embedding space, and embeddings of input data that correspond to various result classes or types of analytes have the smallest possible distance from one another. In the inference, this type of training now specifically ensures that the result class or the type of analyte may be determined based on a distance of an embedding of color information from the embeddings of the typical bit sequences, in the present case the smallest distance specifically indicating the type of analyte.

An image may encompass a two-dimensional depiction including multiple pixels as image points, or a three-dimensional depiction including multiple voxels as image points, at least one pixel of each image being assignable to each data point of a sample. The images may include time information as an additional dimension. The time information may be used not only to indicate the point in time when an individual image has been recorded, but also to represent a time series including multiple successive images, the time information including the points in time of the individual images.

A data point in each case may be a pixel of each image or a group of contiguous pixels. When the color information is transformed to the dimensionally reduced aggregation vector using a processing model, it does not have to be totally clear how large the corresponding data points are. This applies in particular for fully convolutional networks. In practice, however, it has been shown that the data points often encompass no more than 10 pixels, and in particular no more than 5 pixels, in a dimension, so that the maximum pixels per data point of a two-dimensional depiction are 10×10 or 5×5 pixels, and of a three-dimensional depiction, 10×10×10 or 5×5×5 pixels.

The images may be presegmented in various semantic areas; for different semantic areas, different projections are used for transforming the output vectors to aggregation vectors.

When the different projections are principal axis transformations, they may differ in the bases and the transformation matrices.

According to a fourth aspect of the invention (aspect D), a method for preparing data for identifying analytes by coloring one or more analytes with markers in multiple coloring rounds is provided, the markers in each case being specific for a certain set of analytes. The markers are detected using a camera, which for each coloring round generates at least one image that includes multiple pixels and that may contain color information of one or more markers. The images of the particular coloring rounds are stored for evaluating the color information.

The method is characterized in that the color values determined in the individual coloring rounds are clustered, according to their intensity values, in local or global clusters with similar intensity values, and only the clustered data are stored.

By clustering the color values to form clusters with similar intensity values, the data volume of the color information is significantly reduced, since for each cluster the intensity value has to be stored only once. Similarly as for the aspects of the invention explained above, the data reduction greatly simplifies and speeds up the processing of the image data, and significantly reduces the requirements for the memory medium that is used.

After each coloring round, the intensity values are preferably reclustered as an additional feature dimension, using the newly obtained color information. The existing clusters are generally broken down into subclusters. However, if the intensity values of two neighboring clusters are very similar, it is also possible for a new cluster to arise which extends over the cluster boundary of two previously neighboring clusters. This is the case when very similar intensity values always occur in the new cluster in the subsequent coloring rounds, so that the original intensity interval is relativized.

For every pixel, a cluster ID may be stored that describes to which cluster the particular pixel belongs.

The intensity value of each coloring round may be stored for each cluster. The intensity values of the individual coloring rounds are thus stored only once for each cluster. The intensity values may therefore be stored with a high resolution without generating a large data volume. A cluster ID that is stored for each pixel may generally be encoded with significantly fewer bits than the intensity values. For example, 256 different clusters may be identified using 8 bits. More than 1000 different clusters may be encoded using 10 bits.

This type of assignment of intensity values to the particular clusters is also referred to as color palette compression. In the method according to the invention, use is made of the fact that the pieces of color information that are based on a certain marker are similar, as a result of which they may be combined in a cluster. Certain clusters thus contain the color information necessary for identifying the analytes. For the successive clusters explained above, after each coloring round a series of intensity values is assigned to each cluster. As explained in greater detail below, it may be determined from this series of intensity values whether a certain analyte is present at the location of the particular cluster.

In the method according to the invention, basically two different cluster methods may be used: the generation of local clusters, also referred to as superpixels, and the generation of global clusters. Both methods share the feature that each cluster for a coloring round is represented by only a single intensity value. For a local cluster, each cluster is made up of contiguous pixels. For a global cluster, a cluster may include multiple separate areas in an image which are spaced apart from one another.

A higher compression rate may be achieved with global clusters, since multiple separate areas in the image together form a cluster in each case, and therefore are assigned to a single, shared intensity value. For local clusters, a separate intensity value must be stored for each separate cluster region, since each cluster region forms a separate cluster. However, for a local cluster, the image position or the location of the cluster in the image has a significantly higher information content, since all pixels of the particular cluster are at least in the vicinity of this image position. For local clustering, the risk of losing so-called "rare" pixels is much lower. Rare pixels are pixels having intensity values or series of intensity values that occur only rarely in the overall image.

A sliding statistical value, in particular an average value and/or a variance and/or a median and/or a central color value, may be stored for each cluster. Since due to the clustering, the color values or intensity values are quantized to the intensity value assigned to the particular cluster for the particular coloring round, detailed information of the original image data is lost. By use of or more sliding statistical values, certain properties of the original image data may be retained without generating a large data volume. For example, for the evaluation of the clusters it may be important whether the individual pixels within a cluster are very similar, and therefore have a low variance, or whether there are significant differences between the intensity values of the individual pixels, which are reflected as an increase in the variance.

For the method explained above, the intensity values of the pixels are clustered in succession after each coloring round, so that an intensity value is assigned to each cluster for each coloring round. However, within the scope of the invention it is also possible for each image of a coloring round to be clustered separately. A significant reduction in the data volume in comparison to unclustered image data may thus be achieved as well. Within the scope of the invention, it is also possible to cluster multiple groups of coloring rounds of an experiment in succession, so that the intensity values of the coloring rounds of the respective groups of coloring rounds are assigned in each case to the clusters.

The clustering may be carried out using a partitioning, hierarchical, graph-theoretical, or optimizing cluster method.

It is also possible to carry out the clustering using a supervised or unsupervised cluster method.

It may also be advantageous to separately store the intensity values which deviate greatly, i.e., by a predetermined threshold value, from a central color value of the particular cluster, in order to generate a new cluster as needed. By maintaining intensity values that deviate greatly from the central intensity value of the particular cluster, large intensity differences are retained in a cluster, which for a clustering in subsequent coloring rounds may be the deciding factor in separating into further clusters.

If local clusters are generated, one of the image features for the clustering may be the particular intensity value, and a further image feature for the clustering may be the position of the particular pixels in the image.

An image may encompass a two-dimensional depiction including multiple pixels as image points, or may encompass a three-dimensional depiction including multiple voxels as image points, at least one pixel of each image being assignable to each measuring point of a sample. The images may include time information as an additional dimension.

Certain clusters to which the intensity values for each coloring round are assigned may be unambiguously assigned to a certain analyte, so that the analytes may be identified by reading out these clusters in question. With a low signal/noise ratio, this is easily possible without further data processing. For noisy signals, however, preparation of the data is recommended, the data being denoised in advance, for example, before they are clustered.

For identifying the analytes, the series of intensity values that are stored for the individual clusters and quantized by the clustering may also be compared to the series of target intensity values that encode the particular analytes. The target intensity values are preferably quantized beforehand to the same value range as the clusters. For clusters, as briefly explained above, the intensity values of all pixels of the cluster are set to a central color value or a central intensity value. These central intensity values of the clusters form the value range. If an intensity value is assigned in each case to the clusters for each coloring round, the multiple central intensity values of the individual coloring rounds form the quantized value range of the cluster for the particular cluster.

The identification of the analytes based on the clusters may be carried out using a processing model. This processing model is preferably a classification model.

The clustering itself may also be carried out using a processing model. Such a processing model for the clustering is preferably a segmentation model and in particular is a semantic segmentation model.

Additional context information that describes further properties of the sample and/or of the experiment and/or of the expected analytes may be supplied as input data to the processing model. These pieces of context information are in particular parameters for coloring the sample and/or the expected number of analytes, or also the expected ratio of the analytes contained in the sample. The quantization of the clustering may be set based on this context information; i.e., the central intensity values for the particular coloring rounds are thus determined and assigned to the particular clusters.

According to a fifth aspect of the invention (aspect E), a method for preparing data for identifying analytes by coloring one or more analytes with markers in multiple coloring rounds is provided, the markers in each case being specific for a certain set of analytes. The markers are detected using a camera, which for each coloring round detects at least one image that may contain color information of one or more markers. The color information of the particular coloring rounds is stored for evaluating the color information.

The method is characterized in that the images are subdivided into quantization regions in which the intensity values of the pixels are encoded with a different quantization in each case, and the quantized intensity values of the pixels are stored as color information.

A quantization means that the intensity values in the different quantization regions have different value ranges, generally with a reduced number of intensity values compared to the original representation of the intensity values after the images are detected with the camera. This means that the different quantization regions are encoded with different bit depths; i.e., a different number of bits then represents the particular intensity value.

The intensity values of the image originally recorded with the camera have a predetermined bit depth of 16 bits, for example, in a certain color channel. In other words, the brightness range of this color from maximum dark to maximum bright is uniformly encoded using 16 bits. The quantization regions generally include only a portion of the brightness range, and this portion of the brightness range is quantized with a predetermined bit depth. For dark areas, for example, which only represent background, this bit depth may be a few bits. For areas of average brightness that contain a very large amount of information since a majority of the signals of markers occur in these areas, whose difference from the background is often only very low, the original bit depth of 16 bits is retained in this intensity range. In the bright areas, in which the marker signals, also referred to as colored signals, often differ greatly from the nonmarker signals, also referred to as uncolored signals, it is sufficient to encode the intensity values with a smaller bit depth of 8 bits, for example, to allow the intensity values of the colored signals to be reliably distinguished from the intensity values of the uncolored signals. The selection of the suitable quantization regions also depends on the particular experiment, and in particular the dyes used and the background image that is present in each case.

The bit depth of a quantization, i.e., the number of bits with which the intensity values are encoded, is smaller, at least for certain quantization regions, than the number of bits with which the intensity values detected by the camera are encoded by the camera.

Different bit depths may also be applied in the different quantization regions.

The quantization regions may be divided according to one or more of the following method steps:

The quantization regions are established beforehand via intensity limits, so that each quantization region corresponds to a certain intensity range.

The images are semantically divided into different quantization regions.

The frequency of the individual intensity values is detected, and the quantization regions are established via intensity limits situated around frequency peaks.

The quantization regions are established by clustering similar intensity values.

The quantization regions are established by semantic segmentation of the images, for example in the background, cell, and cell nucleus.

A combination of several of the method steps explained above may also be used to determine the quantization regions.

The quantization regions may be divided at the following points in time:

once before the first quantization of one of the images, the division of the quantization regions preferably being carried out using a background image that is generated without markers, after the first coloring round, the quantization regions being divided based on a portion of the image detected during the first coloring round or based on the overall image, after multiple coloring rounds in each case, the quantization regions being divided based on a portion of the image detected during the particular coloring round or based on the overall image, or after each coloring round, the quantization regions being divided based on a portion of the image detected during the particular coloring round or based on the overall image.

Accordingly, it is also possible for the quantization regions to be initially divided after the first coloring round, and later redivided after several coloring rounds. A repeated division or determination of the quantization regions may take place in each case after the same number of coloring rounds, or also after unequal numbers of coloring rounds.

The areas of the image that are particularly suitable for dividing the quantization regions may be automatically determined, in particular based on areas that include multiple different quantization regions.

Three quantization regions may be used, each of which forms different intensity ranges, wherein the intensity range with average intensity values is finely quantized, the intensity range with bright intensity values is quantized more roughly than the intensity range with average intensity values, and the intensity range with bright intensity values is preferably quantized more finely than the intensity range with dark intensity values. The intensity range with dark intensity values is consequently the most roughly quantized intensity range.

The intensity range with dark intensity values may correspond to a dark background. Its intensity values are often not relevant for identifying the analytes, and therefore may be quantized very roughly or even discarded altogether.

The intensity range with average intensity values may correspond to the cell areas, which should be quantized very finely due to the relevance of small intensity differences for the analyte identification.

The intensity range with bright intensity values depicts bright points in the cells that have very high intensity values. Although these are very relevant for the analyte identification, due to great brightness differences they often stand out markedly from the intensity values that are not relevant for identifying the analytes. Therefore, a rougher quantization, i.e., with a smaller bit depth than in the mid-intensity range, is possible.

An image may encompass a two-dimensional depiction including multiple pixels as image points, or may encompass a three-dimensional depiction including multiple voxels as image points, at least one pixel of each image being assignable to each measuring point of a sample. The images may include time information as an additional dimension.

For identifying the analytes, the stored quantized series of intensity values are compared to the series of target intensity values that encode the particular analyte.

Prior to the comparison, the target intensity values that encode the analytes may be quantized in the same way as for the detected color information. Alternatively, also prior to the comparison, the quantization of the stored quantized series of intensity values may be eliminated to allow a comparison of the intensity values to the target intensity values that encode the analytes. An exact back-transformation is not always possible, since information may be lost due to the quantization. The elimination of the quantization also means a transformation in a value range that corresponds to the value range of the originally measured intensity values. For this purpose, it may be advantageous when even further context information is present in addition to the quantized intensity values.

According to one alternative, the stored color information may also be directly binarized and then compared to binarized target bit sequences of a codebook of the experiment.

According to the present invention, a codebook includes, for each type of analyte, a series of markers which in the particular coloring rounds couple to the particular type of analyte.

According to a sixth aspect of the invention (aspect F), a method for preparing data for identifying analytes in a sample is provided, one or more analytes being colored with markers in multiple coloring rounds in an experiment. The markers in each case are specific for a certain set of analytes, the markers being detected using a camera, which for each coloring round generates at least one image that may contain color information of one or more markers. The color information of the particular coloring rounds is stored for the evaluation.

The method is characterized in that for an nth coloring round, an expected predicted image is predicted based on predicted image data of one or more preceding coloring rounds and/or based on predicted image data of the present coloring round, and a difference image is formed on the one hand from an actually detected image or from an actually detected image plane of the present coloring round, and on the other hand is formed from the predicted image, the difference image being stored as color information.

Since many pixels of the actually detected image or of the actually detected image plane and of the predicted image are generally the same, the difference image contains many pixels having the difference value "0." Such images may be stored with very high compression. It is also possible to store only the difference between the two images, i.e., to store the pixels having a difference value that is different from "0." The data volume is also significantly reduced in this way.

A reduction in the data volume of the image data to be stored greatly simplifies and speeds up the write and read operations, and also reduces the number of accesses to the memory medium, thus prolonging its service life.

The prediction of the predicted image data is carried out using a method that is unambiguous and reversible, so that based on the difference image, it is possible at any time to restore the actually detected image or the actually detected image plane when the image or the image plane from which the predicted image data have been created is known. In this way, all actually detected images or image planes may be reconstructed without data loss. The first image is preferably stored in uncompressed form, or in compressed form using a compression method that is independent of the present aspect, so that the first image, which is referenced by the further images by use of the difference image or the difference images, is completely available.

The predicted image may correspond to an image plane of a Z image made up of multiple image planes, and the predicted image data may include one or more image planes of Z images made up of one or more preceding coloring rounds and/or one or more image planes of the Z image of the present coloring round. Thus, for three-dimensional image data with multiple image planes, the prediction may proceed from an image plane of a preceding coloring round, or also from an image plane of a present coloring round.

The preceding coloring rounds may be coloring rounds of the same experiment, or coloring rounds of a different experiment with preferably a similar or identical sample. The more similar the sample and the particular state of the sample during the experiment for the preceding coloring round are to the present coloring round, generally the better is the agreement of the predicted image data with the actually detected image or the actually detected image plane.

The predicted image data may include subsets of the images of one or more preceding coloring rounds and/or of the present coloring round, wherein the subsets may be individual or multiple image planes of a Z image, or also excerpts in a plane of the images. These excerpts may be excerpts of two-dimensional images, or also excerpts of image planes of a Z image.

The predicted image data may be reconstructed image data from difference images, or only the difference images themselves from preceding coloring rounds. In other words, a prediction may also be made based on the compressed image data in the form of difference images. Accordingly, the predicted image data may be kept in compressed form.

The predicted image data may originate solely from the immediately preceding coloring round and/or from the present coloring round. The predicted image data that originate from a present coloring round are image planes of a Z image, on the basis of which other image planes are predicted or forecast.

The difference image is preferably compressed before being stored. As explained above, the compression of such difference images is generally very effective.

The predictions are carried out using a predictor, in particular a linear predictor. The predictor is preferably designed in such a way that it makes an unambiguous assignment from the output image data to the predicted image data, so that based on the predicted image data, the output image data may at any time be unambiguously recreated without loss of information.

The predictions may be carried out using a processing model of a machine learning system. For this purpose, in particular a neural network is suitable for the image-to-image regression.

The processing model may be retrained for each coloring round, or retrained for each experiment, or selected from multiple pretrained processing models, this selection preferably being made based on context information. This context information may be properties of the sample and/or of the experiment and/or of the expected analytes, and the context information may include in particular parameters for coloring the sample and/or the expected number of analytes or also the expected ratio of the analytes contained in the sample.

The processing model may have been trained using annotated training data, the annotated training data in each case including an output image and a corresponding target image, the output image as well as the target image having been measured for a sample.

The output image may originate from a previous coloring round, and the target image may originate from a subsequent coloring round. However, the output image may also be an image plane of a three-dimensional Z image, and the target image may be a different image plane of the same three-dimensional Z image.

The predicted image data may be normalized prior to the prediction, for example to have a predetermined intensity range and/or a defined background signal.

The predicted image data may be denoised prior to the prediction. Such denoising may be carried out using different methods, which include conventional methods (filtering/BM3D) as well as machine learning methods (NOISE2NOISE/NOISE2VOID).

An image may encompass a two-dimensional depiction including multiple pixels as image points, or may encompass a three-dimensional depiction including multiple voxels as image points, the three-dimensional depiction generally being generated via multiple image planes of a Z image. The images may include time information as an additional dimension.

For identifying the analytes by use of the stored difference images, the actually detected image or the actually detected image plane may be restored from same, at least for predetermined data points, wherein a data point in each case includes one or more contiguous pixels in the images of the multiple coloring rounds that are assigned to the same location in a sample.

In the identification of the analytes, the reconstruction of the detected images or of the detected image planes may take place pixel-by-pixel or data point-by-data point, or also over the entire image.

The analytes may be nucleic acid sequences, and the markers may in each case include an oligonucleotide sequence and a dye molecule coupled thereto.

The context information may include, for example, a sliding statistical value, in particular an average value and/or a variance and/or a median and/or a central color value.

The analytes may be nucleotide sequences, and the markers may in each case include an oligonucleotide sequence and a dye molecule coupled thereto.

According to a seventh aspect of the invention (aspect G), a method for preparing data for identifying analytes by coloring one or more analytes with markers in multiple coloring rounds is provided, the markers in each case being specific for a certain set of analytes. The markers are detected using a camera, which for each coloring round generates at least one image that includes multiple pixels to which a color value is assigned in each case as color information, and includes colored signals and uncolored signals. A colored signal is a pixel containing color information of a marker, and an uncolored signal is a pixel containing color information that is not based on a marker. The color information of the particular coloring rounds is stored for evaluating same, and a data point in each case includes one or more contiguous pixels in the images of the multiple coloring rounds that are assigned to the same location in a sample.

The method is characterized in that the color values of the pixels of the images of a sample are subjected to an assessment of whether they represent a colored signal and/or an uncolored signal, and the pixels, whose color values are assessed with a predetermined likelihood that they are a colored signal or an uncolored signal, are correspondingly binarized, and when the color information is stored, a corresponding binary value is stored for these binarized pixels instead of the color values.

The binary value is a single-digit binary number. The data volume may be significantly reduced by reducing the color values to binary values, thus achieving the above-mentioned advantages of easier and faster processing and the low demands on the memory medium.

For color values that are not binarized, the particular measured color values are stored.

A color value that is unbinarized according to an assessment may be reassessed in a subsequent assessment, and binarized if it then meets the desired criteria. It is thus possible to then carry out a recompression from earlier assessment rounds. After each coloring round or in each case after a predetermined number of coloring rounds, the pixels may be subjected to the assessment. If the assessment is not carried out until after several coloring rounds, it is advantageous to at least assess the pixels of all coloring rounds that have not previously been assessed.

The assessment of the color values may be based on one or more of the following values:

a color value that is to be assessed,
one or more color values of one or more preceding coloring rounds, statistical values of the measured color values of the coloring rounds previously carried out,
one or more color values of background images, and/or statistical values for the background.

The assessment may also take place based on a combination of the data listed above.

It may be determined whether the color value with a predetermined likelihood represents a colored signal or an uncolored signal by use of a measure of confidence or heuristics.

The color values may be assessed using a scoring model of a machine learning system, the scoring model learning criteria for assessing the color values for whether they represent, with a certain likelihood, a colored signal and/or an uncolored signal. The scoring model may have been trained using an annotated data set, which as an input data set contains the color values of the pixels and corresponding target outputs, wherein the target outputs for each color value individually define whether it represents a colored signal or an uncolored signal.

The scoring model may have been trained using an annotated data set, which as an input data set contains the color values of the pixels and corresponding target outputs, which in each case define whether the color values represent a colored signal or an uncolored signal, or whether it cannot be determined if they represent a colored signal or an uncolored signal.

The scoring model is preferably a classifier. According to the above discussion, the classifier may be trained on the one hand with regard to a target output "colored signal" or "uncolored signal," or on the other hand, with regard to the target output "colored signal" or "uncolored signal" or an undeterminable signal. In the first case, the classifier is uncertain when a class likelihood is near the decision limit of 0.5. However, the classifier may also be trained in a targeted manner in such a way that a third class or higher-level class is introduced which states that a decision cannot be made.

The annotated data set may also be created using a method in which the color values of the multiple coloring rounds are evaluated in unbinarized form as to whether they represent a colored signal or an uncolored signal. During the training, for each coloring round the color values that represent a colored signal or uncolored signal are entered as input into the scoring model and an objective function is computed. The objective function detects a difference between the assessments, output by the scoring model, that the color values represent a colored signal or uncolored signal, and detects the annotations of the color values of the annotated data set, which indicate whether the color values specifically represent a colored signal or an uncolored signal. Lastly, the objective function is optimized by adapting the model parameters.

During a training, for each coloring round the color values that represent a colored signal or uncolored signal may be entered as input into the scoring model, partly as measured color values and partly as binary values. In this way the model is trained using the originally measured values and also using compressed binary values, so that the model learns how to handle a mixture of actual measured values and binary values as input values.

The annotated data set may have been generated via one or more of the following steps:

simulating signals of the various markers, using a representative background image and a known point spread function of a microscope, generating the annotated data set by use of a generative model that has been trained on comparable data, recording reference images that include at least one background image, and for each of the background images for each type of analyte, recording at least one image in which analytes of the particular type of analyte are marked, carrying out a conventional method for spatial identification of analytes, recording a representative background image and subtracting, pixel by pixel, the image signals of the representative background image from the image signals of the images series on which the annotated data set is based, before providing the annotated data set, so that the annotated data set includes only background-corrected color values, and/or obtaining the annotated data set based on a portion of an experiment, so that the trained processing model may be applied to the remaining portion of the experiment. The annotated data set may thus be created using different methods.

In addition to the particular color value, further context information may be input to the scoring model for the assessment of the color values, which preferably includes the following data:

a color value of the particular pixel of the preceding coloring round, statistical values of the coloring rounds previously carried out, one or more color values of background images, and/or statistical values for the background, and/or the number of expected analytes per experiment or per color channel, the codebook used, and/or a user ID.

Further suitable context information that may be input into the scoring model for the assessment of the color values includes statistical information concerning all color values of a particular data point and/or concerning the nonselected color values of one of the data points and/or concerning the selected color values of one of the data points, for example information concerning a coloring round (number; point in time; etc.) and/or a sliding average value, a standard deviation, a variance, and/or a median of a property of the color information of the particular data point or of the color information of multiple data points. Among the properties of the color information, in particular the brightness, color, and/or extent are/is relevant.

The context information may be obtained by segmentation, and in particular cell areas may be differentiated from areas that are not assigned to a cell.

The image may encompass a two-dimensional image including multiple pixels as image points, or a three-dimensional image having multiple voxels as image points, and the images may contain time information as an additional dimension.

The identification of the analytes may take place based on the stored color values, and in part based on the binarized color values. During identification of the analytes, measured and binarized values may be used in parallel.

The scoring model may be a convolutional neural network (CNN), multilayer perceptron (MLP), a transformer network, or a sequential model, for example a recurrent neural network (RNN).

The analytes may be identified based on the stored color information, and after the analytes are identified, and optionally after a manual correction, an appropriately expanded annotated data set may be created, and the processing model may be trained using the expanded annotated data set. Continuous, supervised learning is thus possible.

The method may also include, prior to the preparation of data for identifying analytes, a step of correcting the image signals of the image series based on a background signal, the background image signal being determined, for example, using a rolling ball method, a top hat method, and/or by the excitation of autofluorescence by use of a nonspecific laser for all pixels.

When a minimum number of the color values of a data point has been binarized, a comparison with a codebook may take place, based on the binarized color values and the unbinarized color values of the data points, in order to improve the assessment of previously unbinarized color values.

The comparison may take place via matrix multiplication of a color value vector by a codebook matrix, the codebook matrix including a target bit sequence for each analyte to be identified, and the color value vector for the binarized color values and for the unbinarized color values including a likelihood value, corresponding to the assessment, between 0 and 1, and the target bit sequences being determined based on a result vector of the matrix multiplication that best fits the color vector, and the unbinarized color values being binarized based on the determined target bit sequences.

A method for training a machine learning system using a scoring model may also be provided, in which the scoring model has been trained in particular to carry out the method according to one of the above explanations.

The analytes may be nucleic acid sequences, and the markers may in each case include an oligonucleotide sequence and a dye molecule coupled thereto.

The different aspects of the invention (aspects A-G) explained above may be used individually or in any combinations with one another. Several preferred combinations are explained below by way of example: In a combination of aspects A and B, the data points of the images which based on the assessment are reliably not candidate data points are eliminated, and at the same time, for each candidate data point only n color values of the different coloring rounds that most likely represent a colored signal are selected. For this purpose, for example a scoring model is trained to decide, based on the color values selected according to aspect B, whether the data point is not a candidate data point and therefore may be eliminated.

In the combination of aspects A and D, for each cluster a scoring model may decide whether a cluster belongs to the background and all data points in the particular clusters may be discarded. This applies for local as well as global clusters.

In the combination of aspects B and D, clustering is carried out in which only the color values for the particular clusters selected according to aspect B are retained.

In a combination of aspects A, B, and D, clustering is carried out in which for the individual clusters, only the color values selected according to aspect B are retained, and by use of a scoring model it is decided whether a cluster belongs to the background and all data points of the cluster may be discarded. This applies for local as well as global clusters.

A combination of aspects A, B, C, D, E, and F is also advantageous. Clustering is carried out according to aspect D (local or global clustering). For the individual clusters, only the color values selected according to aspect B are assigned to the individual clusters, these color values being projected onto a projection vector having a reduced dimension according to aspect C. In addition, according to the scoring model of aspect A it may be decided whether clusters belong to the background and all data points of this cluster may be discarded. As a function of predetermined quantization regions or as a function of the location of the data points, in each case a special or individual quantization according to aspect E may be applied thereto. The memory requirements may then be further reduced by rounds of compression according to aspect F.

According to the present invention, pixels of the background, i.e., background pixels, may be divided into various types of background pixels. On the one hand there are background pixels, so-called analyte-free background pixels, in which no analytes can be located from the outset, for example because no cells with analytes are present at the locations in the sample. On the other hand, there are also background pixels at which analytes may potentially be present, but which have not been found or detected in the present sample. These pixels may also be referred to as analyte background pixels. The color information of background pixels is also referred to as background signals, regardless of whether they are analyte background pixels or analyte-free background pixels. For the training, data points with background signals of background pixels may also be incorporated into the annotated data set.

According to one alternative, the analyte-free background pixels may be excluded from the analysis from the outset based on the semantics, for example via semantic segmentation of the images.

Similarly, an annotated data set may also be designed in such a way that training data points of background pixels are specifically data points of the analyte background pixels.

BRIEF DESCRIPTION OF THE FIGURES

The invention is explained in greater detail below based on the examples illustrated in the drawings.

The drawings schematically show the following:

FIGS. 3a, 3b, 3c show excerpts of microscopic images and a corresponding result output, an analyte and markers coupled thereto, and the code words of three relevant data points.

DETAILED DESCRIPTION OF THE EMBODIMENTS

Figure 1:
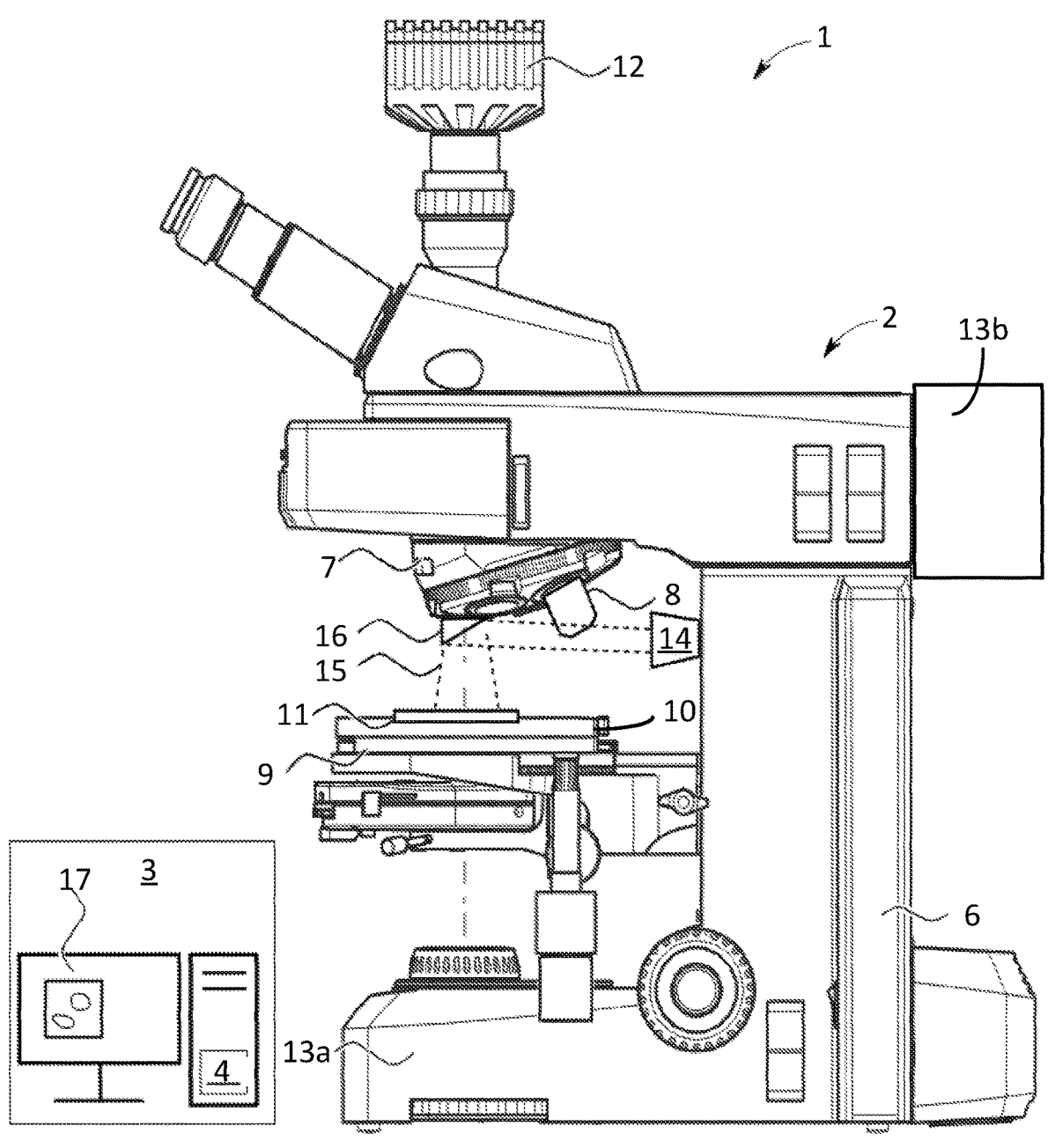
FIG. 1 shows a system for identifying analytes in samples according to one embodiment.
Figure 2:
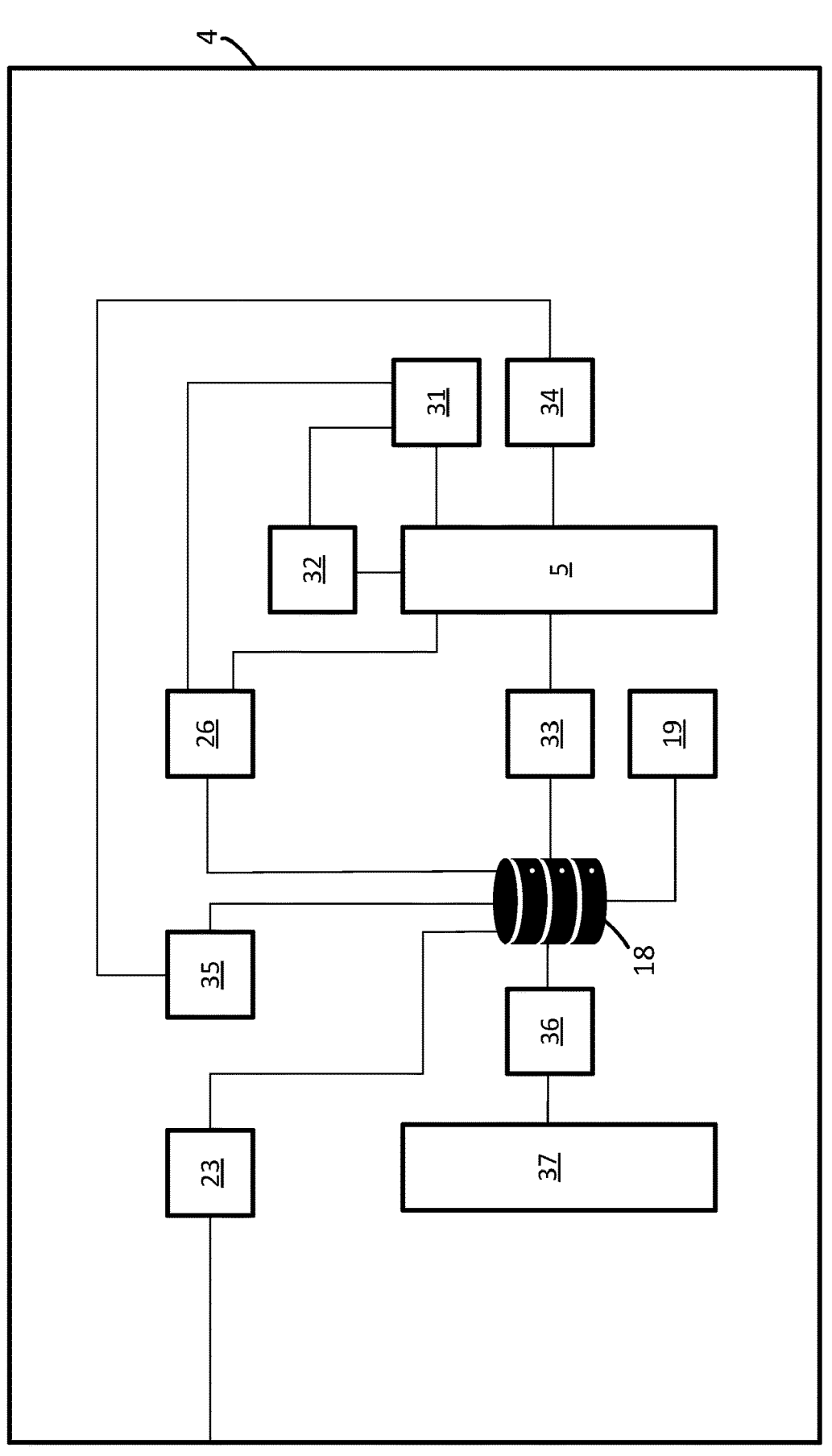
FIG. 2 shows an evaluation unit of the system from FIG. 1 in a block diagram.
Figure 4:
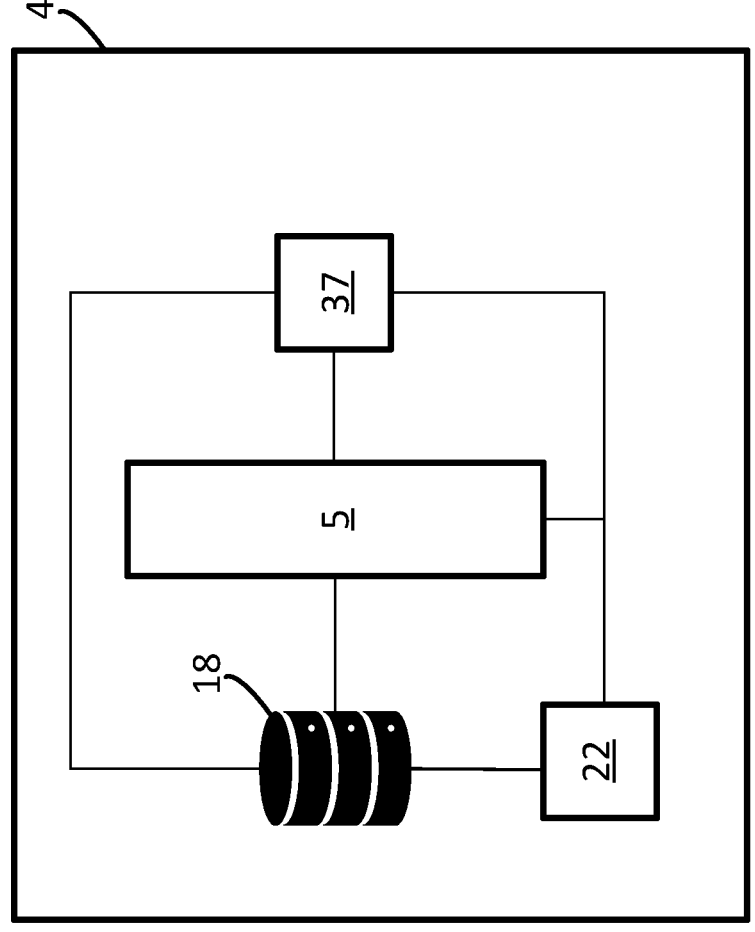
FIG. 4 shows an evaluation unit of the system from FIG. 1 in a block diagram according to a further embodiment.

One exemplary embodiment (aspect A) of a machine learning system 1 comprises a microscope 2, a control device 3, and an evaluation unit 4 (FIG. 1). The microscope 2 is communicatively coupled (i.e., via a hard-wired or wireless data line) to the evaluation unit 4. The evaluation unit 4 includes a processing model 5 for compressing the image data (FIG. 2). The processing model may also be referred to as a compression processing model 5.

The microscope 2 is an optical microscope. The microscope 2 includes a stand 6 which includes further microscope components. The further microscope components are in particular an objective changer or objective revolver 7 with a mounted objective 8, a sample stage 9 with a mounting frame 10 for holding a sample carrier 11, and a microscope camera 12. When a sample is fixed into the sample carrier 11 and the objective 8 is swiveled into the microscope beam path, and an illumination device 13a illuminates the sample in the transmitted light, or excitation lighting 13b illuminates the sample in the incident light, the microscope camera 12 receives detection light from the fixed sample and may record a microscopic image 24. Samples may be any given objects, fluids, or structures. The excitation lighting 13b is preferably designed for exciting certain fluorescent dyes.

The recorded microscopic image 24 is a two-dimensional image containing pixels arranged in rows and columns. The microscopic image 24 is an optical depiction of the sample in a focal plane of the microscope 2. Multiple microscopic images 24 which differ slightly in each case in the arrangement of the focal plane with respect to the sample may be combined to form a three-dimensional image, the pixels of the three-dimensional image forming voxels. In the following discussion, the expression "microscopic image" 24 is understood to mean a two-dimensional image as well as a three-dimensional image, also referred to as a Z image or image stack. Accordingly, the detection of a microscopic image 24 means the detection of a two-dimensional microscopic image 24 as well as the detection of a three-dimensional microscopic image 24.

The microscope 2 optionally includes an overview camera 14 with which overview images of a sample environment may be recorded. The overview images show the sample carrier 11, for example. A visual field 15 of the overview camera 14 is larger than a visual field 15 for recording a microscopic image 24. The overview camera 14 views the sample carrier 11 by means of a mirror 16. The mirror 16 is situated at the objective revolver 7, and may be selected instead of the objective 8.

According to this embodiment, the control device 3, as schematically illustrated in FIG. 1, includes a screen 17 and the evaluation unit 4. The control device 3 is configured to control the microscope 2 for recording microscopic images 24, and to store microscopic images 24 recorded by the microscope camera 12 on a memory module 18 (FIG. 2) of the evaluation unit 4, and to display the microscopic images on the screen 17. The recorded microscopic images 24 are then further processed by the evaluation unit 4.

The evaluation unit 4 also stores training data, for training the processing models 5, in the memory module 18. The training data include an annotated data set.

The annotated data set for the processing model 5 includes microscopic images 24 or the pixels thereof as input data, and a target output that defines a foreground and/or background of the particular pixel or image. The data points, which are candidate data points, belong to the foreground.

In the present exemplary embodiment, the input data or input tensors are microscopic images 24 or the pixels thereof of a predetermined sample, and the target outputs are the particular descriptions of the corresponding foreground and/or background. The target outputs may be microscopic images 24, the locations of the markers being marked in the images. In all microscopic images 24, all potential locations of markers (all candidate data points) may be marked, or only the markers that are present in the particular microscopic images 24 may be marked. When all potential locations of markers are marked, each annotated microscopic image 24 contains the same pattern of locations for markers. In contrast, if the markers actually present are marked, the individual annotated microscopic images 24 then generally have different patterns of locations for markers. The patterns of the locations of the markers alone are sufficient as annotated data, so that the corresponding microscopic images 24 may also be omitted; however, in practice it is easier to provide existing microscopic images 24 with markings for the locations of the markers in order to thus generate the annotated data.

The present exemplary embodiment is a machine learning system 1, which upon identification of analytes contained in a sample of an experiment reduces the data volume of color information of the images 24 of multiple coloring rounds during the evaluation operation by use of the processing model 5.

In an experiment, an attempt is made to simultaneously identify different analytes in a sample in a method. For this purpose, the analytes are successively marked with markers in multiple coloring rounds. After the particular coloring rounds, the markers are removed, so that in subsequent coloring rounds analytes may be re-marked with a further marker using the same or similar dye. Thus, the markers do not have to be removed immediately after each coloring round, but, rather, only when further markers are to be used with the same dye.

Each marker is specific for a certain set or genuine subset of all possible detectable analytes. A marker is generally specific for multiple analytes. A different marker is used in each coloring round, so that in each case different analytes are marked. Since a marker can generally couple to several different analytes, it is not specific for a certain analyte. However, for multiple coloring rounds made up of the series of markers that have been coupled to an analyte, it may be deduced which analyte is involved, so that it may be unambiguously identified.

All series of markers that are specific for an analyte form a codebook. That is, for each type of analyte a codebook includes a series of markers that couple to the particular type of analyte in the particular coloring rounds.

Since not every analyte in a coloring round has to be marked with a marker, with multiple coloring rounds, for each analyte a series of marked and unmarked states may result, which may also be represented as a colored signal and an uncolored signal, as true and false, or by "0" and "1."

The markers generally contain a dye, in particular a fluorescent dye, which may be detected in the sample using the microscope 2. The markers may be made up of an individual molecule. However, the markers may also be made up of several molecules, as disclosed in WO 2020/254519 A1 and WO 2021/255244 A1, for example.

It is also possible to use markers with different dyes. Markers with different dyes may be simultaneously brought into contact with the sample, and also simultaneously or sequentially recorded with the microscope 2. If markers are simultaneously used with different dyes, multiple coloring rounds within the meaning of the present invention may be simultaneously carried out, since the marking of analytes with different markers in each case represents a coloring round.

When multiple coloring rounds are carried out simultaneously, the markers with different dyes may be excited separately, a separate microscopic image 24 then being recorded for each type of marker. Each of these microscopic images 24 contains the color information of a coloring round. It is also possible to excite the dyes over a broad band when the sample simultaneously contains markers with different dyes, so that multiple markers with different dyes simultaneously illuminate. The simultaneously excited markers are detected via a microscopic image 24 which thus contains color information of multiple coloring rounds, which may be separated in the subsequent analysis by filtering the different colors. The spectral ranges, which in each case include a color of a marker, are also referred to as color channels. The images separated into the color channels are monochromatic images, and for each pixel contain, as a color value, an intensity value or an intensity of the pixel in the color of the color channel.

The analytes may be nucleic acid sequences. Such experiments using nucleic acid sequences are set forth in EP 2 992 115 B1, for example. However, the invention is not limited to nucleic acid sequences, but instead is suitable for all experiments in which analytes are successively marked with different markers which in each case are specific for a subset of the potentially detectable analytes. Thus, for example, proteins may also represent analytes, as is known from WO 2020/254519 A1 and WO 2021/255244 A1.

According to the present invention, an analyte is an entity whose presence or absence in a sample is to be specifically verified, and which is to be encoded if it is present. This may involve any type of entity, including a protein, a polypeptide, a protein, or a nucleic acid molecule (RNA, PNA, or DNA, for example), also referred to as a transcript. The analyte provides at least one site for specific binding with analyte-specific probes. Within the meaning of the invention, an analyte may also comprise a complex of objects, for example at least two individual nucleic acid, protein, or peptide molecules. In one embodiment of the disclosure, an analyte does not include a chromosome. In another embodiment of the disclosure, an analyte does not include DNA. In some embodiments, an analyte may be an encoding sequence, a structural nucleotide sequence, or a structural nucleic acid molecule that relates to a nucleotide sequence that is translated into a polypeptide, generally via mRNA, when it is under the control of suitable regulatory sequences. The boundaries of the encoding sequence are determined by a translation start codon at the 5' terminus and a translation stop codon at the 3' terminus. An encoding sequence may include genomic DNA, cDNA, EST, and recombinant nucleotide sequences, but is not limited thereto. Such methods are referred to as spatial transcriptomics or also multiomics, for example, depending on the type of analyte that is to be identified.

The generated microscopic images 24 contain color information which originates in part from markers that are coupled to analytes. This color information, generated by the markers coupled to the analytes, is the information that is to be evaluated in order to identify the individual analytes. To allow this color information of the different generated microscopic images 24, which is influenced by the markers, to be assigned in each case to the corresponding analytes, the microscopic images 24 of the different coloring rounds must be precisely registered with one another. This may be carried out, for example, in such a way that in the individual microscopic images 24, landmarks or prominent points are identified which repeat in the successive generated microscopic images 24. These may be bright points, for example, which are distributed to the greatest extent possible over the entire sample. These points form a registration pattern. Such a registration pattern is a two-dimensional pattern for a two-dimensional image, and for a three-dimensional image is a 3D point cloud.

During registration, the microscopic image 24 generated after each coloring round is registered with the microscopic image 24 of the first coloring round or one of the preceding coloring rounds, based on its registration pattern, i.e., brought into conformity by bringing the registration patterns of the two images into congruence. This may be carried out using the iterative closest point algorithm, for example.

After the result microscopic images are registered with one another, a coordinate system is assigned to each result microscopic image, the coordinate systems of the different result microscopic images being brought into congruence with one another. This means that with a correct registration, the particular analytes are present at positions that are described in the different images by the same or essentially the same coordinates. It is thus possible to assign color values of the different result microscopic images to the same analytes in each case.

In addition to the processing model 5 and the memory module 18, the evaluation unit 4 includes further modules that exchange data via channels 20. The channels 20 are logical data links between the individual modules. The modules may be designed as software modules or hardware modules.

A microscopic image registration module 19 is directly connected to the memory module 18, and registers the microscopic images 24 that are detected with the microscope 2 (FIG. 2).

The evaluation unit 4 includes a training data supply module 26 which reads out the annotated data set from the memory module 18 and inputs it into the processing model 5. The annotated data set includes microscopic images 24 and in each case a corresponding target output 21 (FIG. 3), via which the foreground or the pixels of the microscopic images 24 that belong to a candidate data point is/are defined. The training data supply module 26 is used to supply the microscopic images 24 of the annotated data set to the input side of the processing model 5, and to supply the target output 21 to the output side of the processing model 5 via an objective function module 31.

In the present exemplary embodiment, the processing model 5 is a convolutional neural network (CNN) with an input layer, multiple intermediate layers, and an output layer. The processing model 5 is also referred to below as a scoring model 5, since it assesses the pixels of the microscopic images 24, generated in the different coloring rounds, for whether they contain color information (foreground) that is relevant, or color information (background) that is not relevant, for the evaluation. The candidate data points contain color information of markers for some but not all coloring rounds, and the background data points are data points which normally contain color information of a marker when there is not a single coloring round, or when there are fewer coloring rounds than defined by a predetermined threshold value. This predetermined threshold value is smaller than the number of different markers necessary for identifying an analyte.

By use of the scoring model, the aim is to establish, after the fewest possible coloring rounds, which data points are relevant and whether their color information is therefore to be stored, and which data points are not relevant, so that their color information may be ignored and accordingly does not have to be stored.

The assessment of the data points may either take place individually for each data point, for which it is said that the receptive field of the processing model 5 then contains only a single data point, or alternatively the receptive field of the processing model 5 may also include neighboring data points of the data point to be assessed. The processing model 5 then assesses the particular data point based, among other things, on the color information of the further data points in the receptive field, as well as the color information of the particular data point. It is also said that the spatial context is incorporated into the assessment of the color information of the data point, in the present case, specifically the color information of the neighboring data points that belong to the receptive field of the processing model 5.

The number of image areas in the receptive field may be selected, for example based on the point spread function of the microscope 2, in such a way that a diameter of the receptive field is not greater than, or is only marginally greater than, or for example is twice as great as, a diameter of a region onto which a point in a sample is mapped based on the point spread function. For example, the size of the receptive field is 3×3, 5×5, 7×7, 9×9,13×13, or 17×17 data points; however, the size of the receptive field may also be 3×3×3, 5×5×5, 7×7×7, 9×9×9,13×13×13, or 17×17×17 data points when Z images are recorded in the coloring rounds.

If the spatial context is incorporated into the assessment of a data point, color information of data points that are classified by the processing model 5 as eliminatable may be eliminated only when these data points are no longer needed as spatial context for assessing the neighboring data points. This is the case, for example, when all data points in the spatial context are already classified as eliminatable, or when all data points in the spatial context have been unambiguously classified as candidate data points or as eliminatable. That is, for processing models 5 into which the spatial context of the data points is incorporated in the assessment of same, the assessment that a data point is reliably not a candidate data point also always includes that the color information of the data points to be eliminated is no longer relevant for assessing the remaining data points yet to be assessed, to the spatial context of which the data points contribute.

Unless stated otherwise below, the scoring model includes multiple scoring submodels which in each case form a processing model 5 for an individual coloring round. Unless stated otherwise, the scoring submodels of a scoring model have essentially the same or similar design. During the training and also during the inference, for an nth coloring round, for each submodel all or at least some of the microscopic images 24 generated in the first through nth coloring round are generally supplied to the processing model 5 as input data. The generated microscopic images 24 may be reconstructed for supplying to a scoring submodel of a subsequent coloring round, or in the stored compressed form, also supplied to the scoring submodel of a subsequent coloring round. The scoring submodels are to be trained accordingly.

Alternatively, the processing model 5 may also be formed from a multilayer perceptron (MLP) or a diffusion model or a recurrent neural network (RNN).

However, the processing model 5 may also be a transformer network.

Alternatively, the processing model 5 may also be merely a single model, the model including its own input channels for each coloring round, and the input channels of coloring rounds not yet recorded being filled with zeroes.

The objective function module 31 receives the result output 30 from the processing model 5 and computes from same and the target output 21 an objective function. The objective function describes the distance of the result output 30 from the target output 21. This distance should be minimized. The objective function module 31 relays the computed objective function to a model parameter processing module 32.

The model parameter processing module 32 receives the objective function from the objective function module 31, and based on the objective function computes new model parameters for the processing model 5, for example by use of a stochastic gradient method, to minimize the distance between the result output 30 and the target output 21. The model parameter processing module 32 relays the new model parameters to the processing model 5.

The processing model 5 receives the new model parameters, and adapts the model parameters of the processing model 5 based on the new model parameters.

The evaluation unit 4 includes an analysis data supply module 33, which for the analysis reads out microscopic images 24 from the memory module 18 and relays them to the fully trained processing model 5. The processing model 5 uses the received microscopic images 24 to carry out learned scoring mapping, in which data points for the analyte determination are assessed as relevant or nonrelevant. The fully trained processing model 5 may therefore also be referred to as a scoring model.

A result output readout module 34 is coupled to the output side of the processing model 5 and coupled to a compression module 35 via a channel 20. The result output readout module 34 reads out the result output 30 at the processing model 5 and transfers it to the compression module 35. The compression module 35 compresses the microscopic image in question based on the result output 30, via which the foreground of the microscopic images 24 is defined. In this way, the data volume of the images is reduced, and compressed images are generated.

The evaluation unit 4 also includes a microscopic image readout module 23. The microscopic image readout module 23 reads out microscopic images 24 (FIG. 3) from the microscope camera 12 and stores them in the memory module 18. The microscope readout module 23 may also be refined in such a way that it directly relays the microscopic images 24 to the analysis data supply module 33 without storing them in the memory module 18.

The data volume of the compressed images may be reduced in different ways. A distinction is made between candidate data points and background data points. Candidate data points are data points which at least in one coloring round, and preferably in n coloring rounds, contain color information that originates from the dye of a marker. The candidate data points thus depict a marker in an image. In contrast, background data points are data points whose color information in all coloring rounds does not originate from a marker that is coupled to an analyte.

A data point may be an individual pixel or voxel or a group of contiguous pixels or voxels. Pixels are image points of a two-dimensional image, and voxel pixels are image points of a three-dimensional raster graphic.

According to a first embodiment, in the compressed images the background data points are set to a certain color value, which is preferably "0." This results in image areas in which the pixels or data points all have the same color value. Images with contiguous areas that have the same color value may be compressed very efficiently. They may be stored in the PNG format, for example, which combines such color regions.

Alternatively, other compression methods for compressing color information of such images or image formats are known in which the color information is stored in compressed form, such as the following, for example:

Asymmetric Numeral Systems entropy encoding algorithms,
arithmetic encoding,
an algorithm based on the Burrows-Wheeler transform,
Huffman coding,
Lempel-Ziv coding (LZ77 or LZ78, for example),
a Lempel-Ziv-Markov algorithm,
a Lempel-Ziv-Storer-Szymanski algorithm,
a Deflate algorithm,
a Lempel-Ziv-Welch algorithm,
a prediction by a partial matching algorithm,
run-length encoding,
AV1 Image File Format (AVIF),
Free Lossless Image Format (FLIF),
High Efficiency Image File Format (HEIF),
Interleaved Bitmap (ILBM),
JBIG2,
JPEG 2000,
JPEG-LS,
JPEG XL,
JPEG XR,
discrete cosine transform (DCT),
lossless discrete cosine transform (LDCT),
Picture Exchange (PCX),
Portable Document Format (PDF),
Portable Network Graphics (PNG),
Truevision TGA, often referred to as TARGA,
Tagged Image File Format (TIFF),
WebP,
Block Truncation Coding (BTC),
wavelet compression,
DjVu,
ICER,
Portable Graphics Format (PGF),
Cartesian Perceptual Compression (CPC),
fractal compression,
JBIG2,
S3TC texture compression,
H.261,
Motion JPEG,
MPEG-1 Part 2,
MPEG-2 Part 2 (H.262),
MPEG-4 Part 2 (H.263),
Advanced Video Coding (AVC/H.264/MPEG-4 AVC),
High Efficiency Video Coding (HEVC/H.265),
Ogg Theora,
VC-1,
Motion JPEG 2000,
Dirac,
Sorenson Video codec.

In the following discussion, the term "PNG format" is representatively used as an example for storing color information having contiguous areas which contain pixels that are set to the same color value. Alternatively, however, another of the methods stated above may also be used for compressing the color information of the data points.

In one alternative format, storage takes place in an array using only one bit, regardless of whether a foreground data point or background data point is involved. An additional list is stored in which all color values of the candidate data points are continuously saved; an assignment of the candidate data points of the array to the color values of the list is established by use of an index. This format already results in a data reduction for an occupancy of 94%; i.e., 94% of the color values of the uncompressed microscopic image 24 are accepted in the compressed image. This format is also referred to below as a binary array.

A further format for storing the compressed images contains a list with coordinates and color values of all candidate data points. This format is also referred to as a sparse matrix. Above an occupancy of approximately 40%, such a sparse matrix is worthwhile compared to storing the uncompressed microscopic image 24 in question.

The compressed images may be two-dimensional images as well as three-dimensional images. Accordingly, the array of the binary array is also a two-dimensional or three-dimensional array.

Mixed forms of the above-mentioned formats are also possible for storing the compressed images. For example, the microscopic images 24 may be stored in uncompressed form after the first coloring rounds, since the occupancy can still generally be very dense here. After a certain coloring round, when the data density is sufficiently sparse, the microscopic image 24 may be stored in a compressed format. Such a procedure is advantageous in particular when a sparse matrix or a binary array is used. The microscopic images 24 of the first coloring rounds may be stored in the PNG format. The background data points that are combined with a color value may be retained when a change is made to a sparse matrix or a binary array, or all data may be transferred into the corresponding list. Such a transfer into a complete list involves computing effort and requires further write cycles, but reduces the data volume and thus results in further compression.

After the individual coloring rounds, the microscopic images 24 are thus converted into compressed images. The compressed images generated by the preceding coloring rounds may be retained unchanged, or read out again in order to be further compressed with the information obtained in the subsequent coloring round. Such a recompression may be performed after each further coloring round is carried out, or only after certain further coloring rounds are carried out. In particular, such a recompression may be advantageous after the last coloring round is carried out.

Carrying out the recompression results in a significant reduction in the data volume. However, such a recompression requires repeated reading and writing, which increases the number of write cycles. The application of the recompression may be specifically adapted, depending on whether the primary aim is to reduce the data volume or to reduce the write cycles. In principle, the efficiency of the compression is also a function of the type of experiment. When the color values of markers differ greatly from the color values of the background, the compression is very efficient from the beginning, so that a recompression is less necessary. If the difference between the color values of the markers and color values of the background is not very pronounced, a recompression is advantageous.

After the compressed microscopic images have been stored in the memory module 19, an identification data supply module 36 may read out the compressed microscopic images and supply them to an identification module 37. The identification module 37 is designed in such a way that it assigns a type of analyte to each candidate data point. The identification module 37 may, for example, initially binarize the color information of the data points. For this purpose, the coloring rounds in which the data point has detected a marker molecule is identified, and a colored signal or a "1" is then assigned to the corresponding coloring rounds, and an uncolored signal or a "0" is assigned to the further coloring rounds. The result bit series that result are then compared to target bit series of a codebook, the codebook including a target bit series for all types of analytes to be identified.

Alternatively, the identification module 37 may also cluster the data points in the compressed microscopic image by use of a cluster analysis algorithm, and a cluster center is then determined for each of the found clusters, and the cluster centers are matched with target cluster centers, wherein the target cluster centers are determined from target bit series of a codebook; the codebook in turn includes a target bit sequence for each type of analyte to be identified. Alternatively, the codebook may also include signal series of the particular types of analytes from a previous experiment, and the determined cluster centers are then matched with the cluster centers resulting from the reference recordings determined from the previous experiment.

The cluster analysis algorithm used is preferably one of the following: k-means clustering, Gaussian mixed model clustering, kernel-based principal component analysis, EM clustering, Leiden clustering, Louvain clustering, divisive analysis clustering.

It is also possible for the identification module 37 to carry out matching as described in EP 2 992 115 B1, WO 2020/254519 A1, or WO 2021/255244 A1, for example.

In the method explained above for identifying analytes, the microscopic images 24 are stored in compressed form in the memory module 18, it being ensured that all foreground information or all candidate data points is/are completely retained. As a result, on the one hand the necessary memory requirements and the number of write cycles are reduced, and on the other hand the processing of the data is speeded up significantly. This also prolongs the service life of the memory medium of the memory module 18, which is generally an SSD hard drive.

According to a further alternative, the identification module 37 may also include an identification processing model that has been designed and trained to directly output a type of analyte of the input data point or of the input data points in the compressed microscopic image.

Alternatively, the identification processing model may also be designed in such a way that it outputs a binarization of the input data points or of the input color information. A comparison to the codebook may then take place based on the output binary values or binary value sequences.

According to a further alternative, the identification processing model may also be an embedding model. The embedding model is trained in such a way that it embeds input data points into an embedding space so that data points and target bit sequences that belong to the same type of analyte are thus embedded in the embedding space in such a way that they have the smallest possible distance from one another, while data points and target bit sequences that belong to different types of analytes or to the background are embedded in the embedding space in such a way that they have the largest possible distance from one another. During the inference, the specific type of analyte for whose corresponding target bit series the embedding of the data point has the smallest distance is then assigned to a data point.

For the training of the scoring model, a final result of an experiment is used as ground truth (positive examples at analyte positions and negative examples at background positions) that has been obtained in a (partial) experiment, and that has been computed using the identification module 37, for example, without data compression methods. The positive examples are thus candidate data points that contain relevant color information, i.e., color information of markers, and the negative examples are background data points that contain no relevant color information, i.e., no color information of markers.

According to a further alternative, the annotated data set may be generated using other means instead of the identification module 37.

For example, the signals of the various markers may be simulated using a representative background image and a known point spread function of the microscope 2. The codebook is then also entered into such a simulation.

Alternatively, a generative model may also be trained to generate the annotated data set. Since generative models are particularly well suited for generating images, a particularly realistic annotated data set may be created using a generative model. In addition, one or more reference images that contain at least one background image may also be recorded, and for each background image at least one image in which analytes to be identified are coupled to a marker, and fluorescence signals of the markers in the particular image areas, may be detected. When various fluorescent dyes are used in the various coloring rounds, in addition each analyte should be marked with each of the various fluorescent dyes.

In addition, known conventional methods, for example from the patent applications EP 2 992 115 B1, WO 2020/254519 A1, and WO 2021/255244 A1 cited above, may also be used for generating the annotated data set.

Since the dyes of the different markers may illuminate with different brightnesses, and in the "background" there are often pixels which illuminate but whose illumination effect is not caused by a marker, in an individual image it is difficult to distinguish between which illuminating pixels originated from a marker and thus represent relevant information, and which illuminating pixels have other causes.

The scoring model may be designed as a classifier that selects positive and negative examples from an experiment and that is trained as a binary classification problem. The individual data points are classified as candidate data points or background data points, it being possible for the ultimate assignment to take place using an activation function (Softmax or Sigmoid, for example). The data points are individually classified in this scoring model, so that during the training of the scoring model the annotated training data include corresponding color values as input vectors or input tensors, which are input data point-by-data point, and as a target value include the information concerning whether the particular data point is a candidate data point or a background data point.

In the classification, additional context information may be taken into account which includes, for example, the color values in the surroundings of the particular data point, or context information that describes the particular experiment, which is then an integral component of the input vector or input tensor of the scoring model, and accordingly must also be taken into account in the training.

The classifier may also be designed as a linear model in which the weights of the linear combination are assigned to the individual rounds. In this way, it may be increasingly better decided, on a step-by-step basis, whether a data point belongs to the background. This depends greatly on the weights of subsequent layers. A run order could accordingly be sorted. Such a linear model has the advantage that only a single scoring model is needed, in contrast to multiple submodels.

The scoring model may also be alternatively designed to carry out a semantic segmentation. In the semantic segmentation, all data points of an image are subdivided into at least two classes, namely, candidate data points and background data points. When further context information is taken into account, the background data points may be subdivided into further classes, for example background data points that lie outside the region of a cell, and background data points that are situated in the region of a cell. The annotated training data of such a scoring model in each case include complete images as input vectors or input tensors, and include completely segmented images in each case as target vectors or target tensors, and in particular completely segmented images after taking a final coloring round into account.

The scoring model may be alternatively designed as a detection model. Here, similarly as for the classifier, positive and negative examples from an experiment are sampled to detect the candidate data points. A list containing coordinates of the candidate data points is output as the result. In addition, for the list containing the coordinates of the candidate data points, their extent may also be detected and output. The annotated training data include the corresponding color values as input vectors or input tensors, and as output vectors or output tensors include a list containing coordinates of the candidate data points, which may be additionally provided with the extent of the particular data points. Such a detection model is used in particular in combination with the storage of the images in the sparse matrix format.

In a further alternative, the scoring model may be designed as an image-to-image model. Instead of a "hard" decision between candidate data points and background data points, as explained above for the segmentation or classification, a "soft" decision may take place which indicates the likelihood and/or the density of foreground and background data points in the particular image areas. This may be output in the form of a heat map, for example. The annotated training data accordingly include the complete microscopic images 24 as input vectors or input tensors, and the correspondingly converted image in the output format in particular in the form of a heat map.

The following further options for the design apply for all the different embodiments of the scoring model described above:

In a certain coloring round, only those data points that have not yet been discarded in earlier coloring rounds can be analyzed. Such an embodiment significantly increases the processing speed, and reduces the computing effort and the data volume.

The analysis of a data point after a certain coloring round may be carried out based on the color value of the present coloring round, the color values of all previous coloring rounds, or the color values of a subset of the previously carried out coloring rounds. Such a subset may include, for example, the brightest color values for this data point in the previous coloring rounds. An intensity threshold value may be used to determine the brightest color values. However, it is also possible to determine the brightest color values based on a relative intensity, for example taking into account a predetermined number n of bright color values, where n may be a function of the number of coloring rounds carried out, or the bright and dark points being grouped corresponding to their brightness, and the bright color values having a similar intensity being taken into account in the analysis. The color values of a data point to be taken into account may also be determined according to other criteria, such as their characteristic signature and/or their color (for a multicolor image), and/or similarity to typical color values of the markers.

Alternatively, the machine learning system 1 may be made up solely of the evaluation unit 4. The annotated data set may be transferred to the memory module 18 of the evaluation unit 4 via a communication link or by a mobile data carrier, and the evaluation unit 4 is then trained based on the training data. When the processing model 5 of the evaluation unit 4 is fully trained, the evaluation unit 4 may also evaluate microscopic images 24 of the sample type corresponding to the learned processing imaging, independently of a microscope 2.

According to the first embodiment, the evaluation unit 4 is a computer that is provided separately from the microscope 2. Alternatively, the evaluation unit 4 may be integrated into the microscope 2 or be implemented by a cloud server, for example, which provides the evaluation to a user via a network connection.

The markers may in each case include an oligonucleotide and a dye. The oligonucleotides generally contain at least 10, preferably at least 15, nucleotides. The larger an oligonucleotide, the more specific it is. In special applications an oligonucleotide may also contain fewer than 10 nucleotides, as explained in greater detail below.

The samples are colored in coloring rounds with one of the markers in each case. The coloring with a marker takes place by applying multiple marker molecules of the same type to the sample and coupling them to the analytes contained in the sample. The marker molecules may couple directly to the analyte or also indirectly via probes that are coupled to an analyte (see WO 2020/254519 A1 and WO 2021/255244 A1, for example). Noncoupled marker molecules or "markers" for short are washed off and thus removed from the sample. Since only the markers that are coupled to the analytes or hybridized with the nucleotide sequence remain in the sample, only markers that are coupled to an analyte are seen under the microscope 2. The detection of such a marker under the microscope 2 means that an analyte is present at this location, and has a segment that is complementary to a coupling segment or a coupling medium (for indirect coupling), in particular for an oligonucleotide sequence of the corresponding marker. After the markers are detected or sampled, they are separated from the analytes by annealing, for example, and the sample may be marked with further markers.

Markers of different types, i.e., having different types of coupling segments, in particular different types of oligonucleotides, may also be provided with correspondingly different dyes, so that these different markers may be applied at the same time, and under the microscope 2 may be kept apart via different wavelengths, for example.

The exemplary embodiment explained above may be modified in different ways.

The above-mentioned scoring model is trained using a final result of an experiment and the corresponding generated microscopic images 24 of the coloring rounds in question. In addition to the final result, which is present in the annotated data set in the form of a binary array or in the form of a compressed target image, for example, even further context information may be supplied to the scoring model. This further context information may be, for example, user identification and thus the experiment content that is typical for the user, or additional information concerning the experiment itself. Such additional information concerning the experiment includes, for example, parameters that describe the method of coloring the sample in the individual coloring rounds. This experiment information may also be the expected number of analytes or also the expected ratio of the analytes contained in the sample, via which the sensitivity of the filtering may be adjusted. It is thus possible to avoid excessively heavy filtering in the early coloring rounds, or excessively light filtering in the late coloring rounds.

Within the scope of the invention, different scoring models that are specific for different experiments or different types of samples or different types of expected analytes may also be used for filtering the result microscopic images. The scoring models may, for example, be specially trained for the different experiments, types of samples, or the different types of analytes.

When the experiment, the type of samples, and/or data describing the expected analytes is/are correspondingly used as context information, the appropriate scoring model may also be automatically selected from a set of scoring models.

Within the scope of the invention, for a new type of experiment, a new sample location, or a new type of expected analyte, it is also possible to first carry out the identification of the analytes without compression of the result microscopic images, and after completion of the identification of the analytes in such an experiment, to compress the microscopic images 24 based on the final result, i.e., to convert them into one of the above-mentioned compressed formats and then train the scoring model based on the microscopic images 24 compressed in this way. The filtering may then be used as described above for compressing the image data for all subsequent samples of such a type of experiment, such a type of sample, and/or such a type of expected analytes.

According to one refinement of the method according to the invention, the order of the coloring rounds may be optimally set to allow candidate data points to be filtered as early as possible and background data points to be excluded. With a skillful selection of the markers, it may be ensured that all or at least almost all analytes in the first coloring rounds are marked. The markers may in each case be selected in such a way that they are specific for different subsets of the analytes to be identified, and whose overlap is as small as possible.

According to a further refinement of the method according to the invention, prior to the preparation of the data a step of carrying out a background correction of the color values may take place. According to the exemplary embodiment, the background correction is carried out using a rolling ball method. Alternatively, the background correction may also take place using a top hat method, homomorphous filtering, low pass filtering, or temporal filtering. Furthermore, it is conceivable to use an image-to-image model or a mixed model for the background correction. According to a further alternative, a mean shift method may also be used for the background correction. As further alternatives for the background correction, a method using principal component analysis [or] non-negative matrix factorization may be considered. A further alternative is correction via excitation of the autofluorescence, using a nonspecific laser for all data points of the images.

The method may also be modified in such a way that in the first coloring round or in the first coloring rounds, all analytes present are marked with one or more different markers. Very nonspecific markers may be used for this purpose. If the analytes are nucleic acid sequences, markers with relatively short oligonucleotides are preferably used which contain, for example, fewer than ten, in particular fewer than seven, and preferably fewer than five, nucleotides. This allows the early, complete or almost complete detection of candidate data points.

A further exemplary embodiment (aspect B) of the machine learning system 1 likewise includes the microscope 2, the control device 3, and the evaluation unit 4. The evaluation unit 4 differs from the evaluation unit 4 in the exemplary embodiment according to aspect A in that the evaluation unit 4 includes a control module 22, the processing model 5, the memory module 18, and the identification module 37.

Figure 5:
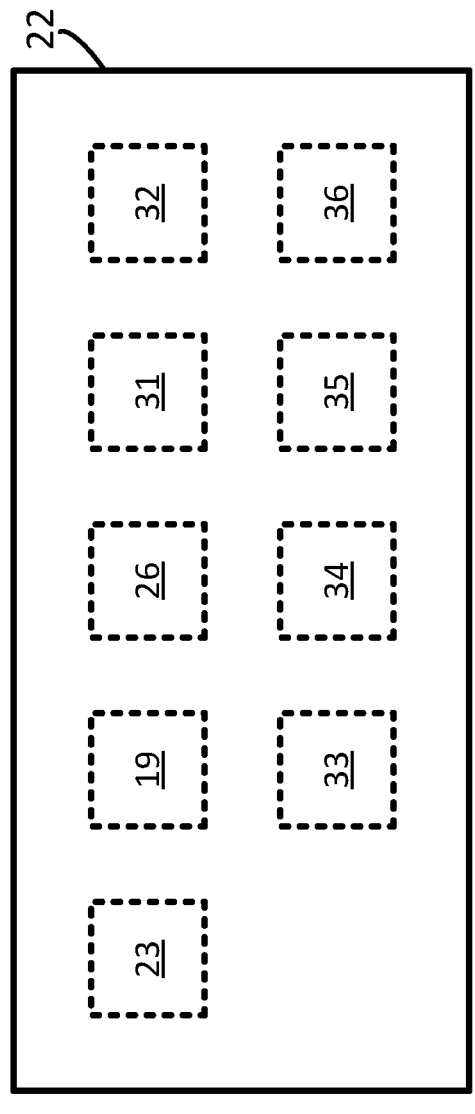
FIG. 5 shows a control module of the evaluation unit from FIG. 4, FIG. 6 schematically shows a method for preparing data according to one embodiment, FIG. 7 schematically shows a method for preparing data according to one embodiment, FIG. 8 schematically shows an evaluation unit according to a further embodiment, FIG. 9 schematically shows a method for preparing data according to one embodiment, FIG. 10 schematically shows a method for preparing data according to one embodiment, and FIG. 11 schematically shows a method for preparing data according to one embodiment.

The control module 22 implemented according to aspect B [Includes] the microscopic image readout module 23, the microscopic image registration module 19, the training data supply module 26, the objective function module 31, the model parameter processing module 32, the analysis data assignment module 33, the result output readout module 34, the compression module 35, and the identification data supply module 36, as illustrated in FIG. 5 by the modules indicated in dashed lines in the evaluation unit 4. Data may be exchanged between the individual modules of the control module 22.

According to one alternative, the color information may also be assessed based on predetermined criteria. No processing model 5 is required for this alternative; instead, the evaluation unit 4 can suitably filter the color information, for example. For this case, the evaluation unit 4 does not include the above-described further modules which are necessary for the training and the inference.

In the exemplary embodiment according to aspect B, the processing model 5 is once again a convolutional neural network (CNN), and once again is implemented as a scoring model. The processing model 5 once again includes an input layer, multiple intermediate layers, and an output layer. The processing model 5 is trained, for each data point of the multiple images of the sample, to subsequently assess the particular color values for whether they represent a colored signal in each case and accordingly with a certain likelihood encode an analyte. The assessment of the particular color values takes place in each case after a new microscopic image 24 is recorded. For this purpose, the processing model 5 reads in the n color values of a data point selected after a previous coloring round as well as the color value recorded in the new coloring round, assesses the n+1 color values, and based on the assessment selects the n color values that most likely represent a colored signal, where n is smaller than the total number of coloring rounds.

According to one alternative, the processing model 5 may also be designed as a multilayer perceptron (MLP), as a diffusion network, as a transformer network, or as a sequential model (an RNN, for example).

The annotated data set includes a series of color values of a data point over all coloring rounds of an experiment. In the series, the n color values that most likely correspond to a colored signal are marked.

The annotated data set is created as explained above with reference to the embodiment according to aspect A.

In the training, in each case n+1 color values of the series are input into the processing model 5 and assessed. For example, if the processing model 5 is implemented as a classification network and assigns a class to each of the input n+1 color values, for example one class corresponds specifically to the signals that are most likely a colored signal, and a further class includes the uncolored signals.

The objective function detects a difference between assessments or assignments for the particular classes, output by the processing model 5, and the classes to be assigned according to the annotated data set.

Analogously to the method for training the processing model 5, described above with reference to the exemplary embodiment of aspect A, the model parameters of the processing model 5 are adapted by optimizing the objective function, for example by use of a stochastic gradient method.

In order to also train the processing model 5 for coloring rounds in which previously only b<n+1 coloring rounds or color values have been recorded during the experiment, in the training for these early rounds, when inputting the color values into the processing model 5 for coloring rounds for which no color values are present, placeholders, for example zeroes, are filled in so that a color values and n+1−b placeholders are entered into the processing model 5. The n+1 input values are assessed by the processing model 5, and the corresponding assessments are output.

In particular for early coloring rounds, it is very likely that fewer than n of the n+1 input color values according to the annotated data set are colored signals, since the colored signals are preferably distributed fairly uniformly over all coloring rounds. However, in the training it is important that the processing model 5 specifically recognizes the input color values that are marked as a colored signal.

A color value that is initially wrongly assigned to the class of colored signals may still be correctly assigned to the class of uncolored signals in a subsequent coloring round, when further colored signals are added to the n+1 color values entered into the processing model 5.

Therefore, a colored signal that is wrongly assigned to the class of uncolored signals is preferably penalized more heavily in the objective function than an uncolored signal that is wrongly assigned to the class of colored signals.

For example, if a colored signal is misclassified as an uncolored signal, this is to be so assessed in the objective function using a higher factor, for example, while for an incorrect assessment of an uncolored signal as a colored signal, the incorrect assessment is merely assessed using a lower factor. Due to this greater consideration of false-negative uncolored signals, the model may be prevented from wrongly identifying colored signals as uncolored signals and discarding the information that is important for identifying the analytes.

Thus, a colored signal that is wrongly identified as an uncolored signal is preferably entered with more weight into a distance measure or a similarity measure of an objective function than for the reverse case.

According to one alternative, an assignment to the classes of colored and uncolored signals may also take place "soft" by assigning a value between 0 and 1 to each color value. The assigned value indicates how likely it is that the particular color value is a colored signal.

In the training, the processing model 5 may be trained in such a way that an output layer in each case outputs the assessments as described above, and based on the assessments, the corresponding n color values are selected and stored in the memory module 18 by the control module 22.

During the inference, the processing model 5 may be modified in such a way that the processing model 5 is expanded by a further processing layer in addition to the output layer used during the training. The processing layer performs a matrix multiplication in which the result output 30 of the output layer is appropriately multiplied by the input n+1 color values, so that only the selected n color values are output by the processing layer of the processing model 5. In this way, the complete processing or the selection of the n color values may be carried out completely using, for example, a graphics card that is optimized for this purpose.

Alternatively, in the training the processing model 5 may be directly trained to output the selected color values. In the training, in each case n+1 input values are input into the processing model 5 and n output values are output. For this case, the annotated data set may include complete color value sequences, in which case only a selection of n+1 of the color values is input in each case, and similarly corresponding n output values are selected for the training. Alternatively, however, the annotated data set may in each case include pairs of n+1 input values and n output values.

During storage the n color values are stored, and a remaining nonselected color value may be discarded. According to one alternative, further information may be stored in addition to the selected n color values. The further information includes, for example, information about the coloring rounds corresponding to the selected color values, for example a number or the point in time of the coloring round. In addition to the selected n color values, statistical information about the discarded color values, for example a sliding average value, a standard deviation, a minimum, a maximum, a median of a property of the color information, as well as information about an extent, intensity, or color of the data points, may be stored.

According to the exemplary embodiment as per aspect B, an experiment includes a total of m coloring rounds. In the m coloring rounds, the analytes are marked in i of the m coloring rounds, using markers. The number of n selected color values is preferably equal to the number i of coloring rounds, in which an analyte is marked with a marker. According to one alternative, n=i+a, where a=0, 1, 2, or 3. As mentioned above, in an experiment the number of markers, and thus the number of color values to be selected, may vary as a function of the analyte. In this case, n is the maximum number of color values that encode for one of the analytes.

According to one alternative, the color values that most likely represent a colored signal are selected not by a processing model 5, but instead, based on predetermined criteria using a conventional preselection. The criteria for selecting the n color values may include, for example, threshold values for a minimum and/or maximum intensity, the threshold values being statically specified or dynamically determined. The threshold values may vary for a minimum and/or maximum intensity as a function of the color of the color values, i.e., according to the color channel 20 used, and/or may be determined via a minimum distance from a predetermined target value of the intensity, color, and/or extent.

The other details described with reference to the exemplary embodiment according to aspect A may be applied analogously to the exemplary embodiment according to aspect B.

A further exemplary embodiment according to aspect C of the machine learning system 1 likewise includes the microscope 2, the control device 3, and the evaluation unit 4.

The evaluation unit 4 according to this exemplary embodiment corresponds to the evaluation unit 4 according to the exemplary embodiment as per aspect B, for which reason identical parts are not explained again. The evaluation unit 4 according to this exemplary embodiment differs from the evaluation unit 4 according to the exemplary embodiment as per aspect B, in that the processing model 5 has been trained to perform a projection onto a subspace. The subspace encompasses k dimensions, where k<m, and m indicates the number of coloring rounds of an experiment. The processing model 5 includes c various input strings, and d input channels for each of the input strings. The c various input strings share an output string having k output channels. The product of c and d is preferably exactly equal to the number of coloring rounds m.

According to the present invention, each of the input strings is assigned to a coloring operation. A coloring operation may include one or more coloring rounds. A coloring operation may include multiple coloring rounds, for example, when markers having different colors are used, and which are excited over a broad band and recorded with a single image. The number of coloring rounds per coloring operation corresponds to the number d of input channels per input string.

Alternatively, a coloring operation may also have multiple markers with different colors, which are specifically excited in each case, and d images are then correspondingly recorded.

In the projection onto the subspace, in principle an input vector having the dimension m is mapped onto an output vector having the dimension k. For each data point, the images of a coloring round deliver an intensity value in each case that forms one of the vector components 38 in the input vector. Since after each coloring operation a vector component is generated only for each coloring round of the coloring operation, the other vector components 38 are equal to zero, for which reason it is sufficient to provide only d input channels for each input string, where d is the number of coloring rounds per coloring operation, or corresponds to the number of color channels 20 in the experiment.

In the experiment, after d images are recorded in each case during a coloring operation, for each data point d color values are input into one of the input strings. These are projected onto the subspace by the processing model 5 and sequentially aggregated in the k output channels. For example, each of the d images may correspond to a different one of d various color channels that are used during the experiment.

If the transformation is a principal axis transformation or a singular value decomposition, for example, the projection may also be computed in the conventional way via matrix multiplication, and a training of the processing model 5 then corresponds specifically to the determination of bases of the transformation matrix based on a training data set. For this case the training is an unsupervised training in which the bases of the principal axis transformation are estimated.

The training data set may either be compiled based on a previous experiment, or, as described above for the further aspects, may be created using a generative model, for example.

According to this exemplary embodiment, the projection is a linear transformation, in the present case a transformation based on a principal axis transformation. The bases as well as the transformation matrix of the principal axis transformation have been determined in a previous experiment, for example, or in the same experiment based on a portion of the data, for example.

According to this embodiment, the processing model 5 computes, based on the bases of the transformation matrix determined in the training, the corresponding projections and aggregations. In this case the model parameters of the processing model 5 correspond specifically to the parameters of the transformation matrix of the principal axis transformation.

For a principal axis transformation or principal component analysis, although in principle a coordinate system is only rotated and displaced, the dimension is not reduced. However, for a principal component analysis in multidimensional space, the components are selected in such a way that their variance and thus their information content progressively decrease. The last components explain the lowest variance of the data, and may be regarded strictly as noisy data. Therefore, the last components may be omitted, as a result of which the dimension of the output vector, also referred to as the aggregation vector 40, may be reduced significantly compared to the original dimension For example, if d=1, for example only a single color contrast is considered. After each coloring round a color value of the particular coloring round is input into the corresponding input string; i.e., in the ith coloring round the ith vector component 38 is input into the ith input string. Each of the input vector components 38 is sequentially aggregated in the k output channels over the m coloring rounds. If the number of coloring rounds is m=16, for example, the 16 color values are input in succession into the 16 input strings.

The number of coloring rounds is stated here as 16 only as an example. The number of coloring rounds may be freely selected, depending on the particular experiment and the markers used, as well as the analytes to be identified.

For example, if d=2, for example two different color contrasts or two different color channels 20 are recorded. The two color values recorded in the different color contrasts are then simultaneously input into an input string having two input channels. The processing model 5 projects the two input channels onto the k output channels and aggregates the projections of the various input strings. If the experiment once again includes m=16 coloring rounds, the processing model 5 has eight input strings with two input channels each, in each case one for each color contrast. After two coloring rounds in each case, i.e., after the two color contrasts have been recorded, the two color values of the two color contrasts are input into the particular input string.

That is, the vector component 38, which is jointly input into an input string, is also jointly projected onto the subspace. For example, the particular vector having an entry in the particular vector component 38 may be multiplied by a projection matrix 39, and if a linear transformation is involved, the resulting projection vectors are sequentially summed, resulting in the aggregation vector 40 (see the bottom portion of FIG. 6).

Figure 6:
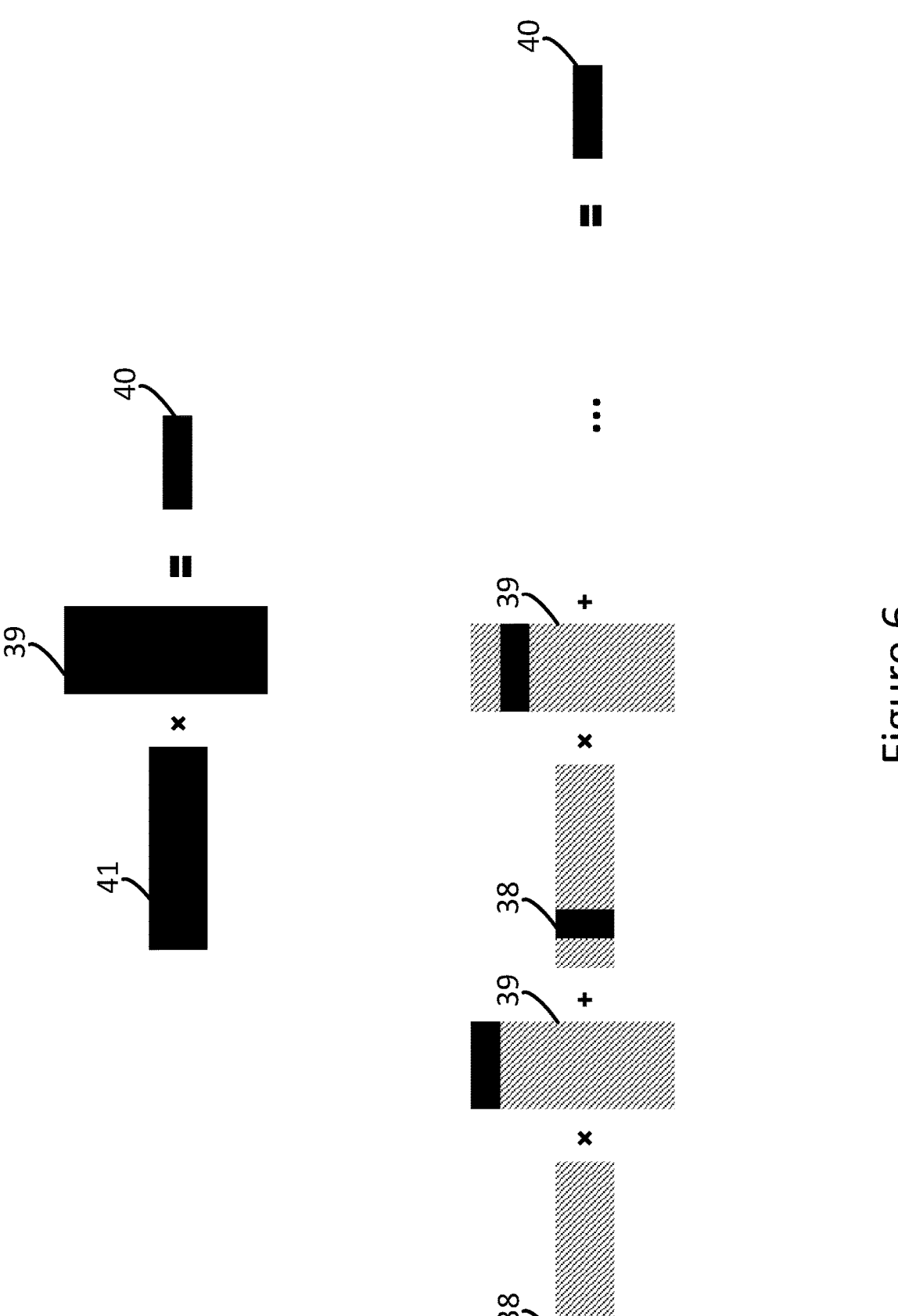

For a principal axis transformation, normally a complete raw data vector 41 together with all components is transformed into the subspace in order to obtain the aggregation vector 40 (see the top portion of FIG. 6).

As a result of it also being possible to carry out the principal axis transformation on a component-by-component basis, as described here the vector components 38 may also be transformed and aggregated individually or corresponding to the number d of coloring rounds per coloring operation. Thus, a division into input strings is not necessary here, and the vector components 38 of the individual coloring rounds could also be individually transformed and aggregated.

As a result of the subspace having fewer dimensions than the origin space, the data volume to be stored after a certain coloring round may be greatly reduced.

The first principal component of the principal axis transformation may optionally be omitted in the projection that is learned by the processing model 5.

According to one alternative, the processing model 5 may also learn a singular value decomposition. According to a further alternative, the processing model 5 may also be trained to carry out a nonlinear transformation. If the processing model 5 carries out a nonlinear transformation, it may also [be designed] as a neural network, for example, such as a CNN, an RNN, an MLP, or also a transformer network.

If the transformation is a nonlinear transformation and implemented by means of a trained neural network, for example, it may possibly be necessary and advantageous to input the color information of the d coloring rounds of a coloring operation together into an input string that has d input channels.

For example, in such a case a neural network may intrinsically also learn certain constraints via the manner in which data are input. One possible example of such a constraint is that for each data point in each coloring operation, only one of the coloring rounds should ever include a colored signal.

If the projection is a nonlinear projection, the aggregation may also include multiplying the particular components of various coloring rounds by one another, although any other computing operation may also be used for the aggregation.

It has been shown that for this type of recording, a first principal component of the principal axis transformation represents the absolute brightness. However, the absolute brightness plays essentially no role for the encoding of analytes, for which reason the first principal component may be disregarded.

The processing model 5 has been trained using an annotated data set, the annotated data set in each case including vectors with color values from m coloring rounds and corresponding projected aggregation vectors 40.

According to one alternative, instead of the corresponding projected aggregation vectors 40, the annotated data set in each case includes corresponding projections of the individual vector components 38, i.e., projections of individual color values. Via the inputting of individual vector components 38, the processing model 5 may be trained in a targeted manner to project the particular component 38.

The training of the processing model 5 according to this exemplary embodiment as per aspect C takes place as described above with reference to the exemplary embodiments as per aspects A and B, by suitably adapting the model parameters to optimize an objective function, the objective function detecting a difference between a result output 30 that is output by the processing model 5 and a target output of the annotated data set.

During the inference, the aggregation vector 40 may be input into the identification module 37 after the output by the processing model 5, the identification module 37 including an identification processing model. The identification processing model is designed to determine a type of analyte that corresponds to the input aggregation vector 40. The identification processing model is trained as a classification network, and directly outputs a class that corresponds to a recognized type of analyte.

According to one alternative, the identification processing model outputs a bit sequence; the bit sequence may then be compared to expected bit sequences for the various types of analytes to be detected in order to determine the particular type of analyte.

According to a further alternative, the determination of a type of analyte takes place without a network being trained, and instead either the aggregation vectors 40 are analytically back-transformed and target bit sequences are compared to the types of analytes to be detected, for example after a binarization of the back-transformed vectors, or target aggregation vectors are generated from typical series of color values for each of the types of analytes to be detected, for example by simulation or by using data from an earlier experiment by projecting the typical series of color values into the subspace. A comparison of aggregation vectors 40 of the experiment to the target aggregation vectors then takes place in the subspace.

According to a further alternative, instead of the processing model 5 the evaluation unit 4 includes a processing module in which the principal axis transformation, the singular value decomposition, or some other suitable linear or nonlinear transformation is carried out analytically, without the use of a network to be trained.

According to one embodiment of the exemplary embodiments as per aspect C, a basis for the principal axis transformation or the singular value decomposition is selected based on a semantic segmentation of the recorded images.

A further exemplary embodiment according to aspect D of the machine learning system 1 likewise includes the microscope 2, the control device 3, and the evaluation unit 4.

Figure 8:
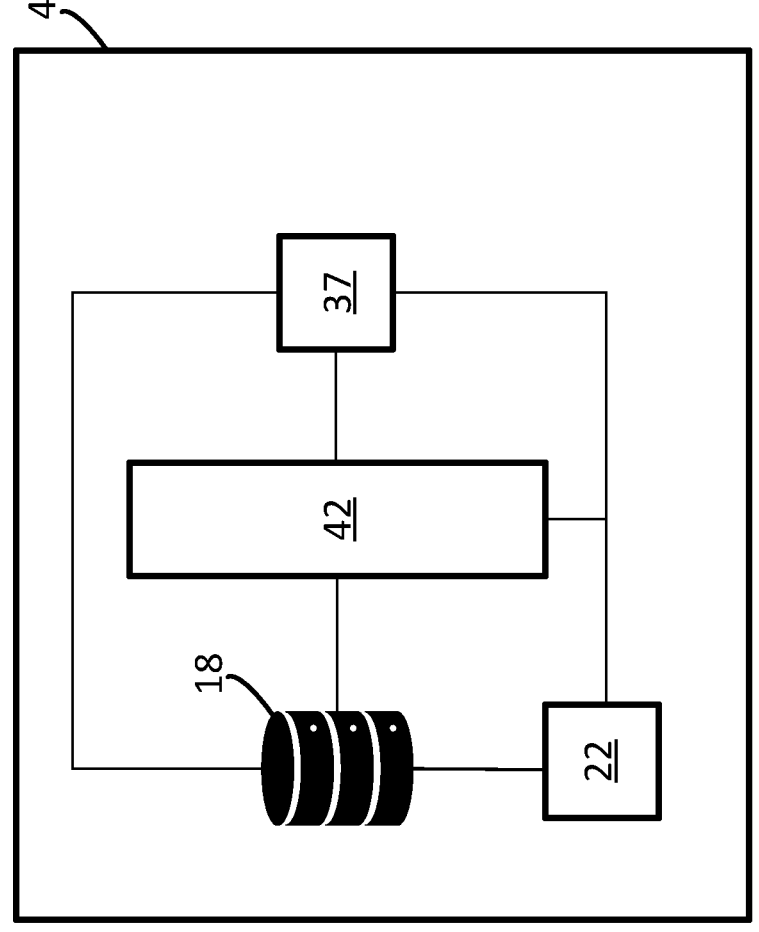

The evaluation unit 4 according to this exemplary embodiment corresponds to the exemplary embodiments explained above, for which reason identical parts are not described again. However, the evaluation unit 4 according to this exemplary embodiment differs from the evaluation units 4 according to the exemplary embodiments as per aspects A through C in that the evaluation unit 4 includes a cluster analysis module 42 instead of the processing model 5 (see FIG. 8).

Figure 7:
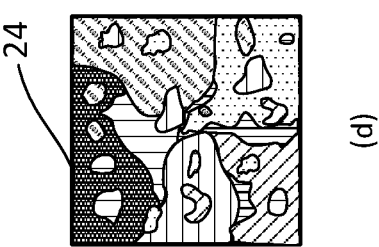
Figure 7:
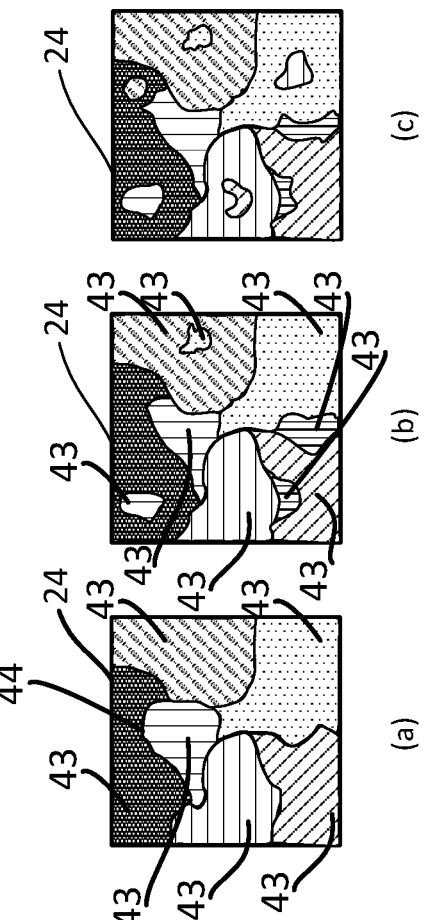

The cluster analysis module 42 is designed to carry out, after a coloring round, a cluster analysis of an image 24 that is recorded according to the coloring round. For this purpose, the color values having similar values or intensity values are clustered in such a way that data points having similar intensity values are assigned to the same cluster 43. According to this exemplary embodiment, the clustering takes place globally over the entire image 24 (see FIG. 7).

After the color values are appropriately clustered, a cluster ID is assigned to each data point, and the cluster ID is stored instead of the color value. In addition, a representative color value may be stored for each cluster ID. This may be, for example, an average value of the color values of the data points of the particular image that correspond to the particular cluster ID.

After each further coloring round, the obtained color values are reclustered and added as a further feature dimension to the clusters 43 determined according to the previous coloring rounds. Once again, for each of the clusters 43 the representative color value or intensity value of the particular cluster for the particular coloring round is stored.

New clusters 43 may arise with repeated clustering. In general, for new clusters, existing clusters 43 are subdivided into smaller clusters 43, which result from the color values of the earlier coloring rounds. Cluster boundaries 44 may be shifted, as is apparent, for example, in a comparison of the partial images (a) through (d) in FIG. 7. Such shifting occurs when the distances of the intensity values of neighboring clusters 43 are small after one of the first coloring rounds, and the distances of the intensity values of later coloring rounds are greater, wherein the cluster boundaries 44 of the areas having different intensity values of the later coloring rounds differ from those of the first coloring rounds. Due to the greater distances of the intensity values of the later coloring rounds, the pattern of the boundaries 44 of the individual clusters 43 is then redetermined in this area.

If an experiment includes 16 coloring rounds, for example, for each cluster 43 a cluster ID as well as the representative color value or intensity value corresponding to the particular cluster 43 in the particular coloring round are stored. For each data point, in each case only the cluster IDs that correspond to the particular data point of the image are stored. During clustering, for example a number, in particular a maximum number, of clusters 43 to be formed is specified, for example 128, 256, or 512. This specification of the maximum number of clusters 43 corresponds to the number of bits necessary for storing the cluster IDs. The fewer the bits that are necessary for describing the cluster IDs, the smaller is the data volume to be stored.

The number of clusters 43 is preferably larger than the number of types of analytes to be identified; in particular, for all types of analytes to be identified at least one cluster 43 is provided in each case, the same as for all possible various backgrounds.

In addition to the representative value, for example a variance, a median, or other sliding statistical values based on the color values or intensity values may also be generated and detected.

A cluster algorithm that is used may be, for example, a partitioning, hierarchical, graph-theoretical, or optimizing cluster algorithm.

The clustering may take place with supervision, for example, although unsupervised clustering may also be implemented by the cluster analysis module 42.

If according to one alternative a local cluster method is used instead of a global cluster method, only contiguous clusters 43 form. With a local cluster method, the image position is taken into account in each case in addition to the intensity values, so that contiguous clusters 43 locally form in each case, which are stored corresponding to their cluster IDs. With local clustering, generally more clusters 43 result overall than with global clustering, since only pixels in the local surroundings of the particular cluster 43 are taken into account in the cluster analysis. In this way, local differentiation may be performed much more individually than with global clustering. This also results in less loss of rarely occurring color values during the local clustering.

As a result of combining the color values of the recorded images into clusters 43 having similar values, in each case only the particular cluster IDs have to be stored for each of the data points. The memory usage when storing the various images from the coloring rounds may thus be reduced significantly.

According to one alternative, the cluster method may be carried out using a processing model 5, for example a convolutional neural network (CNN).

A cluster analysis algorithm used is preferably one of the following: k-means clustering, Gaussian mixed model clustering, kernel-based principal component analysis, EM clustering, Leiden clustering, Louvain clustering, divisive analysis clustering.

After all coloring rounds are recorded, based on the stored clustered data a type of analyte may be assigned in each case to the clusters 43, based on the particular series of intensity values of the particular clusters 43. For this purpose, the particular series of intensity values is first binarized, and then compared, for example, to target values or target bit sequences kept in the codebook.

Alternatively, an identification processing model may be trained to assign a type of analyte to the clusters 43, based on the clustered data.

According to the described exemplary embodiment, context information may be used in the cluster analysis and also for identifying a type of analyte, for example in order to suitably improve a particular clustering or the identification of a type of analyte.

A further exemplary embodiment according to aspect E of the machine learning system 1 likewise includes the microscope 2, the control device 3, and the evaluation unit 4.

The evaluation unit 4 according to the exemplary embodiment as per aspect E corresponds to the preceding exemplary embodiments, for which reason identical parts are not described again. The evaluation unit 4 according to the exemplary embodiment as per aspect E differs from the previously described evaluation units 4 in that the evaluation unit 4 as per aspect E includes a quantization module 45.

The quantization module 45 is designed to subdivide the recorded image into quantization regions after one of the images in a coloring round is recorded. In the different quantization regions of an image, intensity values of the pixels or the color values of the data points are encoded in each case with a respectively different quantization, and the new quantities, as intensity values or color values, are stored as color information of the pixels or of the data points.

Figure 9:
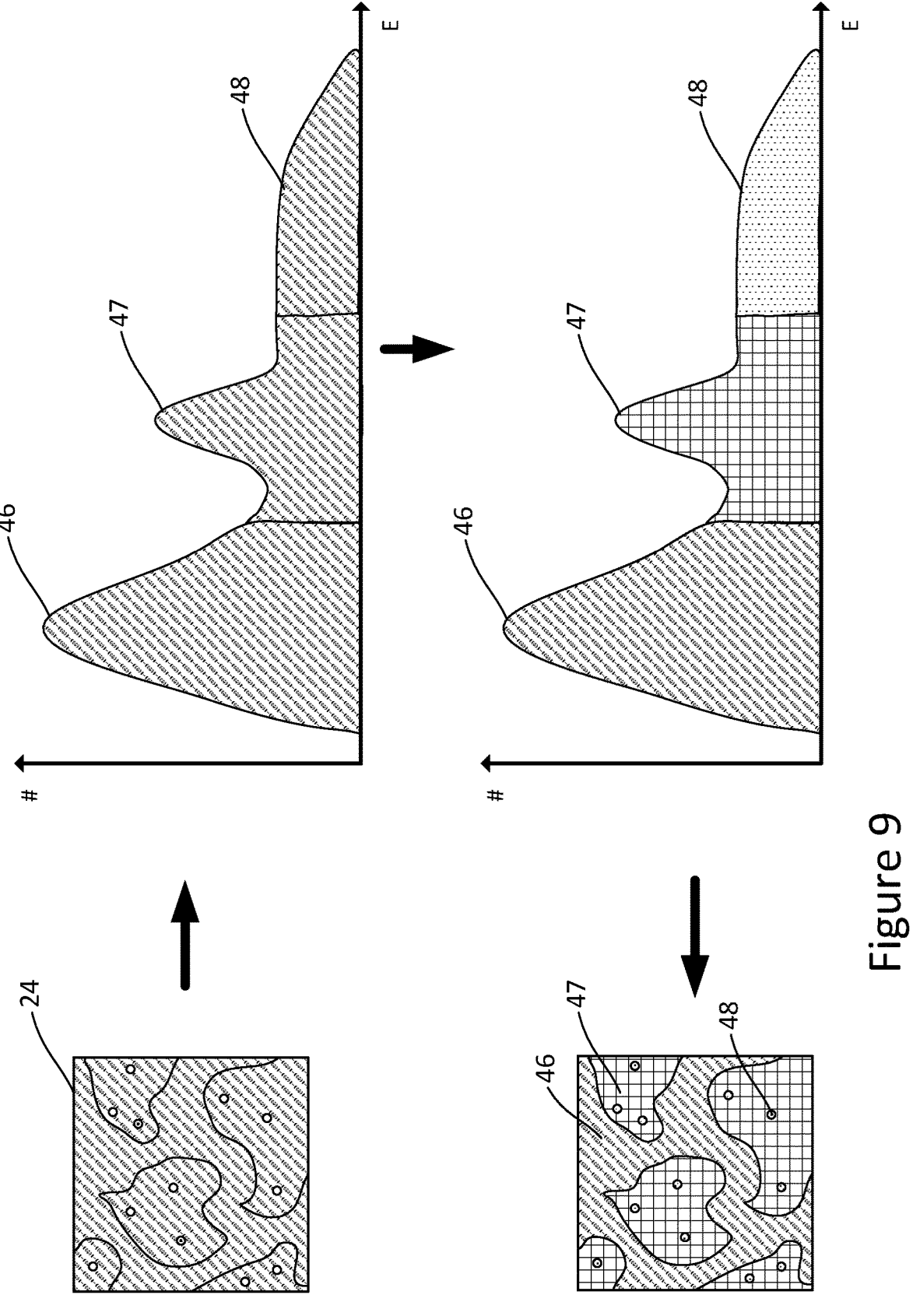

Although a camera encodes an entire image area with the same quantization, the inventors have found that in various image areas that have been appropriately subdivided by semantic segmentation, for example, very different quantizations of the intensity values or color values are meaningful for making available the information content that is necessary for analyzing the analytes. Via a suitable quantization of the various image areas, a tremendous amount of memory space may be saved in storing the images. This is explained in greater detail below with reference to FIG. 9.

For example, if data points in certain image areas detect signals from areas in a sample in which only background and no analytes occur, referred to below as the so-called low-intensity range 46 (see FIG. 9, for example), primarily low-intensity values or color values occur here. However, since no analytes occur in these areas, it is sufficient to encode these areas with low intensities 46 only with a quantification having a low bit depth and a relatively large interval.

Furthermore, there are image areas in a mid-intensity range 47 in which signals of markers coupled to analytes appear, but in which the color values or intensity values differ only slightly from the intensity values or color values of the background, so that for these image areas it is very important to use a quantization which in relation to the image areas with low-intensity values 46 or color values has a finer quantization or higher bit depth, and thus a smaller interval width.

In addition, for example high-intensity ranges 48 with very high intensity values or color values also occur. For these image areas, it has been shown that pixels or data points that detect signals of markers, i.e., detect colored signals, have a very high intensity value or color value which differs greatly from intensity values or color values in which a marker is not coupled to the detected analytes, and the intensity value or color value may correspondingly be easily distinguished from an intensity value of a colored signal.

For example, if a quantization having a bit depth of only 2 bits is now selected for the so-called low-intensity range 46, a quantization having a bit depth of 14 bits, for example, is selected for the mid-intensity range 47, and a quantization having a bit depth of 4 bits, for example, is selected for the high-intensity range 48, tremendous data volumes are saved when storing the images for the low-intensity ranges 46 and the high-intensity ranges 48, but without losing information necessary for identifying the analytes.

The number of various quantization regions actually used depends on the experiment in each case. In each case a bit depth and a distance of the interval may be freely selected. The distance may be fixed or also variably set, for example. The quantization may be selected corresponding to the expected intensity values.

For example, it may be necessary to select the number of quantization regions as a function of various types of cells under consideration. For example, the intensity values of a first type of cell may lie in a first quantization region; in this first quantization region a fine quantization with a high bit depth is to be selected. For example, if the intensity values of a second type of cell lie in a second quantization region, a fine quantization with a high bit depth is likewise to be selected for this second intensity value area. In addition, for example image areas that detect only background, as well as image areas that detect bright spots, also occur in the experiment. The image areas that detect only background may once again be quantized with only a 1- or 2-bit bit depth, and the bright spots, for example as described above, may be quantized with a 4-bit bit depth.

For example, in another experiment the quantization region having very low-intensity values may be omitted, since, for example, an entire area under consideration is completely covered with cells. In this case the image area that detects only a background is omitted, the same as with the quantization region having low-intensity values.

The quantizations are selected so that the combination of encoded intensity values plus the information concerning the quantization region to be applied in each case consumes no more memory than a quantization of the detected intensity values that is output by the camera.

For the quantization regions, for example boundaries may be established beforehand based on intensity values, so that each quantization region always corresponds to certain intensity ranges.

Alternatively, the images may be divided into semantically different quantization regions.

According to a further alternative, a frequency of the individual intensity values is initially detected, and the intensity limits of the various intensity ranges or quantization regions are established based on the frequency.

According to a further alternative, the quantization regions may also be established by clusters having similar intensity values.

According to a further alternative, the quantization regions may be established based on a semantic segmentation, and in the semantic segmentation of the images, for example a segmentation takes place in the background for certain cell areas, for example the cell nucleus, or for a cell border.

During the experiment, the quantization regions are established once before the first quantization of an image, the quantization regions preferably being established using a background image.

According to one alternative, the quantization regions are established after the first coloring round, it being possible for the quantization regions to be established based on a partial image or based on a complete image.

According to a further alternative, after each coloring round the quantization regions may also be re-established for the particular recorded image. According to a further alternative, quantization regions may be [established] in each case after several of the coloring rounds of an experiment are recorded, based on partial images or complete images.

After the experiment, for example an identification of a type of analyte for data points that encode an analyte may take place based on the stored, requantized intensity values.

For this purpose, a back-transformation may take place; although it is fairly inaccurate due to the altered quantization, this inaccuracy occurs only in the areas in which it is insignificant, so that a sufficiently accurate determination of the type of analyte should also be possible, using the back-transformed data.

Alternatively, the requantized intensity values may also be suitably binarized and compared to the target bit sequences of the codebook.

According to a further alternative, an identification processing model, as described above, may also be trained using an annotated data set in which the color information values have been stored together with the requantized intensity. For this case a back-transformation is omitted, and the identification processing model may directly process the requantized intensity values.

A further exemplary embodiment according to aspect F of the machine learning system 1 likewise includes the microscope 2, the control device 3, and the evaluation unit 4. This exemplary embodiment corresponds to the preceding exemplary embodiments, for which reason identical parts are not described again.

Figure 10:
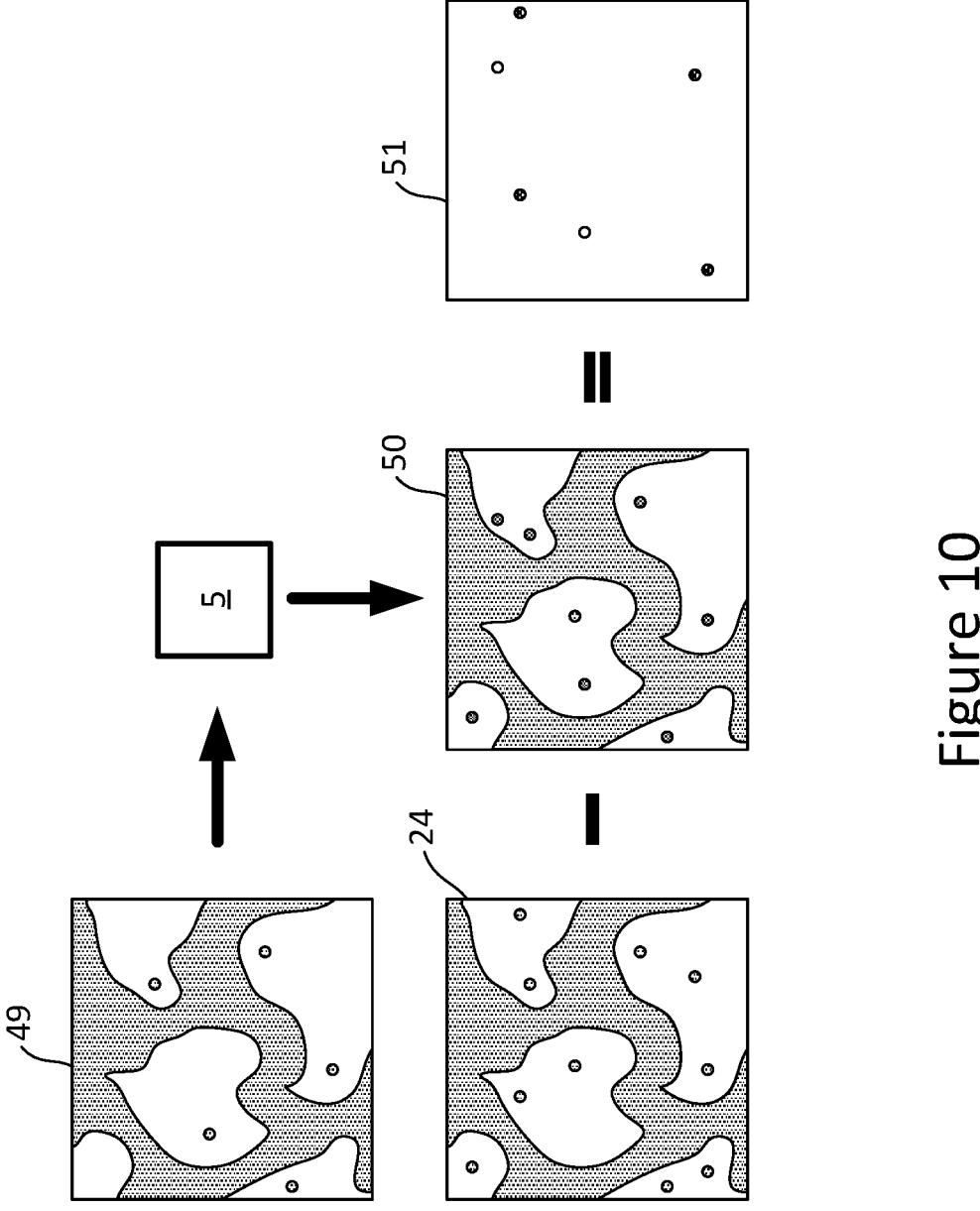

The evaluation unit 4 according to this exemplary embodiment differs from the evaluation unit 4 as per aspect B in that the processing model 5 has been trained to predict, for an nth coloring round, an expected predicted image based on predicted image data 49 of one or more preceding coloring rounds and/or based on predicted image data 49 of the present coloring round (see the schematic illustration in FIG. 10).

For example, the predicted image data 49 may include all images of an experiment that have been previously recorded. These include images that have been recorded in a previous coloring round, as well as image planes of a Z image that have been recorded before an image plane of the Z image presently being recorded. The predicted image 50 is determined, using the processing model 5, before or after recording of the image plane of the Z image presently being recorded, for this purpose the processing model 5 having been trained or configured to determine a corresponding predicted image 50 specifically for each image to be recorded or for each image plane of a Z image to be recorded.

That is, for each determined predicted image 50 there is a corresponding recorded image 24.

Alternatively, it is also possible for only a portion of the images recorded prior to an image to belong to the predicted image data 49.

The processing model 5 is trained separately for each coloring round; i.e., for each coloring round there is a subprocessing model that has been specifically trained for the particular coloring round. An annotated data set includes, for example, a set of images 24 as predicted image data 49, and a target image that corresponds to the predicted image data 49 and that corresponds specifically to the image that is to be predicted by the processing model 5. Accordingly, the predictive model 5 is trained as an image-to-image model. Such predictive image-to-image models are also referred to as regression models.

According to one alternative, the processing model 5 may also be an individual model, in which in addition to the input image data on which the predicted image 50 is then based in each case, context information which depicts, for example, a particular number of a coloring round of the input image data is input into the processing model 5.

According to a further alternative, the processing model 5 may also be an RNN, a predicted image 50 of a coloring round n+1 based on the image data of a present coloring round n and based on an internal state of the RNN.

Furthermore, the predictive model 5 may be trained separately for each new experiment. For this purpose, for example a pretrained model may be selected that is trained via transfer learning for the particular experiment, or a model is completely trained.

For example, as described above with reference to the further exemplary embodiments, the predictive model 5 may be selected from an existing model catalog. For example, the model catalog includes pretrained predictive models 5, prior to the inference it being possible to check whether the pretrained predictive model 5 makes sufficiently good predictions; otherwise, prior to the inference the predictive model 5 must still be trained for the upcoming experiment.

A difference image 51 is computed from the predicted image 50 and from the corresponding recorded image 24. With a sufficiently well trained processing model 5, a difference between the predicted image 50 and the corresponding recorded image 24 is very small, so that the difference image 51 includes mostly zeroes. After the difference image 51 is computed, the difference image 51 is stored as color information. As a result of the difference image 51 including mostly zeroes, the difference image 51 may be stored very efficiently, and for the storage, significantly less data volume is required than for storing the detected images or image planes of the Z images.

As a result of the prediction of the predicted images 50 being reproducible, the detected images may be reconstructed in each case from the stored difference images 51. For this purpose, first an uncompressed stored image of the first coloring round is read out. Based on the first image, stored in uncompressed form, an image of the second coloring round is predicted using the processing model 5, and the actual image of the second coloring round is then determined using the stored difference image 51 and the predicted image 50 of the second coloring round. The reconstruction takes place correspondingly for the images of the further coloring rounds. The analytes detected in the images or in the series of images are subsequently determined, based on the reconstructed images.

Instead of complete images, excerpts of the images may be used for the training. This applies for excerpts in a two-dimensional image and also for excerpts of image planes of a Z image.

According to one alternative embodiment, a predictor may be used instead of the processing model 5 for predicting the predicted images 50. In particular, a linear predictor may be used.

The predicted image data 49 are preferably denoised before the prediction. Such denoising may be carried out using different methods. These include conventional methods (filtering/BM3D) as well as machine learning methods (NOISE2NOISE/NOISE2VOID).

The predicted image data 49 are preferably normalized before the prediction, so that the image data to be processed all lie in a predetermined intensity range. The background suppression, described with reference to the above-described exemplary embodiments, may also take place before carrying out the prediction.

Identification of the analytes may either take place based on the stored difference images 51, in which case a processing model 5 that is used for this purpose must be trained to identify types of analytes, for example based on such difference images 51, or the images, as described above, are reconstructed, and the reconstructed data are used to identify the analytes, as described above.

A further embodiment according to aspect G of the machine learning system 1 likewise includes the microscope 2, the control device 3, and the evaluation unit 4.

Figure 11:
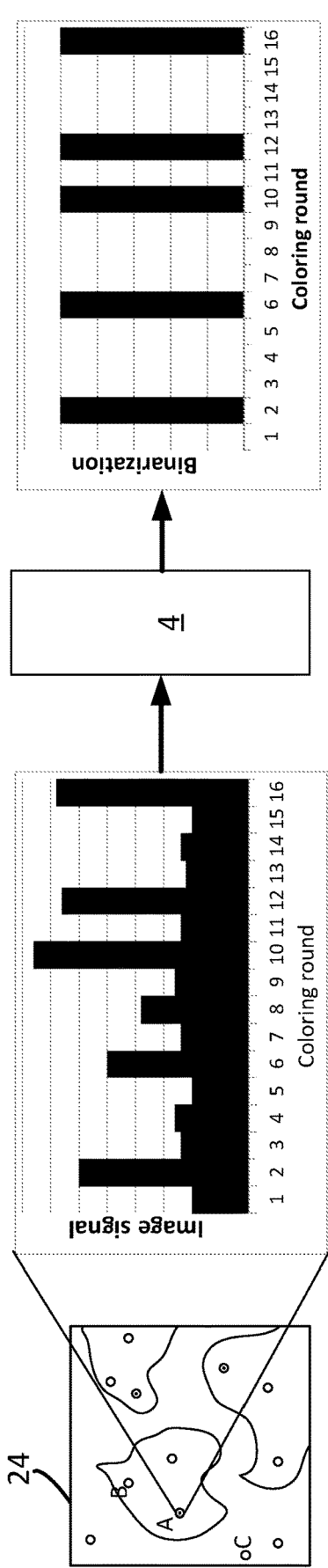

The evaluation unit 4 according to this exemplary embodiment corresponds to the exemplary embodiments explained above, for which reason identical parts are not described again, but differs from the evaluation units 4 according to the exemplary embodiments as per aspects A through F, in that the evaluation unit 4 includes a processing model 5 that has been trained to subject the color values of the pixels of the images of a sample to an assessment, the assessment indicating whether the color values correspond to a signal and/or to an uncolored signal, and to appropriately binarize the pixels, whose color values with a predetermined likelihood are either a colored signal or an uncolored signal; i.e., for the pixels, a binary value, i.e., a 0 or a 1, is stored instead of the color value, depending on whether the processing model 5 classifies the color value as a colored signal or as an uncolored signal (see FIG. 11, which illustrates by way of example a binarization of a complete experiment).

During storing of the color information, for the binarized pixels only the binary value is stored. For unbinarized pixels, for which the assessment of the color values still does not output an unambiguous result, i.e., the likelihood does not correspond to the predetermined likelihood, the color value continues to be stored. The unbinarized pixels may be reassessed in a later assessment, for example after one of the subsequent coloring rounds, when a new assessment shows that the previously unbinarized color values with the predetermined likelihood are either a colored signal or an uncolored signal, so that these initially unbinarized color values are also binarized, and for the pixels a binary value is stored instead of the color value.

The processing model 5 is, for example, a scoring model that has been trained to assess the color values. An annotated data set used in the training includes the binarized color values as input series of color values and as target output. In the training, the series of color values are input into the processing model 5, and an objective function detects a difference between an output of the processing model 5 and the target output.

The processing model 5 may also be configured to recognize the characteristic signature described with reference to aspect A, and based on the characteristic signature to assign a class to the color values, i.e., in the present case the classes "colored signal" or "uncolored signal," or a higher-level class when an unambiguous assignment is not or not yet possible.

According to this exemplary embodiment, after a new coloring round is recorded, in each case the color values of all previously carried out coloring rounds are input into the processing model 5, and the color values of the new coloring round as well as not yet binarized color values from previous coloring rounds are assessed.

The processing model 5 may be designed in such a way that in an experiment in which m coloring rounds are carried out, the processing model has m input channels, i.e., one input channel for each coloring round. For each of the input channels, the processing model 5 has an output channel which indicates the assessment. The assessment may be, for example, a likelihood between 0 and 1 that indicates whether the color value corresponds to a colored signal.

If only a few of the coloring rounds are recorded, for the input of the color values into the processing model 5, which takes place for the assessment, the color values for the coloring rounds that have not yet taken place are set to zero.

The input of the already binarized color values into the processing model 5 takes place in such a way that for the binarized color values the processing model 5 once again outputs in each case the corresponding binary value. For this purpose, the processing model 5 may be implemented in various ways.

For example, if the processing model 5 is designed in such a way that it receives inputs only in the value range between 0 and 1, the color values must accordingly be normalized prior to the input so that they lie between 0 and 1.

Alternatively, the processing model 5 may be designed in such a way that for each entry of the input, a further binarization control value is input which indicates whether or not the particular color value has been binarized. Accordingly, the processing model 5 processes the components of the inputs differently, depending on whether or not the inputs have already been binarized. For example, an already binarized color value that is stored as a "0" or "1," i.e., as a binary value containing only one bit and thus of a different quantization, may be input into the processing model 5 as 0 or a maximum value of the value range of the color values, corresponding to a value range of the color values, when the processing model 5 correspondingly reads in the binarization control value and determines that the color value has already been binarized. If the value range of the color values extends from 0 to 65.536, for example, and a color value is already binarized, the binarization control value is 1 and the binarized color value is 0, for example, the processing model reads in a 0 as the input value as a representative for the coloring round. If the binarized color value is 1, the processing model reads in 65.536 as the input value for the corresponding coloring round. If the particular color value has not yet been binarized, this is correspondingly indicated by the binarization control value; for example, the binarization control value is then 0, and the processing model specifically reads in the unbinarized color value for the particular coloring round.

The decision as to whether a color value with a predetermined likelihood represents a colored signal or an uncolored signal may be made by use of a measure of confidence or heuristics.

According to one alternative, the processing model 5 is designed as a classification model that is to assign either the class "colored signal" or "uncolored signal" to each of the color values. It has been shown that the assignment to one of the classes is not always unambiguous, specifically for early coloring rounds. Therefore, it is advantageous to introduce a third class which includes all color values that cannot be unambiguously assigned to the colored signal class or to the uncolored signal class, since the likelihood that the particular color value is a colored signal or an uncolored signals is too low.

As described above with reference to the previous embodiments, the processing model 5 may additionally read in context information that is used in the assessment of the color values. For example, the context information includes color values of the previous coloring rounds, statistical values of the previously carried out coloring rounds, one or more color values of background images, statistical values for the background, information concerning the number of expected analytes in a sample, a codebook used, or also a user ID.

For example, the context information used may also be a function of semantics of the recorded images. Accordingly, context information may also be read in based on a semantic segmentation.

If all color values of a data point or of a pixel have been assessed and possibly binarized, a type of analyte may be determined, based on the resulting (un)binarized color values, by comparison to a codebook, provided that a sufficiently large number of color values have been identified as colored signals.

According to one embodiment, after a complete binarization of a color value vector, multiplication by a codebook matrix takes place, the codebook matrix including a target bit sequence for all types of analytes to be identified. As a result of the matrix multiplication, for each of the target bit sequences in the codebook matrix a sum of the matching 1 entries between the completely binarized color vector and the particular target bit sequence of the codebook matrix is obtained.

If an experiment includes 16 coloring rounds, for example, and each of the types of analytes is encoded with five colored signals, for the correct type of analyte the result of multiplying the completely binarized color value vector by the codebook matrix should specifically result in a 5, since in the matrix multiplication the 1 entries of the binarized color value vector precisely match the 1 entries of the target bit sequence and are summed. For all nonmatching target bit sequences, the result of the matrix multiplication is less than 5.

Subsolution A

Example 1A of the invention relates to a method for preparing data for identifying analytes by coloring one or more analytes with markers in multiple coloring rounds, the markers in each case being specific for a certain set of analytes, detecting multiple markers using a camera (12), which for each coloring round generates at least one image (24) that contains multiple pixels and includes colored signals and uncolored signals, a colored signal being a pixel containing color information of a marker, and an uncolored signal being a pixel containing color information that is not based on a marker, and storing the images (24) of the particular coloring rounds for evaluating the color information, a data point in each case including one or more contiguous pixels in the images (24) of the multiple coloring rounds, which are assigned to the same location in a sample, characterized in that each of the data points is assessed, based on the color information of at least the present image (24), for whether it may be a candidate data point, i.e., that it may contain colored signals and may thus encode an analyte, and when the color information is stored, the color information of the data points of the images (24) which are reliably not a candidate data point, based on the assessment, is eliminated.

Example 2A of the invention relates to a method according to Example 1A, characterized in that each data point is also assessed, based on the color information of all previous coloring rounds and/or a subset of the previous coloring rounds and/or based on color information of neighboring data points, for whether the data point is a candidate data point.

Example 3A of the invention relates to a method according to Example 1A or 2A, characterized in that the data points are assessed using a processing model (5) of a machine learning system (1).

Example 4A of the invention relates to a method according to Example 3A, characterized in that the processing model (5) has been trained using an annotated data set, which includes multiple data points as input series of color information, and as a target output includes a classification of whether the particular series originates from a einem candidate data point or a background data point.

Example 5A of the invention relates to a method according to Example 4A, characterized in that the annotated data set has been obtained based on a portion of an experiment, so that the trained processing model (5) may be applied to the remaining portion of the experiment.

Example 6A of the invention relates to a method according to Example 4A or 5A, characterized in that after a new experiment, after identifying the analytes a further annotated data set is generated based on the compressed images that have been stored without the color information of the data points and that encode no analyte, wherein for a selection of the data points that encode no analyte, the color information is also stored, and the pieces of color information of the data points that encode no analyte are used as background data points in the further annotated data set, and the processing model (5) is trained using the further annotated data set.

Example 7A of the invention relates to a method according to one of Examples 1A through 6A, characterized in that an image (24) encompasses a two-dimensional depiction including multiple pixels as image points, or a three-dimensional depiction including multiple voxels as image points, wherein the images (24) may include time information as an additional dimension.

Example 8A of the invention relates to a method according to one of Examples 1A through 7A, characterized in that the processing model (5) is a classification model via which candidate data points and/or background data points are classified as binary, and/or the processing model (5) is a semantic segmentation model via which candidate data points and/or background data points are semantically segmented, and/or the processing model (5) is an image-to-image model that is trained in particular to output a heat map, via which likelihoods or densities of candidate data points and/or background data points are output.

Example 9A of the invention relates to a method according to one of Examples 1A through 7A, characterized in that the processing model (5) is a detection model that is trained to detect candidate data points, in particular a list of the coordinates of the candidate data points being output.

Example 10A of the invention relates to a method according to Example 9A, characterized in that the detection model is trained to detect the extent of the candidate data points, the output list including, in addition to the coordinates of the foreground data points, the extent of the particular candidate data points.

Example 11A of the invention relates to a method according to one of Examples 1A through 10A, characterized in that when the images (24) are stored after one of the coloring rounds, data points whose color information has already been eliminated after a preceding coloring round are not taken into account.

Example 12A of the invention relates to a method according to one of Examples 1A through 11A, characterized in that data points with color information for which, although their color values may be assessed as color values of a marker based on their intensity and/or their characteristic signature, the color values of these data points are not assignable to an analyte after several coloring rounds, since the series of color values assigned to the particular data point cannot correspond to any possible pattern or any possible series of color values for an analyte, are assessed as encoding no analyte.

Example 13A of the invention relates to a method according to Example 12A, characterized in that the checking of a series of color values of a pixel is carried out using a scoring model, the pixels with a characteristic signature being assessed as potential markers, and the series of color values of the potential markers being checked for whether they may correspond to a possible pattern of an analyte.

Example 14A of the invention relates to a method according to one of Examples 3A through 13A, characterized in that the processing model (5) is additionally supplied with context information as input data, the context information describing further properties of the sample and/or of the experiment and/or of the expected analytes, and in particular parameters for coloring the sample and/or the expected number of analytes or also the expected ratio of the analytes contained in the sample, and based on this context information, the sensitivity of the assessment of the data points being adjusted, and/or a processing model (5) being automatically selected from a set of processing models (5).

Example 15A of the invention relates to a method according to Example 14A, characterized in that the context information has been obtained via a segmentation, and in particular differentiates the cell areas from areas that are not assigned to a cell.

Example 16A of the invention relates to a method according to one of Examples 3A through 15A, characterized in that the sensitivity of the processing model (5), which is used to assess whether a data point may be a candidate data point, is varied for the different coloring rounds, in particular a higher sensitivity being applied in the first coloring rounds than in the later coloring rounds.

Example 17A of the invention relates to a method according to one of Examples 1A through 16A, characterized in that the order of the coloring rounds is selected in such a way that the number of measured markers is maximized in early rounds.

Example 18A of the invention relates to a method according to one of Examples 1A through 17A, characterized in that the images (24) are stored in one of the following formats:

background data points that encode no analyte are set to a certain value, in particular "0," wherein areas of the images (24) whose pixels are assigned the same value are compressed during storage, a binary array, in which storage is carried out in an array, using only one bit, regardless of whether a foreground data point or background data point is involved, wherein an additional list may be stored in which all color values of the foreground data points are continuously stored, and an assignment of the foreground data points of the array to the color values of the list takes place by use of an index, a sparse matrix that includes a list containing coordinates and color values of all foreground data points and optionally their extent.

Example 19A of the invention relates to a method according to Example 18A, characterized in that the images (24) of the different coloring rounds are stored using different formats, in particular the images (24) of the first coloring rounds being stored in a compressed image format and the images (24) of the subsequent coloring rounds being stored as a sparse matrix or as a binary array.

Example 20A of the invention relates to a method according to one of Examples 1A through 19A, characterized in that the analytes are one of the following: proteins, polypeptides, or nucleic acid molecules, and the markers couple to the analytes via analyte-specific probes and include a dye molecule that is coupled to the marker.

Example 21A of the invention relates to a method according to Example 20A, characterized in that the markers of the first coloring round or of the first and second coloring rounds have shorter oligonucleotide sequences than in the subsequent coloring rounds, the oligonucleotide sequences of the markers of the first or the first and second coloring rounds containing no more than 10 nucleotides.

Example 22A of the invention relates to a method according to one of Examples 1A through 21A, characterized in that the analytes are identified based on the determined color information.

Example 23A relates to a method according to one of Examples 1A through 22A, characterized in that the method, prior to the preparation of data for identifying analytes, also includes a step of carrying out a background correction of the image signals of the image series, the carrying out of the background correction including one or more of the following:

a rolling ball method, filtering, for example a top hat method, homomorphous filtering, low pass filtering, wherein the result of the low pass filtering is subtracted from the signal, or temporal filtering, background correction by use of an image-to-image model, background correction by use of mixed models, background correction by use of a mean shift method, background correction by use of principal component analysis, background correction by use of non-negative matrix factorization, background correction by the excitation of autofluorescence by use of at least one specific laser for all image areas of the image series, wherein the specific laser corresponds specifically to one excitation spectral range of one of the markers used, and the analytes are not yet marked with markers, or background correction by the excitation of autofluorescence by use of a nonspecific laser for all data points of the image series.

Example 24A of the invention relates to a method for training a machine learning system, using a processing model for carrying out a method according to one of Examples 1A through 23A, comprising:

providing an annotated data set, and optimizing an objective function by adapting the model parameters of the processing model (5), the objective function detecting a difference between a result output (30) that is output by the processing model (5) and a target output, characterized in that the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.

Example 25A of the invention relates to an evaluation unit (4) for evaluating images (24) of multiple coloring rounds, and which in particular is designed as a machine learning system (1), including the means for carrying out the method according to one of the preceding examples.

Example 26A of the invention relates to an image processing system (1), including an evaluation unit (4) according to preceding Example 25A, in particular including an image generation unit such as a microscope (2).

Example 27A of the invention relates to a computer program product that includes commands which, when the program is executed by a computer, prompt the computer to carry out the method according to one of preceding Examples 1A through 24A, the computer program product being in particular a computer-readable memory medium.

Example 28A of the invention relates to a machine learning system (1) that includes an evaluation unit (4), the evaluation unit (4) including a processing model that has been trained according to the method according to preceding Example 24A, in particular including an image generation unit such as a microscope (2).

Subsolution B

Example 1B of the invention relates to a method for preparing data for identifying analytes in a sample, in which in an experiment one or more analytes are colored with markers in multiple coloring rounds, the markers in each case being specific for a certain set of analytes, detecting the multiple markers using a camera, which for each coloring round generates at least one image (24) containing multiple pixels and color values assigned thereto, the image (24) including colored signals and uncolored signals, wherein a colored signal is a pixel having a color value that originates from a marker, and an uncolored signal is a pixel having a color value that is not based on a marker, and storing the color information of the particular coloring rounds for evaluating the color information, a data point in each case including one or more contiguous pixels in the images (24) of the multiple coloring rounds that are assigned to the same location in a sample, characterized in that for each data point of the multiple images (24) of the sample, the particular color values are assessed for whether they represent a colored signal in each case and accordingly encode an analyte, and the n color values of the different coloring rounds that most likely represent a colored signal are selected for each data point, where n is an integer that is less than the total number of coloring rounds of an experiment, and when the color information is stored, the color values that are not selected are omitted.

Example 2B of the invention relates to a method according to Example 1B, characterized in that the n color values are selected using a scoring model of a machine learning system (1), the scoring model being trained on criteria for assessing the color values for whether they represent a colored signal.

Example 3B of the invention relates to a method according to Example 2B, characterized in that after each coloring round the color values of the data points are assessed, and the color information recorded in the present coloring round is stored, and the maximum n color values that have been output by the scoring model after an immediately preceding coloring round, as well as the color value of the data point recorded in the coloring round, are entered into the scoring model as input for a data point, and the scoring model assesses the input color values, and n color values are selected based on the assessment, and the color value that least likely represents a colored signal is sorted out.

Example 4B of the invention relates to a method according to Example 2B, characterized in that after each coloring round the data points are assessed and the image (24) recorded in the present coloring round is stored, and only the color information of the presently recorded image (24) is input into the scoring model.

Example 5B of the invention relates to a method according to one of Examples 2B through 4B, characterized in that the scoring model has been trained using an annotated data set, which as input data contains images (24) or the color values of the pixels and corresponding target outputs, each of which defines whether the color values represent a colored signal and/or an uncolored signal.

Example 6B relates to a method according to Example 5B, characterized in that the annotated data set is created using a method in which the images (24) of the multiple coloring rounds together with their color values are stored in uncompressed form and then evaluated, in the training, for each coloring round the maximum n color values, which may represent a colored signal according to predetermined criteria, and the color value of the data point obtained in the particular coloring round being entered into the processing model as input for a data point, computing an objective function, the objective function detecting a difference between the n color values that are output by the processing model (5) which most likely represent a colored signal, and the n color values to be selected according to the annotated data set, which according to the assessment in the annotated data set most likely represent a colored signal, and optimizing the objective function by adapting the model parameters.

Example 7B of the invention relates to a method according to Example 5B or 6B, characterized in that the annotated data set has been generated via one or more of the following steps: simulating signals of the various markers using a representative background image and a known point spread function of a microscope (2), generating the annotated data set by use of a generative model that has been trained on comparable data, recording reference images that include at least one background image, and for each of the background images for each type of analyte, recording at least one image (24) in which analytes of the particular type of analyte are marked, carrying out a conventional method for spatial identification of analytes, recording a representative background image and subtracting, pixel by pixel, the image signals of the representative background image from the image signals of the image series on which the annotated data set is based, before providing the annotated data set, so that the annotated data set includes only background-corrected color values, and/or obtaining the annotated data set based on a portion of an experiment, so that the trained scoring model may be applied to the remaining portion of the experiment.

Example 8B of the invention relates to a method according to one of Examples 1B through 7B, characterized in that the data points for selecting the n color values are assessed, according to predetermined criteria, for whether they represent a colored signal, taking into account the following criteria: the intensity, the color, and/or the extent of the data point.

Example 9B of the invention relates to a method according to one of Examples 6B through 8B, characterized in that the criteria for selecting the n color values include threshold values for a minimum and/or maximum intensity, the threshold values being statically specified or dynamically determined, and/or the threshold values for a minimum and/or maximum intensity varying as a function of the color of the color values, and/or the threshold values are determined via a minimum distance from predetermined target values of the intensity, color, and/or extent.

Example 10B of the invention relates to a method according to one of Examples 1B through 9B, characterized in that additional information is stored, for example statistical information concerning all color values of a particular data point and/or concerning the nonselected color values of one of the data points and/or concerning the selected color values of one of the data points, for example information concerning the coloring round (number, point in time, etc.), and/or a sliding average value, a standard deviation, and/or a median of a property of the color information of the particular data point or of the color information of multiple data points, wherein the properties of the color information encompass in particular the intensity, color, and/or extent.

Example 11B of the invention relates to a method according to one of Examples 1B through 10B, characterized in that one of the analytes is colored with i markers in m coloring rounds, and the number n of the selected color values for each data point is n=i+a, where i+a is less than the total number of m coloring rounds, and a is an integer between 0 and 3 and is preferably determined automatically based on semantics.

Example 12B of the invention relates to a method according to one of Examples 1B through 11B, characterized in that an image (24) encompasses a two-dimensional image (24) including multiple pixels as image points, or a three-dimensional image (24) having multiple pixels as image points, wherein the images may contain time information as an additional dimension.

Example 13B of the invention relates to a method according to one of Examples 1B through 12B, characterized in that n is not greater than one-half, and in particular not greater than one-third, of the total number of coloring rounds of an experiment.

Example 14B of the invention relates to a method according to one of Examples 5B through 13B, characterized in that the scoring model is a convolutional neural network (CNN), a multilayer perceptron (MLP), or a sequential model.

Example 15B of the invention relates to a method according to one of Examples 1B through 14B, characterized in that the color information is stored in one of the following formats:

for the data points, only the selected color values with and without additional information are stored, for the data points, only the selected color values, in each case together with an index that indicates from which coloring round the particular color value originates, with and without additional information are stored, the detected images are stored, the nonselected color values being set to a predetermined fill value, for example "0."

Example 16B of the invention relates to a method according to one of Examples 1B through 15B, characterized in that the analytes are identified based on the selected, stored color values.

Example 17B of the invention relates to a method according to Example 16B, characterized in that after the analytes are identified, and optionally after a manual correction, an appropriately expanded annotated data set is created, and the processing model (5) is trained using the expanded annotated data set.

Example 18B of the invention relates to a method according to one of Examples 1B through 17B, characterized in that the method also includes, prior to the preparation of data for identifying analytes, a step of carrying out a background correction of the color values, the carrying out of the background correction including one or more of the following:

a rolling ball method, filtering, for example a top hat method, homomorphous filtering, low pass filtering, wherein the result of the low pass filtering is subtracted from the signal, or temporal filtering, background correction by use of an image-to-image model, background correction by use of mixed models, background correction by use of a mean shift method, background correction by use of principal component analysis, background correction by use of non-negative matrix factorization, background correction by the excitation of autofluorescence by use of at least one specific laser for all image areas of the image series, wherein the specific laser corresponds specifically to one excitation spectral range of one of the markers used, and the analytes are not yet marked with markers, or background correction by the excitation of autofluorescence by use of a nonspecific laser for all data points of the images.

Example 19B of the invention relates to a method according to one of Examples 2B through 188, characterized in that additional context information that describes further properties of the sample and/or of the experiment and/or of the expected analytes is supplied to the scoring model as input data, and may include in particular parameters for coloring the sample and/or the expected number of analytes or also the expected ratio of the analytes contained in the sample.

Example 20B of the invention relates to a method according to one of Examples 2B through 19B, characterized in that additional context information is used to select a suitable scoring model from a plurality of different pretrained scoring models, wherein the context information describes further properties of the sample and/or of the experiment and/or of the expected analytes, and in particular may include parameters for coloring the sample and/or the expected number of analytes or also the expected ratio of the analytes contained in the sample.

Example 21B of the invention relates to a method according to Example 19B or 20B, characterized in that the context information is obtained by segmentation, and in particular cell areas may be differentiated from areas that are not assigned to a cell.

Example 22B of the invention relates to a method for training a machine learning system, using a processing model for carrying out a method according to one of Examples 1B through 21B, comprising:

providing an annotated data set, and optimizing an objective function by adapting the model parameters of the processing model (5), the objective function detecting a difference between a result output (30) that is output by the processing model (5) and a target output, characterized in that the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.

Example 23B of the invention relates to an evaluation unit (4) for evaluating images (24) of multiple coloring rounds, and which in particular is designed as a machine learning system (1), including the means for carrying out the method according to one of the preceding examples.

Example 24B of the invention relates to an image processing system (1), including an evaluation unit (4) according to preceding Example 22B, in particular including an image generation unit such as a microscope (2).

Example 25B of the invention relates to a computer program product that includes commands which, when the program is executed by a computer, prompt the computer to carry out the method according to one of preceding Examples 1B through 22B, the computer program product being in particular a computer-readable memory medium.

Example 26B of the invention relates to a machine learning system (1) that includes an evaluation unit (4), the evaluation unit (4) including a processing model that has been trained according to the method according to Example 22B, in particular including an image generation unit such as a microscope (2).

Subsolution C

Example 1C of the invention relates to a method for preparing data for identifying analytes by coloring one or more analytes with markers in multiple coloring rounds, the markers in each case being specific for a certain set of analytes, detecting multiple markers using a camera, which for each coloring round generates at least one image containing multiple pixels and color values assigned thereto, which may contain color information of one or more markers, and storing the color information of the particular coloring rounds for evaluating the color information, a data point in each case including one or more contiguous pixels in the images of the multiple coloring rounds that are assigned to the same location in a sample, characterized in that for each data point of a sample, the color value for one of n coloring rounds of an experiment is recorded in each case, and these color values in each case form a component of an output vector having the dimension m, after recording the corresponding color value the individual vector components (38) being projected onto a projection vector having a dimension k that is smaller than m, and the projection vector for each coloring round being sequentially aggregated onto an aggregation vector (40) having the same dimension k as the projection vector, and the aggregation vector (40) is stored.

Example 2C of the invention relates to a method according to Example 1C, characterized in that the projection is a linear projection, and the aggregation for the aggregation vector (40) is a summation, and in particular is a principal axis transformation or a singular value decomposition (SVD).

Example 3C of the invention relates to a method according to Example 1C, characterized in that the projection is a nonlinear projection, and the aggregation for the aggregation vector (40) is a summation or a multiplication of the components.

Example 4C of the invention relates to a method according to Example 2C, characterized in that the projection is a principal axis transformation, and the bases and the transformation matrix are analytically computed or estimated from the data of a preceding experiment and/or background image or the expected ideal codes.

Example 5C of the invention relates to a method according to Example 4C, characterized in that the principal axis transformation is a transformation from the m-dimensional output space to an m-dimensional target space, and a k-dimensional projection space is a subspace of the target space, and the k components of the projection vectors correspond to the k dimensions of the projection space, and (m–k)=j components in the target space are omitted to obtain the projection space from the target space, and the omitted j components include in particular at least one of the following components:

the last component, the last components, the first component, or the first and the last component.

Example 6C of the invention relates to a method according to one of Examples 1C through 5C, characterized in that the projection is carried out using a processing model (5).

Example 7C of the invention relates to a method according to Example 6C, characterized in that the processing model (5) is formed from a neural network, and in particular is formed as a convolutional neural network (CNN).

Example 8C of the invention relates to a method according to Example 6C or 7C, characterized in that the processing model (5) has c input strings, each having d input channels, and the c input strings share k output channels, the outputs of the individual input strings in the k output channels being aggregated channel by channel, where d is preferably the number of various color channels used in the detection, and c*d=m, where m is the number of coloring rounds and c is a proportionality factor between the number of coloring rounds m and the number of color channels d used.

Example 9C of the invention relates to a method according to Example 6C or 7C, characterized in that the processing model (5) has been trained using an annotated data set, which is supplied with one of the data points as input vectors for computing the aggregation vector (40), in which an ith vector element of the color value of the data point is the ith coloring round, and the remaining vector elements are 0, and an objective function detects the difference between a target output and the aggregation vectors (40), the target output being computed from the input vectors using a dimensionally reducing transformation, in particular a linear or nonlinear projection, the transformed input vectors being sequentially aggregated with one another to form the aggregation vector (40).

Example 10C of the invention relates to a method according to Example 9C, characterized in that the processing model (5) is trained separately for each vector component (38) of the input vector.

Example 11C of the invention relates to a method according to one of Examples 6C through 10C, characterized in that a processing model (5) is pretrained independently of the experiment to be carried out, or processing models (5) are pretrained for different types of experiments, and context information concerning the type of particular experiment is used to automatically select the most suitable processing model (5).

Example 12C of the invention relates to a method according to one of Examples 1C through 11C, characterized in that the analytes are identified based on the determined color information, prior to the identification the stored aggregation vectors (40) being back-transformed, so that the color values of the particular coloring rounds are restored in the original version.

Example 13C of the invention relates to a method according to one of Examples 1C through 11C, characterized in that the analytes are identified based on the transformed and stored color information, the series of color values that have the same projection as the recorded color values, which in each case are typical for the analytes to be detected, being projected beforehand onto a particular result vector having the dimension k, and the identification of the analyte taking place based on a comparison of the aggregation vector (40) to the result vector for the particular data point.

Example 14C of the invention relates to a method according to Example 13C, characterized in that the comparison of the aggregation vector to the result vector is carried out using an identification processing model that has been trained using an annotated data set, which as an input data set includes aggregation vectors (40) and result vectors of experiments in which the analytes have been identified in a conventional manner.

Example 15C of the invention relates to a method according to Examples 1C through 11C, wherein the aggregation vector (40) is input into an identification processing model, which as a classification network has been trained to assign the aggregation vector (40) to a class comprising various types of analytes, or has been trained to output a result bit sequence, the result bit sequence being compared to the bit sequences that are typical in each case for the analytes to be detected in order to identify a type of analyte.

Example 16C of the invention relates to a method according to one of Examples 1C through 15C, characterized in that the output vectors are subjected to a background correction prior to the projection.

Example 17C of the invention relates to a method according to one of Examples 1C through 16C, characterized in that an image encompasses a two-dimensional depiction including multiple pixels as image points, or a three-dimensional depiction including multiple voxels as image points, at least one pixel of each image being assignable to each data point of a sample, wherein the images may include time information as an additional dimension.

Example 18C of the invention relates to a method according to one of Examples 1C through 16C, characterized in that each data point is a pixel of each image or a group of contiguous pixels.

Example 19C of the invention relates to a method according to one of Examples 1C through 18C, characterized in that the images are presegmented in various semantic areas, and for different semantic areas, different projections are used for transforming the output vectors to aggregation vectors (40).

Example 20C of the invention relates to a method according to Example 19C, characterized in that the different projections are principal axis transformations which differ in the bases and the transformation matrices.

Example 21C of the invention relates to a method according to one of Examples 1C through 20C, characterized in that the analytes are one of the following: proteins, polypeptides, or nucleic acid molecules, and the markers couple to the analytes via analyte-specific probes and include a dye molecule that is coupled to the marker.

Example 22C of the invention relates to a method for training a machine learning system, using a processing model for carrying out a method according to one of Examples 1C through 21C, comprising:

providing an annotated data set, and optimizing an objective function by adapting the model parameters of the processing model (5), the objective function detecting a difference between a result output (30) that is output by the processing model (5) and a target output, characterized in that the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.

Example 23C of the invention relates to an evaluation unit (4) for evaluating images (24) of multiple coloring rounds, and which in particular is designed as a machine learning system (1), including the means for carrying out the method according to one of the preceding examples.

Example 24C of the invention relates to an image processing system (1), including an evaluation unit (4) according to preceding Example 23C, in particular including an image generation unit such as a microscope (2).

Example 25C of the invention relates to a computer program product that includes commands which, when the program is executed by a computer, prompt the computer to carry out the method according to one of preceding Examples 1C through 23C, the computer program product being in particular a computer-readable memory medium.

Example 26C of the invention relates to a machine learning system (1) that includes an evaluation unit (4), the evaluation unit (4) including a processing model that has been trained according to the method according to Example 22C, in particular including an image generation unit such as a microscope (2).

Subsolution D

Example 1D of the invention relates to a method for preparing data for identifying analytes by coloring one or more analytes with markers in multiple coloring rounds, the markers in each case being specific for a certain set of analytes, detecting multiple markers using a camera, which for each coloring round generates at least one image (24) that includes multiple pixels and that may contain color information of one or more markers, and storing the images of the particular coloring rounds stored for evaluating the color information, characterized in that the color values determined in the individual coloring rounds are clustered, according to their intensity values, in local or global clusters (43) with similar intensity values, and only the clustered data are stored.

Example 2D of the invention relates to a method according to Example 1 D, characterized in that after each coloring round, the intensity values are reclustered as an additional feature dimension, using the newly obtained color information.

Example 3D of the invention relates to a method according to Example 1 D or 2D, characterized in that for every pixel, a cluster ID is stored that describes to which cluster (43) the particular pixel belongs.

Example 4D of the invention relates to a method according to one of Examples 1 D through 3D, characterized in that the intensity value of each coloring round is stored for each cluster (43).

Example 5D of the invention relates to a method according to one of Examples 1 D through 4D, characterized in that a sliding statistical value, in particular an average value and/or a variance and/or a median and/or a central color value, is stored for each cluster (43).

Example 6D of the invention relates to a method according to Example 1 D, characterized in that each image (24) of a coloring round is clustered separately.

Example 7D of the invention relates to a method according to one of Examples 1 D through 6D, characterized in that the clustering is carried out using a partitioning, hierarchical, graph-theoretical, or optimizing cluster method.

Example 8D of the invention relates to a method according to one of Examples 1 D through 7D, characterized in that the clustering is carried out using a supervised or unsupervised cluster method.

Example 9D of the invention relates to a method according to one of Examples 1 D through 8D, characterized in that intensity values which deviate by a predetermined threshold value from a central intensity value of the particular cluster (43) are stored separately in order to generate a new cluster (43) as needed.

Example 10D of the invention relates to a method according to one of Examples 1 D through 9D, characterized in that local clusters (43) are generated, one of the image features for the clustering being intensity values, and a further image feature for the clustering being the position of the particular pixels in the image (24).

Example 11D of the invention relates to a method according to one of Examples 1 D through 10D,
characterized in that
an image (24) encompasses a two-dimensional depiction including multiple pixels as image points, or a three-dimensional depiction including multiple voxels as image points, at least one pixel of each image (24) being assignable to each measuring point of a sample, wherein the images (24) may include time information as an additional dimension.
Example 12D of the invention relates to a method according to one of Examples 1 D through 11D,
characterized in that
certain clusters (43) are unambiguously assigned to a certain analyte, so that the analytes may be identified by reading out the clusters (43) in question.
Example 13D of the invention relates to a method according to one of Examples 1 D through 12D,
characterized in that
for identifying the analytes, the series of intensity values that are stored for the individual clusters (43) and quantized by the clustering are compared to the series of target intensity values that encode the particular analytes, the target intensity values preferably being quantized beforehand to the same value range as the clusters (43).
Example 14D of the invention relates to a method according to one of Examples 1 D through 13D,
characterized in that
the identification of the analytes based on the clusters (43) is carried out using a processing model (5), this processing model (5) preferably being a classification model.
Example 15D of the invention relates to a method according to one of Examples 1 D through 14D,
characterized in that
the clustering is carried out using a processing model (5).
Example 16D of the invention relates to a method according to Example 15D,
characterized in that
the processing model (5) for the clustering is a segmentation model and in particular is a semantic segmentation model.
Example 17D of the invention relates to a method according to Example 15D or 16D,
characterized in that
additional context information that describes further properties of the sample and/or of the experiment and/or of the expected analytes is supplied as input data to the processing model (5), and in particular may include parameters for coloring the sample and/or the expected number of analytes, or also the expected ratio of the analytes contained in the sample, the quantization of the clustering being set based on this context information.
Example 18D of the invention relates to a method according to one of Examples 1 D through 17D,
characterized in that
the analytes are one of the following: proteins, polypeptides, or nucleic acid molecules, and the markers couple to the analytes via analyte-specific probes and include a dye molecule that is coupled to the marker.
Example 19D of the invention relates to a method for training a machine learning system, using a processing model for carrying out a method according to one of Examples 1D through 18D, comprising:

providing an annotated data set, and
optimizing an objective function by adapting the model parameters of the processing model (5), the objective function detecting a difference between a result output (30) that is output by the processing model (5) and a target output, characterized in that
the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.
Example 20D of the invention relates to an evaluation unit (4) for evaluating images (24) of multiple coloring rounds, and which in particular is designed as a machine learning system (1), including the means for carrying out the method according to one of the preceding examples.
Example 21D of the invention relates to an image processing system (1), including an evaluation unit (4) according to preceding Example 20D, in particular including an image generation unit such as a microscope (2).
Example 22D of the invention relates to a computer program product that includes commands which, when the program is executed by a computer, prompt the computer to carry out the method according to one of preceding Examples 1D through 19D, the computer program product being in particular a computer-readable memory medium.
Example 23D of the invention relates to a machine learning system (1) that includes an evaluation unit (4), the evaluation unit (4) including a processing model that has been trained according to the method according to Example 19D, in particular including an image generation unit such as a microscope (2).

Subsolution E

Example 1E of the invention relates to a method for preparing data for identifying analytes by coloring one or more analytes with markers in multiple coloring rounds, the markers in each case being specific for a certain set of analytes, detecting multiple markers using a camera, which for each coloring round detects at least one image that may contain color information of one or more markers, and storing the color information of the particular coloring rounds for evaluating the color information,
characterized in that
the images are subdivided into quantization regions in which the intensity values of the pixels are encoded with a different quantization in each case, and the quantized intensity values of the pixels are stored as color information.
Example 2E of the invention relates to a method according to Example 1E,
characterized in that
a certain bit depth is assigned to each of the quantizations, this depth, at least for certain quantization regions, being less than a bit depth of a quantization with which the intensity values detected by the camera are recorded.
Example 3E of the invention relates to a method according to Example 1E or 2E,
characterized in that different bit depths are applied in the different quantization regions.

Example 4E of the invention relates to a method according to one of Examples 1 E through 3E, characterized in that the quantization regions are divided according to one or more of the following method steps:

the quantization regions are established beforehand via intensity limits, so that each quantization region corresponds to a certain intensity range;

the images are semantically divided into different quantization regions;

the frequency of the individual intensity values is detected, and the quantization regions are established via intensity limits situated around frequency peaks;

the quantization regions are established by clustering similar intensity values; and/or the quantization regions are established by semantic segmentation of the images, for example in the background, cell, and cell nucleus.

Example 5E of the invention relates to a method according to one of Examples 1 E through 4E, characterized in that the quantization regions are divided at the following points in time:

once before the first quantization of one of the images (24), the division of the quantization regions preferably being carried out using a background image that is generated without markers, after the first coloring round, the quantization regions being divided based on a portion of the image detected during the first coloring round or based on the overall image, after multiple coloring rounds in each case, the quantization regions being divided based on a portion of the image detected during the particular coloring round or based on the overall image, or after each coloring round, the quantization regions being divided based on a portion of the image detected during the particular coloring round or based on the overall image.

Example 6E of the invention relates to a method according to Example 5E, characterized in that areas of an image (24) that are particularly suitable for dividing the quantization regions are automatically determined, in particular areas being determined that include multiple different quantization regions.

Example 7E of the invention relates to a method according to one of Examples 1 E through 6E, characterized in that the quantization regions form different intensity ranges, wherein the intensity values of the darkest intensity range are quantized most roughly, or only a single intensity value is assigned to all pixels of this intensity range.

Example 8E of the invention relates to a method according to Example 7E, characterized in that three quantization regions are used, each of which forms different intensity ranges, wherein the intensity range having average intensity values (47) is finely quantized, and the intensity range having bright intensity values (48) is quantized more roughly than the intensity range having average intensity values (47), and is preferably quantized more finely than the intensity range having dark intensity values.

Example 9E of the invention relates to a method according to one of Examples 1 E through 8E, characterized in that an image (24) encompasses a two-dimensional depiction including multiple pixels as image points, or a three-dimensional depiction including multiple voxels as image points, at least one pixel of each image being assignable to each measuring point of a sample, wherein the images (24) may include time information as an additional dimension.

Example 10E of the invention relates to a method according to one of Examples 1E through 9E, characterized in that for identifying the analytes, the stored quantized series of intensity values are compared to the series of target intensity values that encode the particular analyte.

Example 11E of the invention relates to a method according to Example 10E, characterized in that prior to the comparison, the target intensity values that encode the analytes are quantized in the same way as for the detected color information.

Example 12E of the invention relates to a method according to Example 10E, characterized in that prior to the comparison, the quantization of the stored quantized series of intensity values is eliminated to allow a comparison of the intensity values to the target intensity values that encode the analytes.

Example 13E of the invention relates to a method according to one of Examples 1E through 12E, characterized in that the analytes are one of the following: proteins, polypeptides, or nucleic acid molecules, and the markers couple to the analytes via analyte-specific probes and include a dye molecule that is coupled to the marker.

Example 14E of the invention relates to a method for training a machine learning system, using a processing model for carrying out a method according to one of Examples 1E through 13E, comprising:

providing an annotated data set, and optimizing an objective function by adapting the model parameters of the processing model (5), the objective function detecting a difference between a result output (30) that is output by the processing model (5) and a target output, characterized in that the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.

Example 15E of the invention relates to an evaluation unit (4) for evaluating images (24) of multiple coloring rounds, and which in particular is designed as a machine learning system (1), including the means for carrying out the method according to one of the preceding examples.

Example 16E of the invention relates to an image processing system (1), including an evaluation unit (4) according to preceding Example 15E, in particular including an image generation unit such as a microscope (2).

Example 17E of the invention relates to a computer program product that includes commands which, when the program is executed by a computer, prompt the computer to carry out the method according to one of preceding Examples 1E through 14E, the computer program product being in particular a computer-readable memory medium.

Example 18E of the invention relates to a machine learning system (1) that includes an evaluation unit (4), the evaluation unit (4) including a processing model that has been trained according to the method according to Example 14E, in particular including an image generation unit such as a microscope (2).

Subsolution F

Example 1F of the invention relates to a method for preparing data for identifying analytes in a sample, one or more analytes being colored with markers in multiple coloring rounds in an experiment, the markers in each case being specific for a certain set of analytes, the multiple markers being detected using a camera, which for each coloring round generates at least one image (24) that may contain color information of one or more markers, and the color information of the particular coloring rounds being stored for the evaluation, characterized in that for an nth coloring round, an expected predicted image (50) is predicted based on predicted image data (49) of one or more preceding coloring rounds and/or based on predicted image data (49) of the present coloring round, and a difference image (51) is formed on the one hand from an actually detected image (24) or from an actually detected image plane of the present coloring round, and on the other hand a difference image (51) is formed from the predicted image (50), the difference image (51) being stored as color information.

Example 2F of the invention relates to a method according to Example 1F, characterized in that the predicted image (50) corresponds to an image plane of a Z image made up of multiple image planes, and the predicted image data (49) include one or more image planes of Z images made up of one or more preceding coloring rounds and/or one or more image planes of the Z image of the present coloring round.

Example 3F of the invention relates to a method according to Example 1F or 2F, characterized in that the preceding coloring rounds are coloring rounds of the same experiment, or coloring rounds of a different experiment with preferably a similar or identical sample.

Example 4F of the invention relates to a method according to one of Examples 1F through 3F, characterized in that the predicted image data (49) include subsets of the images (24) of one or more preceding coloring rounds and/or of the present coloring round, wherein the subsets may be individual or multiple image planes of a Z image, or also excerpts in a plane of the images (24).

Example 5F of the invention relates to a method according to one of Examples 1F through 4F, characterized in that the predicted image data (49) are reconstructed image data from difference images (51), or only the difference images (51) themselves from preceding coloring rounds.

Example 6F of the invention relates to a method according to one of Examples 1F through 5F, characterized in that the predicted image data (49) are kept in compressed form.

Example 7F of the invention relates to a method according to one of Examples 1F through 5F, characterized in that the predicted image data (49) originate solely from the immediately preceding coloring round and/or from the present coloring round.

Example 8F of the invention relates to a method according to one of Examples 1F through 6F, characterized in that the difference image (51) is compressed before being stored.

Example 9F of the invention relates to a method according to one of Examples 1F through 7F, characterized in that the prediction is carried out using a predictor, in particular a linear predictor.

Example 10F of the invention relates to a method according to one of Examples 1F through 7F, characterized in that the prediction is carried out using a processing model (5) of a machine learning system (1), in particular of a neural network, for the image-to-image regression.

Example 11F of the invention relates to a method according to Example 9F, characterized in that the processing model (5)

is retrained for each coloring round, or is retrained for each experiment, or a processing model (5) is selected from multiple pretrained processing models (5), this selection preferably being made based on context information, which may include properties of the sample and/or of the experiment and/or of the expected analytes, and in particular parameters for coloring the sample and/or the expected number of analytes or also the expected ratio of the analytes contained in the sample.

Example 12F of the invention relates to a method according to Example 10F or 11F, characterized in that the processing model (5) has been trained using annotated training data, the annotated training data in each case including an output image and a corresponding target image, the output image as well as the target image having been measured for a sample.

Example 13F of the invention relates to a method according to one of Examples 1F through 12F, characterized in that the predicted image data (49) are normalized prior to the prediction, for example to have a predetermined intensity range and/or a defined background signal.

Example 14F of the invention relates to a method according to one of Examples 1F through 13F, characterized in that the predicted image data (49) are denoised prior to the prediction.

Example 15F of the invention relates to a method according to one of Examples 1F through 14F, characterized in that an image encompasses a two-dimensional depiction including multiple pixels as image points, or a three-dimensional depiction including multiple voxels as image points, wherein the images may include time information as an additional dimension.

Example 16F of the invention relates to a method according to one of Examples 1F through 15F, characterized in that for identifying the analytes by use of the stored difference images (51), the actually detected image (24) or the actually detected image plane is restored from same, at least for predetermined data points, wherein a data point in each case includes one or more contiguous pixels in the images of the multiple coloring rounds that are assigned to the same location in a sample.

Example 17F of the invention relates to a method according to one of Examples 1F through 16F, characterized in that the analytes are one of the following: proteins, polypeptides, or nucleic acid molecules, and the markers couple to the analytes via analyte-specific probes and include a dye molecule that is coupled to the marker.

Example 18F of the invention relates to a method for training a machine learning system, using a processing model for carrying out a method according to one of Examples 1F through 17F, comprising:

providing an annotated data set, and optimizing an objective function by adapting the model parameters of the processing model (5), the objective function detecting a difference between a result output (30) that is output by the processing model (5) and a target output, characterized in that the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.

Example 19F of the invention relates to an evaluation unit (4) for evaluating images (24) of multiple coloring rounds, and which in particular is designed as a machine learning system (1), including the means for carrying out the method according to one of the preceding examples.

Example 20F of the invention relates to an image processing system (1), including an evaluation unit (4) according to preceding Example 19F, in particular including an image generation unit such as a microscope (2).

Example 21F of the invention relates to a computer program product that includes commands which, when the program is executed by a computer, prompt the computer to carry out the method according to one of preceding Examples 1F through 18F, the computer program product being in particular a computer-readable memory medium.

Example 22F of the invention relates to a machine learning system (1) that includes an evaluation unit (4), the evaluation unit (4) including a processing model that has been trained according to the method according to Example 18F, in particular including an image generation unit such as a microscope (2).

Subsolution G

Example 1G of the invention relates to a method for preparing data for identifying analytes by coloring one or more analytes with markers in multiple coloring rounds, the markers in each case being specific for a certain set of analytes, detecting multiple markers using a camera, which for each coloring round generates at least one image (24) that includes multiple pixels to which a color value is assigned in each case as color information, and includes colored signals and uncolored signals, wherein a colored signal is a pixel containing color information of a marker, and an uncolored signal is a pixel containing color information that is not based on a marker, and storing the color information of the particular coloring rounds for evaluating and storing the color information of the particular coloring rounds for evaluating the color information, and a data point in each case includes one or more contiguous pixels in the images (24) of the multiple coloring rounds that are assigned to the same location in a sample, characterized in that the color values of the pixels of the images (24) of a sample are subjected to an assessment of whether they represent a colored signal and/or an uncolored signal, and the pixels, whose color values are assessed with a predetermined likelihood that they are a colored signal or an uncolored signal, are correspondingly binarized, and when the color information is stored, a corresponding binary value is stored for these binarized pixels instead of the color values.

Example 2G of the invention relates to a method according to Example 1G, characterized in that for color values that are not binarized, the particular color values are stored.

Example 3G of the invention relates to a method according to Example 2G, characterized in that an unbinarized color value is reassessed in a subsequent assessment and optionally binarized, in particular if the subsequent assessment achieves the predetermined likelihood that the color value is a colored signal or an uncolored signal.

Example 4G of the invention relates to a method according to one of Examples 1G through 3G, characterized in that after each coloring round or in each case after a predetermined number of coloring rounds, the pixels are subjected to the assessment.

Example 5G of the invention relates to a method according to one of Examples 1G through 4G, characterized in that the assessment of the color values is based on one or more of the following:

a color value that is to be assessed, one or more color values of one or more preceding coloring rounds, statistical values of the measured color values of the coloring rounds previously carried out, one or more color values of background images, and/or statistical values for the background.

Example 6G of the invention relates to a method according to one of Examples 1G through 5G, characterized in that the assessment of whether a color value with a predetermined likelihood represents a colored signal or an uncolored signal is carried out by use of a measure of confidence or heuristics.

Example 7G of the invention relates to a method according to one of Examples 1G through 6G, characterized in that the color values are assessed using a scoring model of a machine learning system, the scoring model learning criteria for assessing the color values for whether they represent, with a certain likelihood, a colored signal and/or an uncolored signal.

Example 8G of the invention relates to a method according to Example 7G, characterized in that the scoring model has been trained using an annotated data set, which as an input data set contains the color values of the pixels and corresponding target outputs, which in each case define whether the color values represent a colored signal or an uncolored signal.

Example 9G of the invention relates to a method according to Example 8G, characterized in that the scoring model has been trained using an annotated data set, which as an input data set contains the color values of the pixels and corresponding target outputs, which in each case define whether the color values represent a colored signal or an uncolored signal, or whether it cannot be determined if they represent a colored signal or an uncolored signal.

Example 10G of the invention relates to a method according to Example 8G or 9G, characterized in that the annotated data set is created using a method in which the color values of the multiple coloring rounds are stored in unbinarized form and then evaluated as to whether they represent a colored signal or an uncolored signal, wherein during the training, for each coloring round the color values that represent a colored signal or uncolored signal are entered as input into the scoring model, an objective function is computed, the objective function indicating a difference between the assessments, output by the scoring model, that the color values represent a colored signal or uncolored signal, and indicating color values according to the annotated data set, which represent a colored signal or an uncolored signal according to the evaluation in the annotated data set, and optimizing the objective function by adapting the model parameters.

Example 11G of the invention relates to a method according to Example 10G, characterized in that during the training, for each coloring round the color values that represent a colored signal or uncolored signal are entered as input into the scoring model, partly as measured color values and partly as binary values.

Example 12G of the invention relates to a method according to one of Examples 8G through 11G, characterized in that the annotated data set has been generated via one or more of the following steps:

simulating signals of the various markers, using a representative background image and a known point spread function of a microscope (2), generating the annotated data set by use of a generative model that has been trained on comparable data, recording reference images that include at least one background image, and for each of the background images for each type of analyte, recording at least one image (24) in which analytes of the particular type of analyte are marked, carrying out a conventional method for spatial identification of analytes, recording a representative background image and subtracting, pixel by pixel, the image signals of the representative background image from the image signals of the images series on which the annotated data set is based, before providing the annotated data set, so that the annotated data set includes only background-corrected color values, and/or obtaining the annotated data set based on a portion of an experiment, so that the trained processing model (5) may be applied to the remaining portion of the experiment.

Example 13G of the invention relates to a method according to one of examples 7G through 12G, characterized in that in addition to the particular color value, further context information is input to the scoring model for the assessment of the color values, which preferably includes the following data:

a color value of the particular pixel of the preceding coloring round, statistical values of the coloring rounds previously carried out, one or more color values of background images, statistical values for the background, the number of expected analytes per experiment or per color channel (20), the codebook used, and/or a user ID.

Example 14G of the invention relates to a method according to one of examples 7G through 13G, characterized in that multiple scoring models are provided, a suitable scoring model being selected based on context information, wherein the context information may describe further properties of the sample and/or of the experiment and/or of the expected analytes, and in particular may include parameters for coloring the sample, and/or the expected number of analytes, or also the expected ratio of the analytes contained in the sample, and based on this context information a scoring model is automatically selected from a set of scoring models.

Example 15G of the invention relates to a method according to Example 14G, characterized in that the context information is obtained by segmentation, and in particular cell areas may be differentiated from areas that are not assigned to a cell.

Example 16G of the invention relates to a method according to one of Examples 1G through 15G, characterized in that an image encompasses a two-dimensional image including multiple pixels as image points, or a three-dimensional image having multiple voxels as image points, and the images may contain time information as an additional dimension.

Example 17G of the invention relates to a method according to one of Examples 1G through 16G, characterized in that the identification of the analytes takes place based on the stored color values, and in part based on the binarized color values.

Example 18G of the invention relates to a method according to one of examples 7G through 17G, characterized in that the scoring model is a convolutional neural network (CNN), a multilayer perceptron (MLP), or a sequential model.

Example 19G of the invention relates to a method according to one of Examples 1G through 18G, characterized in that the analytes are be identified based on the stored color information, and after the analytes are identified, and optionally after a manual correction, an appropriately expanded annotated data set is created, and the processing model is trained using the expanded annotated data set.

Example 20G of the invention relates to a method according to one of Examples 1G through 19G, characterized in that the method also includes, prior to the preparation of data for identifying analytes, a step of carrying out a background correction of the color values, the carrying out of the background correction including one or more of the following:

a rolling ball method, filtering, for example a top hat method, homomorphous filtering, low pass filtering, wherein the result of the low pass filtering is subtracted from the signal, or temporal filtering, background correction by use of an image-to-image model, background correction by use of mixed models, background correction by use of a mean shift method, background correction by use of principal component analysis, background correction by use of non-negative matrix factorization, background correction by the excitation of autofluorescence by use of at least one specific laser for all image areas of the image series, wherein the specific laser corresponds specifically to one excitation spectral range of one of the markers used, and the analytes are not yet marked with markers, or background correction by the excitation of autofluorescence by use of a nonspecific laser for all data points of the images.

Example 21G of the invention relates to a method according to one of preceding Examples 1G through 20G, characterized in that when a minimum number of the color values of a data point has been binarized, a comparison with a codebook takes place, based on the binarized color values and the unbinarized color values of the data point, in order to improve the assessment of previously unbinarized color values.

Example 22G of the invention relates to a method according to preceding Example 17G, wherein the comparison takes place via matrix multiplication of a color value vector by a codebook matrix, the codebook matrix including a target bit sequence for each analyte to be identified, and the color value vector for the binarized color values and for the unbinarized color values including a likelihood value, corresponding to the assessment, between 0 and 1, and the target bit sequences being determined based on a result vector of the matrix multiplication that best fits the color value vector, and the unbinarized color values being binarized based on the determined target bit sequences.

Example 23G of the invention relates to a method for training a machine learning system, using a processing model for carrying out a method according to one of Examples 1G through 22G, comprising:

providing an annotated data set, and optimizing an objective function by adapting the model parameters of the processing model (5), the objective function detecting a difference between a result output

(30) that is output by the processing model (5) and a target output, characterized in that the annotated data set includes at least one target signal series of a candidate data point as well as a target signal series of a background data point, and the processing model (5) processes a partial signal series of the target signal series of the annotated data set as input, and based on an output of the processing model (5), a data point corresponding to the particular target signal series is assessed as a background data point or a candidate data point.

Example 24G of the invention relates to an evaluation unit (4) for evaluating images (24) of multiple coloring rounds, and which in particular is designed as a machine learning system (1), including the means for carrying out the method according to one of the preceding examples.

Example 25G of the invention relates to an image processing system (1), including an evaluation unit (4) according to preceding Example 24G, in particular including an image generation unit such as a microscope (2).

Example 26G of the invention relates to a computer program product that includes commands which, when the program is executed by a computer, prompt the computer to carry out the method according to one of preceding Examples 1G through 23G, the computer program product being in particular a computer-readable memory medium.

Example 27G of the invention relates to a machine learning system (1) that includes an evaluation unit (4), the evaluation unit (4) including a processing model that has been trained according to the method according to Example 23G, in particular including an image generation unit such as a microscope (2).

LIST OF REFERENCE NUMERALS 1 machine learning system
2 microscope
3 control device
4 evaluation unit
5 processing model
6 stand
7 objective revolver
8 mounted objective
9 sample stage
10 mounting frame
11 sample carrier
12 microscope camera
13a illumination device
13b excitation lighting
14 overview camera
15 visual field
16 mirror
17 screen
18 memory module
19 microscopic image registration module
20 channel
21 corresponding target output
22 control module
23 microscopic image readout module
24 microscopic image
26 training data supply module
30 result output
31 objective function module
32 model parameter processing module
33 analysis data supply module
34 result output readout module
35 compression module

36 identification data supply module

37 identification module

38 vector component

39 projection matrix

40 aggregation vector

41 raw data vector

42 cluster analysis module

43 cluster

44 cluster boundary

45 quantization module

46 low-intensity range

47 mid-intensity range

48 high-intensity range

49 predicted image data

50 predicted image

51 difference image

The invention claimed is:

1. A method for preparing data for identifying analytes, the method comprising: coloring one or more analytes with markers in multiple coloring rounds, the markers used in each coloring round being specific for a certain set of analytes, detecting multiple markers using a camera, which for each coloring round generates at least one image that includes multiple pixels, each pixel of the multiple pixels being assigned a color value, and the at least one image includes colored signals and uncolored signals, wherein a colored signal is a pixel for which the assigned color value is attributable to a marker, and an uncolored signal is a pixel for which the assigned color value is not attributable to a marker, and storing color information of the particular coloring rounds for later evaluation, and a data point includes one or more contiguous pixels in the images of the multiple coloring rounds that are assigned to a same location in a sample, wherein the color value assigned to each of the multiple pixels of the at least one image of a sample is subjected to an assessment of whether the pixel to which the color value is assigned is a colored signal or an uncolored signal, and pixels assessed with a predetermined likelihood as being a colored signal or an uncolored signal are correspondingly binarized, and when the color information is stored, a corresponding binary value is stored for these binarized pixels instead of the assigned color value.

2. The method according to claim 1, wherein for color values that are not binarized, the particular color values are stored.

3. The method according to claim 2, wherein an unbinarized color value is reassessed in a subsequent assessment and optionally binarized, in particular if the subsequent assessment achieves the predetermined likelihood that the color value is a colored signal or an uncolored signal.

4. The method according to claim 1, wherein after each coloring round or in each case after a predetermined number of coloring rounds, the pixels are subjected to the assessment.

5. The method according to claim 1, wherein the assessment of the color values is based on one or more of the following:

a color value that is to be assessed, one or more color values of one or more preceding coloring rounds, statistical values of the measured color values of the coloring rounds previously carried out, one or more color values of background images, and/or statistical values for the background.

6. The method according to claim 1, wherein the assessment of whether a color value with a predetermined likelihood represents a colored signal or an uncolored signal is carried out by use of a measure of confidence or heuristics.

7. The method according to claim 1, wherein the color values are assessed using a scoring model of a machine learning system, the scoring model learning criteria for assessing the color values for whether they represent, with a certain likelihood, a colored signal and/or an uncolored signal.

8. The method according to claim 7, wherein the scoring model has been trained using an annotated data set, which as an input data set contains the color values of the pixels and corresponding target outputs, which in each case define whether the color values represent a colored signal or an uncolored signal.

9. The method according to claim 8, wherein the scoring model has been trained using an annotated data set, which as an input data set contains the color values of the pixels and corresponding target outputs, which in each case define whether the color values represent a colored signal or an uncolored signal, or whether it cannot be determined if they represent a colored signal or an uncolored signal.

10. The method according to claim 8, wherein the annotated data set is created using a method in which the color values of the multiple coloring rounds are stored in unbinarized form and then evaluated as to whether they represent a colored signal or an uncolored signal, wherein during the training, for each coloring round the color values that represent a colored signal or uncolored signal are entered as input into the scoring model, an objective function is computed, the objective function indicating a difference between the assessments, output by the scoring model, that the color values represent a colored signal or uncolored signal, and indicating color values according to the annotated data set, which represent a colored signal or an uncolored signal according to the evaluation in the annotated data set, and optimizing the objective function by adapting the model parameters.

11. The method according to claim 10, wherein during the training, for each coloring round the color values that represent a colored signal or uncolored signal are entered as input into the scoring model, partly as measured color values and partly as binary values.

12. A method according to claim 8,
wherein
the annotated data set has been generated via one or more
of the following steps:
  simulating signals of the various markers, using a
    representative background image and a known point
    spread function of a microscope,
  generating the annotated data set by use of a generative
    model that has been trained on comparable data,
  recording reference images that include at least one
    background image, and for each of the background
    images for each type of analyte, recording at least
    one image in which analytes of the particular type of
    analyte are marked,
  carrying out a conventional method for spatial identi-
    fication of analytes,
  recording a representative background image and sub-
    tracting, pixel by pixel, the image signals of the
    representative background image from the image
    signals of the images series on which the annotated
    data set is based, before providing the annotated data
    set, so that the annotated data set includes only
    background-corrected color values, and/or
  obtaining the annotated data set based on a portion of
    an experiment, so that the trained processing model
    may be applied to the remaining portion of the
    experiment.
13. The method according to claim 7,
wherein
in addition to the particular color value, further context
  information is input to the scoring model for the
  assessment of the color values, which preferably
  includes the following data:
  a color value of the particular pixel of the preceding
    coloring round,
  statistical values of the coloring rounds previously
    carried out,
  one or more color values of background images,
  statistical values for the background,
  the number of expected analytes per experiment or per
    color channel,
  the codebook used, and/or
  a user ID.
14. The method according to claim 7,
wherein
multiple scoring models are provided, and based on
  context information, a scoring model is automatically
  selected from the multiple scoring models, wherein the
  context information describes properties of the sample
  and/or of the experiment and/or of the expected ana-
  lytes, including parameters for coloring the sample, an
  expected number of analytes, and/or an expected ratio
  of the analytes contained in the sample.
15. The method according to claim 14,
wherein
the context information is obtained by segmentation, and
  in particular cell areas may be differentiated from areas
  that are not assigned to a cell.
16. The method according to claim 7,
wherein
the scoring model is a convolutional neural network
  (CNN), a multilayer perceptron (MLP), or a sequential
  model.
17. The method according to claim 1,
wherein
an image encompasses a two-dimensional image includ-
  ing multiple pixels as image points, or a three-dimensional image having multiple voxels as image points,
  and the images may contain time information as an
  additional dimension.
18. The method according to claim 1,
wherein
the identification of the analytes takes place based on the
  stored color values, and in part based on the binarized
  color values.
19. The method according to preceding claim 18, wherein
the comparison takes place via matrix multiplication of a
color value vector by a codebook matrix, the codebook
matrix including a target bit sequence for each analyte to be
identified, and the color value vector for the binarized color
values and for the unbinarized color values including a
likelihood value, corresponding to the assessment, between
0 and 1, and the target bit sequences being determined based
on a result vector of the matrix multiplication that best fits
the color value vector, and the unbinarized color values
being binarized based on the determined target bit
sequences.
20. The method according to claim 1,
wherein
the analytes are be identified based on the stored color
  information, and after the analytes are identified, and
  optionally after a manual correction, an appropriately
  expanded annotated data set is created, and the pro-
  cessing model is trained using the expanded annotated
  data set.
21. The method according to claim 1,
wherein
the method also includes, prior to the preparation of data
  for identifying analytes, a step of carrying out a back-
  ground correction of the color values, the carrying out
  of the background correction including one or more of
  the following:
  a rolling ball method,
  filtering, using one of: a top hat method, homomor-
    phous filtering, low pass filtering, wherein the result
    of the low pass filtering is subtracted from the signal,
    or temporal filtering,
  background correction by use of an image-to-image
    model,
  background correction by use of mixed models,
  background correction by use of a mean shift method,
  background correction by use of a principal component
    analysis,
  background correction by use of non-negative matrix
    factorization,
  background correction by the excitation of autofluo-
    rescence by use of at least one specific laser for all
    image areas of the image series, wherein the specific
    laser corresponds specifically to one excitation spec-
    tral range of one of the markers used, and the
    analytes are not yet marked with markers, or
  background correction by the excitation of autofluo-
    rescence by use of a nonspecific laser for all data
    points of the images.
22. The method according to claim 1,
wherein
when a minimum number of the color values of a data
  point has been binarized, a comparison with a code-
  book takes place, based on the binarized color values
  and the unbinarized color values of the data point, in
  order to improve the assessment of previously unbina-
  rized color values.

23. A method for training a machine learning system, using a processing model for carrying out a method according to claim 1, comprising:

providing an annotated data set, and optimizing an objective function by adapting the model parameters of the processing model, the objective function detecting a difference between a result output that is output by the processing model and a target output, wherein the annotated data set includes at least one target signal series of a candidate data point as well as a target signal series of a background data point, and the processing model processes a partial signal series of the target signal series of the annotated data set as input, and based on an output of the processing model, a data point corresponding to the particular target signal series is assessed as a background data point or a candidate data point.

24. An evaluation unit for evaluating images of multiple coloring rounds, wherein the evaluation unit is designed as a machine learning system, and the evaluation unit is configured to carry out the method according to claim 1.

25. An image processing system, including an evaluation unit according to preceding claim 24, in particular including an image generation unit.

26. A computer program product that includes commands which, when the program is executed by a computer, prompt the computer to carry out the method according to claim 1, the computer program product being in particular a non-transitory computer-readable memory medium.

27. A machine learning system that includes an evaluation unit, the evaluation unit including a processing model that has been trained according to the method according to claim 23, in particular including an image generation unit.

\* \* \* \* \*